United States Patent
Christopher et al.

(10) Patent No.: US 9,682,978 B2
(45) Date of Patent: Jun. 20, 2017

(54) 2,6,7 SUBSTITUTED PURINES AS HDM2 INHIBITORS

(71) Applicant: Merck Sharp & Dohme Corp., Rahway, NJ (US)

(72) Inventors: Matthew P. Christopher, Brookline, MA (US); Francesc Xavier Fradera Llinas, Brookline, MA (US); Michelle Machacek, Brookline, MA (US); Michelle Martinez, Watertown, MA (US); Michael Hale Reutershan, Brighton, MA (US); Manami Shizuka, Lexington, MA (US); Binyuan Sun, Needham Heights, MA (US); Christopher Francis Thompson, Arlington, MA (US); B. Wesley Trotter, Medfield, MA (US); Matthew E. Voss, Singapore (SG); Liping Yang, Arlington, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/764,616

(22) PCT Filed: Feb. 4, 2014

(86) PCT No.: PCT/US2014/014638
§ 371 (c)(1),
(2) Date: Jul. 30, 2015

(87) PCT Pub. No.: WO2014/123882
PCT Pub. Date: Aug. 14, 2014

(65) Prior Publication Data
US 2015/0368247 A1  Dec. 24, 2015

Related U.S. Application Data

(60) Provisional application No. 61/762,090, filed on Feb. 7, 2013.

(51) Int. Cl.
C07D 473/30 (2006.01)
C07D 473/34 (2006.01)
C07D 473/00 (2006.01)

(52) U.S. Cl.
CPC ......... C07D 473/34 (2013.01); C07D 473/00 (2013.01); C07D 473/30 (2013.01)

(58) Field of Classification Search
None
See application file for complete search history.

(56) References Cited

U.S. PATENT DOCUMENTS

| 6,734,187 B1 | 5/2004 | Tanaka et al. |
| 2002/0016329 A1 | 2/2002 | Imbach et al. |
| 2003/0100571 A1 | 5/2003 | Vaccaro et al. |
| 2011/0251172 A1 | 10/2011 | Rivkin et al. |
| 2015/0353553 A1* | 12/2015 | Cammarano et al. ................ C07D 473/34 |

FOREIGN PATENT DOCUMENTS

WO   WO2014120748   8/2014

OTHER PUBLICATIONS

Glushkov, R. G. Translated from Khimiko-Farmatsevticheskii Zhurnal, vol. 15, 3, Mar. 16-20, 1981.*
Patani, George. Chem. Rev. 1996, 96, 3147-3176.*
Bernardellia et al., Spiroquinazolinones as novel, potent, and selective PDE7 inhibitors. Part 2: Optimization of 5,8-disubstituted derivatives, Bioorganic & Medicinal Chemistry Letters 14, 2004, 4627-4631, pp. 14-18.
Nichols et al., Preparation of pyrrolidine-based PDE4 inhibitors via enantioselective conjugate addition of alpha-substituted malonates to aromatic nitroalkenes, Organic Letters, 2006, 1495-1498, pp. 8-7.
Retrieved from CAPLUS 1981:407223.
Retrieved from CAPLUS 1996:405108.

* cited by examiner

*Primary Examiner* — Golam M M Shameem
*Assistant Examiner* — Laura Daniel
(74) *Attorney, Agent, or Firm* — Young Zhao; John C. Todaro

(57) ABSTRACT

The present invention provides 2,6,7 substituted purines as described herein or a pharmaceutically acceptable salt thereof. The representative compounds are useful as inhibitors of the HDM2 protein. Also disclosed are pharmaceutical compositions comprising the above compounds and potential methods of treating cancer using the same.

10 Claims, No Drawings

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: labeled peptide
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (4)..(4)
<223> OTHER INFORMATION: 1-AMINO-CYCLOHEXANE CARBOXYLIC ACID
<220> FEATURE:
<221> NAME/KEY: MOD_RES
<222> LOCATION: (5)..(5)
<223> OTHER INFORMATION: 6-BR

<400> SEQUENCE: 1

Phe Arg Xaa Xaa Trp Glu Glu Leu
1               5
```

2,6,7 SUBSTITUTED PURINES AS HDM2 INHIBITORS

FIELD OF THE INVENTION

The present invention relates to novel compounds useful as Human Double Minute 2 ("HDM2") protein inhibitors, regulators or modulators, pharmaceutical compositions containing the compounds and potential methods of treatment using the compounds and compositions to potentially treat diseases such as, for example, cancer, diseases involving abnormal cell proliferation, and diseases caused by inadequate p53 levels.

BACKGROUND OF THE INVENTION

The tumor suppressor protein p53 plays a central role in maintaining the integrity of the genome in a cell by regulating the expression of a diverse array of genes responsible for DNA repair, cell cycle and growth arrest, and apoptosis [May et al., Oncogene 18 (53) (1999) p. 7621-7636; Oren, Cell Death Differ. 10 (4) (2003) p. 431-442, Hall and Peters, Adv. Cancer Res., 68: (1996) p. 67-108; Hainaut et al., Nucleic Acid Res., 25: (1997) p. 151-157; Sherr, Cancer Res., 60: (2000) p. 3689-95]. In response to oncogenic stress signals, the cell triggers the p53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., Genes & Devel. 10: (1996) p. 1054-1072; Levine, Cell 88: (1997) p. 323-331]. The loss of the safeguard functions of p53 predisposes damaged cells to progress to a cancerous state. Inactivating p53 in mice consistently leads to an unusually high rate of tumors [Donehower et al., Nature, 356: (1992) p. 215-221].

The p53 transcription factor promotes the expression of a number of cell cycle regulatory genes, including its own negative regulator, the gene encoding the Mouse Double Minute 2 (MDM2) protein [Chene, Nature Reviews Cancer 3: (2003) p. 102-109; Momand, Gene 242 (1-2): (2000) p. 15-29; Zheleva et al. Mini. Rev. Med. Chem. 3 (3): (2003) p. 257-270]. The MDM2 protein (designated HDM2 in humans) acts to down-regulate p53 activity in an auto-regulatory manner [Wu et al, Genes Dev., 7: (1993) p. 1126-1132; Bairak et al., EMBO J, 12: (1993) p. 461-468]. In the absence of oncogenic stress signals, i.e., under normal cellular conditions, the MDM2 protein serves to maintain p53 activity at low levels [Wu et al, Genes Dev., 7: (1993) p. 1126-1132; Barak et al., EMBO J, 12: (1993) p. 461-468]. However, in response to cellular DNA damage or under cellular stress, p53 activity increases helping to prevent the propagation of permanently damaged clones of cells by induction of cell cycle and growth arrest or apoptosis.

The regulation of p53 function relies on an appropriate balance between the two components of this p53-MDM2 auto-regulatory system. Indeed, this balance appears to be essential for cell survival. There are at least three ways that MDM2 acts to down-regulate p53 activity. First, MDM2 can bind to the N-terminal transcriptional activation domain of p53 to block expression of p53-responsive genes [Kussie et al., Science, 274: (1996) p. 948-953; Oliner et al., Nature, 362: (1993) p. 857-860; Momand et al, Cell, 69: (1992) p. 1237-1245]. Second, MDM2 shuttles p53 from the nucleus to the cytoplasm to facilitate the proteolytic degradation of p53 [Roth et al, EMBO J, 17: (1998) p. 554-564; Freedman et al., Mol Cell Biol, 18: (1998) p. 7288-7293; Tao and Levine, Proc. Natl. Acad. Sci. 96: (1999) p. 3077-3080]. Finally, MDM2 possesses an intrinsic E3 ligase activity for conjugating ubiquitin to p53 for degradation within the ubiquitin-dependent 26S proteosome pathway [Honda et al., FEBS Lett, 420: (1997) p. 25-27; Yasuda, Oncogene 19: (2000) p. 1473-1476]. Thus, MDM2 impedes the ability of the p53 transcription factor to promote the expression of its target genes by binding p53 in the nucleus. Attenuating the p53-MDM2 auto-regulatory system can have a critical effect on cell homeostasis. Consistently, a correlation between the overexpression of MDM2 and tumor formation has been reported [Chene, Nature 3: (2003) p. 102-109]. Functional inactivation of wild type p53 is found in many types of human tumors. Restoring the function of p53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with p53 [Chene, Nature 3: (2003) p. 102-109]. Antibodies, peptides, and antisense oligonucleotides have been demonstrated to destroy the p53-MDM2 interaction, which would release p53 from the negative control of MDM2, leading to activation of the p53 pathway allowing the normal signals of growth arrest and/or apoptosis to function, which offers a potential therapeutic approach to treating cancer and other diseases characterized by abnormal cell proliferation. [See, e.g., Blaydes et al., Oncogene 14: (1997) p. 1859-1868; Bottger et al., Oncogene 13 (10): (1996) p. 2141-2147].

Small molecules, said to antagonize the p53-MDM2 interaction, have been described. WO 00/15657 (Zeneca Limited) describes piperizine-4-phenyl derivatives as inhibitors of the interaction between MDM2 and p53. Grasberger et al. (J. Med. Chem., 48 (2005) p. 909-912) (Johnson & Johnson Pharmaceutical Research & Development L. L. C.) describes discovery and co-crystal structure of benzodiazepinedione as HDM2 antagonists that activate p53 in cells. Galatin et al. (J. Med. Chem. 47 (2004) p. 4163-4165) describes a nonpeptidic sulfonamide inhibitor of the p53-MDM2 interaction and activator of p53 dependent transcription in MDM2-overexpressing cells.

U.S. Pub. No. 2004/0259867 A1 and 2004/0259884 A1 describe Cis-imidazoles (Hoffmann La Roche Inc.) and WO2005/110996A1 and WO 03/051359 describes Cis-Imidazolines (Hoffmann La Roche Inc.) as compounds that inhibit the interaction of MDM2 with p53-like peptides resulting in antiproliferation. WO 2004/080460 A1 describes substituted piperidine compounds as MDM2-p53 inhibitors for treating cancer (Hoffmann La Roche Inc.). EP 0947494 A1 describes phenoxy acetic acid derivatives and phenoxy methyltetrazole that act as antagonists of MDM2 and interfere with the protein-protein interaction between MDM2 and p53, which results in anti-tumor properties (Hoffmann La Roche Inc.). Duncan et al., J. Am. Chem. Soc. 123 (4): (2001) p. 554-560 describes a p-53-MDM2 antagonist, chlorofusin, from a *Fusarium* Sp. Stoll et al., Biochemistry 40 (2) (2001) p. 336-344 describes chalcone derivatives that antagonize interactions between the human oncoprotein MDM2 and p53.

There is a need for effective inhibitors of the HDM2 or MDM2 protein in order to treat or prevent cancer, other disease states associated with cell proliferation, diseases associated with HDM2, or diseases caused by inadequate p53 activity. The present application discloses compounds that have potency in inhibiting or antagonizing the HDM2-p53 and MDM2-p53 interaction and/or activating p53 proteins in cells.

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, potential methods of treatment or prevention of one or more diseases associated with HDM2, MDM2, p53, or p53 peptides by administering such compounds or pharmaceutical compositions.

SUMMARY OF THE INVENTION

In its many embodiments, the present invention provides a novel class of 2,6,7 substituted purine compounds, pharmaceutical compositions comprising one or more said compounds, and potential methods for using said compounds for treating or preventing a disease associated with the HDM2 protein.

Accordingly, in one aspect the present invention provides a compound of Formula I:

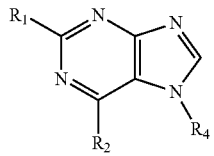

I

DETAILED DESCRIPTION OF THE INVENTION

In one embodiment, the present invention provides compounds illustrated as Formula I, as described above, or pharmaceutically acceptable salts thereof. Accordingly, in one aspect the present invention provides a compound of Formula I:

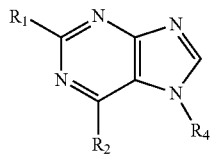

I

Wherein
$R^1$ is selected from the group consisting of $-(CR^a{}_2)_n COOR^{11}$, $-(CR^a{}_2)_n NR^5 SO_2 R^6$, $-(CR^a{}_2)_n SO_2 NR^5 R^6$, $-(CR^a{}_2)_n C(O)NR^c SO_2 N(R^c)_2$, $-(CR^a{}_2)_n C(O)R^5$, $-(CR^a{}_2)_n CONR^5 R^6$, $-(CR^a{}_2)_n S(O)R^c$, $-(CR^a{}_2)_n S(O)_2 R^c$, and a nitrogen containing 5-membered heterocyclyl, heteroaryl and heterocyclenyl ring selected from the group consisting of tetrazolyl, oxadiazolyl, oxadiazolone, dihydro-oxadiazolyl, triazolyl, dihydro-triazolyl, dihydro-triazolone, and pyrrolidinyl, wherein the 5-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_1$-$C_6$alkenyl, $C_1$-$C_6$alkyl-C(=O)O—, $C_1$-$C_6$alkyl-C(=O)—, $C_1$-$C_6$alkynyl, halo group, hydroxyalkoxy, $-SO_2 NR^c R^c$, $-NR^c SO_2 R^c$, $C_1$-$C_6$alkylsulfonyl, $C_1$-$C_6$alkylamino or di($C_1$-$C_6$)alkylamino;

$R^2$ is selected from the group consisting of phenyl, pyridyl, and $-W-(CR^a R^9)_x R^7$, wherein W is $NR^c$ or O, wherein the phenyl or pyridyl is optionally substituted with $R^{12}$ selected from the group consisting of halo, CN, $-(CR^a{}_2)_z COOR^{10}$, halo$C_1$-$C_6$alkyl, $C_1$-$C_6$alkyl, $-OR^c$, $-(CR^a{}_2)_z$aryl, $-(CR^a{}_2)_z$heterocyclic, $-(CR^a{}_2)_z$cyclenyl, and $-(CR^a{}_2)_z$heterocyclenyl, wherein the alkyl, aryl, heterocyclic, cyclenyl and heterocyclenyl of $R^{12}$ can be optionally substituted with OH, $NH_2$, nitro, CN, $CON(R^c)_2$, $-(CR^a{}_2)_z COOR^{10}$, $C_1$-$C_6$alkoxy, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, $-NR^c SO_2 R^c$, $C_1$-$C_6$alkylamino or di($C_1$-$C_6$)alkylamino;

$R^4$ is selected from the group consisting of $C_1$-$C_6$alkyl, $-(CR^a{}_2)_m$aryl, $-(CR^a{}_2)_m$heteroaryl, $-(CR^a{}_2)_m$heterocyclic, $-(CR^a{}_2)_m C_5$-$C_6$cycloalkyl, $-(CR^a{}_2)_m$cyclohexenyl and $-(CR^a{}_2)_m$heterocyclenyl, wherein the alkyl, aryl, heteroaryl, heterocyclic, cycloalkyl, cyclohexenyl, and heterocyclenyl can be optionally substituted with $NH_2$, nitro, CN, $CON(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, $-SO_2 NR^c R^c$, $-NR^c SO_2 R^c$, $C_1$-$C_6$alkylsulfonyl, $C_1$-$C_6$alkylamino or di($C_1$-$C_6$)alkylamino;

$R^5$ is independently selected from the group consisting of H, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, and $-C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, and $-C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, $-C_0$-$C_6$alkylheterocyclic, $-C_0$-$C_6$alkylheterocyclenyl, $-C_0$-$C_6$alkylcyclenyl, $-(CR^a{}_2)_z NR^5 R^6$, $-(CR^a{}_2)_z NR^5 SO_2 R^6$, $-(CR^a{}_2)_z SO_2 NR^5 R^6$, $-(CR^a{}_2)_z C(O)R^5$, $-(CR^a{}_2)_z C(O)OR^{10}$, $-(CR^a{}_2)_z CONR^5 R^6$, $-(CR^a{}_2)_z CONR^5 OR^6$, $-(CR^a{}_2)_z NR^5 C(O)R^6$, $-(CR^a{}_2)_z OR^5$, $-(CR^a{}_2)_z S(O)R^c$, or $-(CR^a{}_2)_z S(O)_2 R^c$;

$R^9$ is independently selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with $-C_0$-$C_6$alkylOR$^c$, $C_0$-$C_6$alkylN(R$^c$)$_2$, $COOR^{10}$, nitro, CN, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, C₁-C₆alkyl-C(=O)—, C₂-C₆alkynyl, halo group, hydroxyalkoxy, —SO₂NR$^c$R$^c$, —NR$^c$SO₂R$^c$, C₁-C₆alkylsulfonyl, heterocylic, or C(O)NHR$^c$;

R$^{10}$ is independently selected from the group consisting of C₁-C₆alkyl, —(CR$^c$₂)$_z$C₃-C₈cycloalkyl, —(CR$^c$₂)$_z$-heteroaryl, —(CR$^c$₂)$_z$-aryl, and —(CR$^c$₂)$_z$-heterocyclic, wherein the heteroaryl, aryl, heterocyclic, cycloalkyl and alkyl can be optionally substituted with C₁-C₆alkyl, OH, halo, or haloC₁-C₆alkyl;

R$^{11}$ is independently selected from the group consisting of H, C₁-C₆alkyl, —(CR$^c$₂)$_z$C₃-C₈cycloalkyl, —(CR$^c$₂)$_z$-heteroaryl, —(CR$^c$₂)$_z$aryl, and —(CR$^c$₂)$_z$heterocyclic, wherein the heteroaryl, aryl, heterocyclic, cycloalkyl and alkyl can be optionally substituted with C₁-C₆alkyl, OH, halo, or haloC₁-C₆alkyl;

R$^a$ is independently H, OR$^c$, NH₂, halo, C₁-C₃alkyl, or C₂-C₃alkenyl, said alkyl or alkenyl is optionally substituted with OH, C₁-C₄alkoxy, NH₂, halo, haloC₁-C₄alkyl, C₃-C₆cycloalkyl, or C₂-C₄alkenyl;

R$^c$ is independently H or C₁-C₃alkyl optionally substituted with C₂-C₃alkenyl, C₃-C₆cycloalkyl, C₁-C₃alkoxy, OH, halo, NH₂, C₁-C₃alkylamino, or C₁-C₃dialkylamino;

n is independently 0, 1, 2 or 3;
m is independently 0, 1 or 2;
t is independently 0, 1, or 2;
z is independently 0, 1, 2 or 3;
or a pharmaceutically acceptable salt thereof.

In one embodiment of the invention,
R$^1$ is selected from the group consisting of COOR$^{11}$ and a nitrogen containing 5-membered heterocyclenyl ring selected from the group consisting of oxadiazolone and dihydro-triazolone, wherein the 5-membered ring can be optionally substituted with C₁-C₆alkyl, C₁-C₆haloalkyl, C₁-C₆haloalkyloxy, or halo group;

R$^2$ is selected from the group consisting of phenyl, pyridyl, and W—(CR$^a$R$^9$)R$^7$, wherein W is NR$^c$ or O, wherein the phenyl and pyridyl is optionally substituted with R$^{12}$ selected from the group consisting of halo, CN, haloC₁-C₆alkyl, C₁-C₆alkyl, and —OR$^c$, wherein the alkyl of R$^{12}$ can be optionally substituted with OH, CN, halo, haloC₁-C₆alkyl, or CON(R')₂;

R$^4$ is selected from the group consisting of —(CR$^a$₂)aryl, —(CR$^a$₂)C₅-C₆cycloalkyl, and —(CR$^a$₂)cyclohexenyl, wherein the aryl, cycloalkyl, and cyclohexenyl can be optionally substituted with CN, C₁-C₃alkoxy, C₁-C₃alkyl, haloC₂-C₃alkenyl, C₂-C₃alkenyl, C₂-C₃alkenoxy, C₁-C₃haloalkyl, C₁-C₃haloalkyloxy, C₁-C₃hydroxyalkyl, C₂-C₃alkynyl, or halo group;

R$^7$ is C₃-C₅cycloalkyl optionally substituted with halo, nitro, CN, C₁-C₆haloalkyl, C$_r$-C₆haloalkyloxy, C₁-C₆alkyl, or —(CR$^a$₂)$_z$OR$^c$;

R$^9$ is H, C₁-C₃alkyl, or C₁-C₃haloalkyl, wherein the alkyl can be optionally substituted with OR N(R')₂, heterocyclic, C(O)NHCH₂CH₂OH, C(O)NH₂, or C(O)NHC₁-C₃alkyl;

R$^{10}$ is C₁-C₃alkyl optionally substituted with OH or halo;

R$^{11}$ is independently selected from the group consisting of H and C₁-C₃alkyl, wherein alkyl can be optionally substituted with OH or halo;

R$^a$ is independently H, OR$^c$, NH₂, halo, C₁-C₃alkyl, or C₂-C₃alkenyl, said alkyl or alkenyl is optionally substituted with OH, C₁-C₄alkoxy, NH₂, F, CF₃, C₃-C₆cycloalkyl, or C₂-C₄alkenyl;

R$^c$ is independently H or C₁-C₃alkyl optionally substituted with C₂-C₃alkenyl, C₃-C₆cycloalkyl, C₁-C₃alkoxy, OH, halo, NH₂, C₁-C₃alkylamino, or C₁-C₃dialkylamino; and z is independently 0, 1 or 2.

In another embodiment of the invention, R$^1$ is COOH,

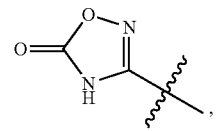

,

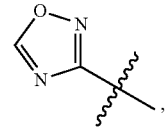

,

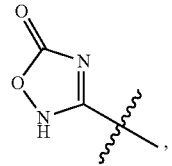

,

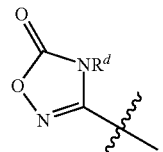

,

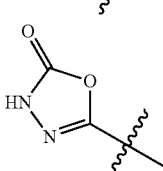

,

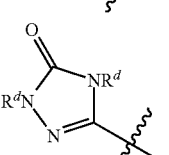

,

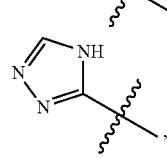

,

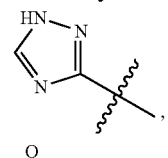

,

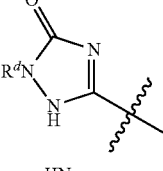

,

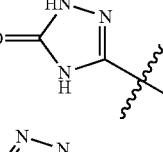

,

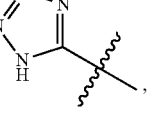

, or

-continued

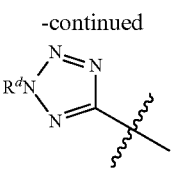

wherein $R^d$ is $CH_3$ or H.

In an aspect of the invention for the foregoing embodiments, $R^1$ is COOH,

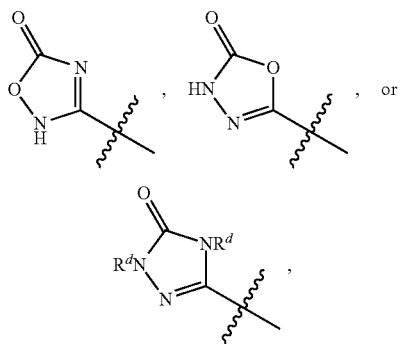

wherein $R^d$ is $CH_3$ or H.

In a another embodiment, $R^1$ is

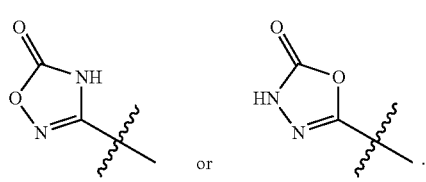 [SMILES: *c1noc(=O)[nH]1 ; *c1n[nH]c(=O)o1]

In another aspect of the invention, $R^2$ is

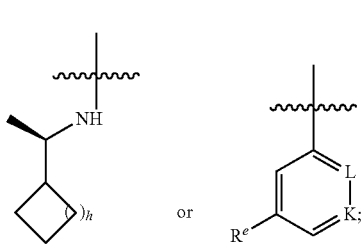

$R^e$ is H, $-(CR^a{}_2)_zC(O)OR^{10}$, CN, $OR^c$, halo, halo$C_1$-$C_3$alkyl or $C_1$-$C_3$alkyl;

K and L are independently $CR^{14}$ or N, and are not both N;

$R^{14}$ is independently H, halo, CN, halo$C_1$-$C_6$alkyl, $C_1$-$C_6$alkyl, $-OR^c$, or $-(CR^a{}_2)_z$heterocyclic, wherein the heterocyclic can be optionally substituted with OH, CN, halo, halo$C_1$-$C_3$alkyl, or $CON(R^c)_2$; and h is 0 or 1.

In one embodiment, $R^2$ is

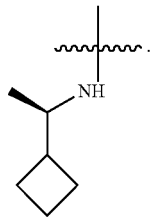

In another embodiment, $R^2$ is

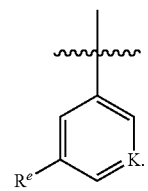

In a further embodiment, $R^2$ is

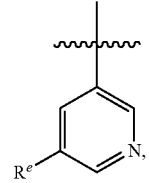

and $R^e$ is halo.

In one embodiment, $R^7$ is cyclopropyl, cyclobutyl, cyclopentyl, or cyclohexyl.

In another embodiment, $R^7$ is cyclobutyl.

In a further aspect of the invention for the foregoing embodiments, $R^4$ is $-CH_2$-E or $-CH_2(CH_3)$-E, wherein E is phenyl, cyclohexyl, cyclohexenyl, cyclopentyl optionally substituted with halo$C_1$-$C_3$alkyl, halo$C_2$-$C_3$alkenyl, halo, $C_3$-$C_4$cycloalkyl, halo$C_1$-$C_3$alkoxy, $C_1$-$C_3$alkoxy, $C_2$-$C_3$alkenoxy, $C_1$-$C_3$alkyl, $C_2$-$C_3$alkenyl, or CN.

In one embodiment, $R^4$ is

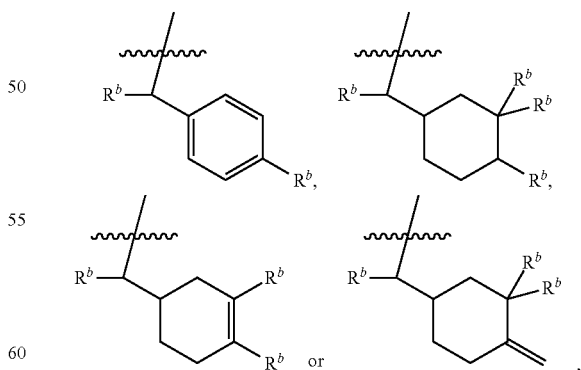

and $R^b$ is independently H, halo$C_1$-$C_3$alkyl, halo$C_2$-$C_3$alkenyl, halo, halo$C_1$-$C_3$alkoxy, $C_1$-$C_3$alkoxy, $C_1$-$C_3$alkyl, $C_2$-$C_3$alkenyl, or CN. In one embodiment, $R^b$ is independently H, halo$C_1$-$C_3$alkyl, halo, halo$C_1$-$C_3$alkoxy, $C_1$-$C_3$alkyl, or $C_2$-$C_3$alkenyl.

In another embodiment, $R^4$ is

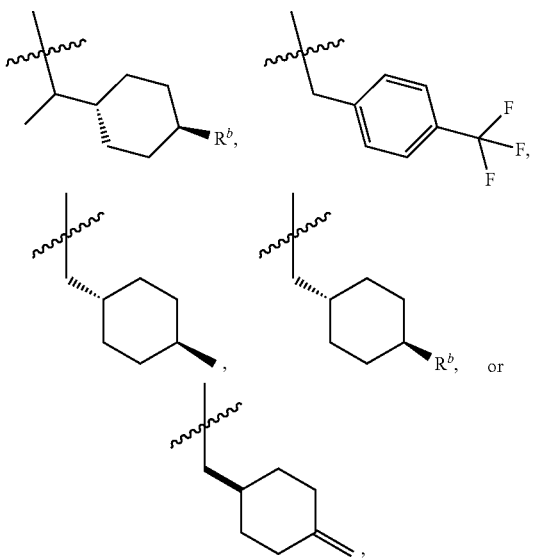

and $R^b$ is independently H, haloC$_1$-C$_3$alkyl, haloC$_2$-C$_3$alkenyl, halo, haloC$_1$-C$_3$alkoxy, C$_1$-C$_3$alkoxy, C$_1$-C$_3$alkyl, C$_2$-C$_3$alkenyl, or CN. In one embodiment, $R^b$ is independently H, haloC$_1$-C$_3$alkyl, halo, haloC$_1$-C$_3$alkoxy, C$_1$-C$_3$alkyl, or C$_2$-C$_3$alkenyl.

In a further embodiment, $R^4$ is

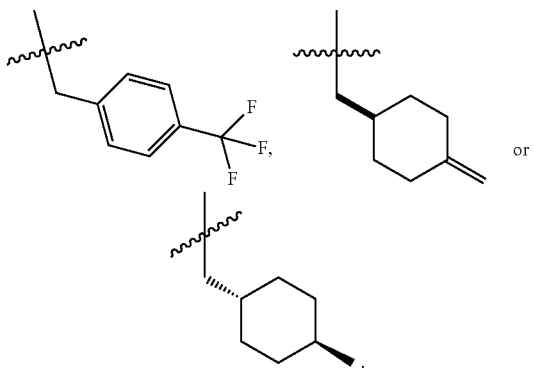

Specific examples of the compounds of the invention include, but not limited to:

6-{[(1R)-1-cyclopropylethyl]amino}-7-[4-(trifluoromethyl)benzyl]-7H-purine-2-carboxylic acid;
6-{[(1R)-1-cyclobutylethyl]amino}-7-[(trans-4-methylcyclohexyl)methyl]-7H-purine-2-carboxylic acid;
5-(6-{[(1R)-1-cyclobutylethyl]amino}-7-[(trans-4-methylcyclohexyl)methyl]-7H-purin-2-yl)-2-methyl-1,2-dihydro-3H-1,2,4-triazol-3-one;
6-{[(1R)-1-cyclobutylethyl]amino}-N-(dimethylsulfamoyl)-7-[(trans-4-methylcyclohexyl)methyl]-7H-purine-2-carboxamide;
3-{6-(3-chlorophenoxy)-7-[(trans-4-methylcyclohexyl)methyl]-7H-purin-2-yl}-1,2,4-oxadiazol-5(4H)-one;
3-{6-(3,3-difluoropiperidin-1-yl)-7-[(trans-4-methylcyclohexyl)methyl]-7H-purin-2-yl}-1,2,4-oxadiazol-5(4H)-one;
3-(6-{[(1R)-1-cyclobutylethyl]amino}-7-[(trans-4-methylcyclohexyl)methyl]-7H-purin-2-yl)-1,2,4-oxadiazol-5(4H)-one;
7-(1-benzothiophen-2-ylmethyl)-6-{[(1R)-1-cyclopropylethyl]amino}-7H-purine-2-carboxylic acid;
3-{6-(3-methoxyphenoxy)-7-[(trans-4-methylcyclohexyl)methyl]-7H-purin-2-yl}-1,2,4-oxadiazol-5(4H)-one;
3-{7-[(trans-4-methylcyclohexyl)methyl]-6-[3-(trifluoromethyl)piperidin-1-yl]-7H-purin-2-yl}-1,2,4-oxadiazol-5(4H)-one;
3-{7-[(trans-4-methylcyclohexyl)methyl]-6-(3-methylpiperidin-1-yl)-7H-purin-2-yl}-1,2,4-oxadiazol-5(4H)-one;
3-{6-(3,3-dimethylpiperidin-1-yl)-7-[(trans-4-methylcyclohexyl)methyl]-7H-purin-2-yl}-1,2,4-oxadiazol-5(4H)-one;
3-{6-(3-chlorophenyl)-7-[(trans-4-methylcyclohexyl)methyl]-7H-purin-2-yl}-1,2,4-oxadiazol-5(4H)-one;
3-{6-(2-chloro-3-fluoropyridin-4-yl)-7-[(trans-4-methylcyclohexyl)methyl]-7H-purin-2-yl}-1,2,4-oxadiazol-5(4H)-one;
3-{6-(4-chloropyridin-2-yl)-7-[(trans-4-methylcyclohexyl)methyl]-7H-purin-2-yl}-1,2,4-oxadiazol-5(4H)-one;
3-chloro-5-{7-[(trans-4-methylcyclohexyl)methyl]-2-(5-oxo-4,5-dihydro-1,2,4-oxadiazol-3-yl)-7H-purin-6-yl}benzonitrile;
3-{6-(5-chloro-2-hydroxyphenyl)-7-[(trans-4-methylcyclohexyl)methyl]-7H-purin-2-yl}-1,2,4-oxadiazol-5(4H)-one;
3-{6-(3-chloro-5-methoxyphenyl)-7-[(trans-4-methylcyclohexyl)methyl]-7H-purin-2-yl}-1,2,4-oxadiazol-5(4H)-one;
3-{6-(3-chloro-5-hydroxyphenyl)-7-[(trans-4-methylcyclohexyl)methyl]-7H-purin-2-yl}-1,2,4-oxadiazol-5(4H)-one;
3-{6-(3-bromophenyl)-7-[(trans-4-methylcyclohexyl)methyl]-7H-purin-2-yl}-1,2,4-oxadiazol-5(4H)-one;
3-{7-[(trans-4-methylcyclohexyl)methyl]-2-(5-oxo-4,5-dihydro-1,2,4-oxadiazol-3-yl)-7H-purin-6-yl}benzonitrile;
3-chloro-N-methyl-5-{7-[(trans-4-methylcyclohexyl)methyl]-2-(5-oxo-4,5-dihydro-1,2,4-oxadiazol-3-yl)-7H-purin-6-yl}benzamide;
3-{6-[3-chloro-5-(trifluoromethyl)phenyl]-7-[(trans-4-methylcyclohexyl)methyl]-7H-purin-2-yl}-1,2,4-oxadiazol-5(4H)-one;
3-{6-(5-chloropyridin-3-yl)-7-[(trans-4-methylcyclohexyl)methyl]-7H-purin-2-yl}-1,2,4-oxadiazol-5(4H)-one;
3-chloro-5-{7-[(trans-4-methylcyclohexyl)methyl]-2-(5-oxo-4,5-dihydro-1,2,4-oxadiazol-3-yl)-7H-purin-6-yl}benzamide;
3-{6-[3-chloro-5-(methoxymethoxy)phenyl]-7-[(trans-4-methylcyclohexyl)methyl]-7H-purin-2-yl}-1,2,4-oxadiazol-5(4H)-one;
3-{6-(2-chloropyridin-4-yl)-7-[(trans-4-methylcyclohexyl)methyl]-7H-purin-2-yl}-1,2,4-oxadiazol-5(4H)-one;
3-{6-(5-chloro-2-hydroxypyridin-3-yl)-7-[(trans-4-methylcyclohexyl)methyl]-7H-purin-2-yl}-1,2,4-oxadiazol-5(4H)-one;
3-{6-[3-chloro-5-(methylsulfonyl)phenyl]-7-[(trans-4-methylcyclohexyl)methyl]-7H-purin-2-yl}-1,2,4-oxadiazol-5(4H)-one;
3-{6-(3-chloro-5-pyrrolidin-1-ylphenyl)-7-[(trans-4-methylcyclohexyl)methyl]-7H-purin-2-yl}-1,2,4-oxadiazol-5(4H)-one;
methyl 3-methyl-5-{7-[(trans-4-methylcyclohexyl)methyl]-2-(5-oxo-4,5-dihydro-1,2,4-oxadiazol-3-yl)-7H-purin-6-yl}benzoate;

3-(6-{[(1R)-1-cyclobutylethyl]amino}-7-{[trans-4-(trifluoromethyl)cyclohexyl]methyl}-7H-purin-2-yl)-1,2,4-oxadiazol-5(4H)-one;

3-[6-(3-chlorophenyl)-7-{[trans-4-(trifluoromethyl)cyclohexyl]methyl}-7H-purin-2-yl]-1,2,4-oxadiazol-5(4H)-one;

3-[6-{[(1R)-1-cyclobutylethyl]amino}-7-(spiro[2.5]oct-6-ylmethyl)-7H-purin-2-yl]-1,2,4-oxadiazol-5(4H)-one;

6-{[(1R)-1-cyclobutylethyl]amino}-7-(spiro[2.5]oct-6-ylmethyl)-7H-purine-2-carboxylic acid;

3-(6-{[(1R)-1-cyclobutylethyl]amino}-7-{[(1R,4R)-3,3-difluoro-4-methylcyclohexyl]methyl}-7H-purin-2-yl)-1,2,4-oxadiazol-5(4H)-one;

3-(6-{[(1R)-1-cyclobutylethyl]amino}-7-[(3-fluoro-4-methylcyclohex-3-en-1-yl)methyl]-7H-purin-2-yl)-1,2,4-oxadiazol-5(4H)-one;

3-(6-{[(1R)-1-cyclobutylethyl]amino}-7-[(4-methylidenecyclohexyl)methyl]-7H-purin-2-yl)-1,2,4-oxadiazol-5(4H)-one;

6-{[(1R)-1-cyclobutylethyl]amino}-7-[(4-methylidenecyclohexyl)methyl]-7H-purine-2-carboxylic acid;

3-(6-{[(1R)-1-cyclobutylethyl]amino}-7-[(3-methylcyclopentyl)methyl]-7H-purin-2-yl)-1,2,4-oxadiazol-5(4H)-one; and 3-(6-(((R)-1-cyclobutylethyl)amino)-7-((3-ethylcyclopentyl)methyl)-7H-purin-2-yl)-1,2,4-oxadiazol-5(4H)-one;

or a stereoisomer thereof;

or a pharmaceutically acceptable salt thereof or a pharmaceutically acceptable salt of the stereoisomer thereof.

Additional examples of the invention include, but are not limited to:

6-{[(1R)-1-cyclobutylethyl]amino}-7-[4-(trifluoromethyl)benzyl]-7H-purine-2-carboxylic acid;

3-(6-{[(1R)-1-cyclobutylethyl]amino}-7-[4-(trifluoromethyl)benzyl]-7H-purin-2-yl)-1,2,4-oxadiazol-5(4H)-one;

5-(6-{[(1R)-1-cyclobutylethyl]amino}-7-[(trans-4-methylcyclohexyl)methyl]-7H-purin-2-yl)-1,3,4-oxadiazol-2(3H)-one;

5-(6-{[(1R)-1-cyclobutylethyl]amino}-7-[(trans-4-methylcyclohexyl)methyl]-7H-purin-2-yl)-4-methyl-2,4-dihydro-3H-1,2,4-triazol-3-one;

6-(5-chloropyridin-3-yl)-7-[(trans-4-methylcyclohexyl)methyl]-7H-purine-2-carboxylic acid;

3-{6-(5-chloro-2-methylpyridin-3-yl)-7-[(trans-4-methylcyclohexyl)methyl]-7H-purin-2-yl}-1,2,4-oxadiazol-5(4H)-one;

3-{6-[3-chloro-5-(2-methoxyethoxyl)phenyl]-7-[(trans-4-methylcyclohexyl)methyl]-7H-purin-2-yl}-1,2,4-oxadiazol-5(4H)-one;

5-{6-[3-chloro-5-(2-methoxyethoxyl)phenyl]-7-[(trans-4-methylcyclohexyl)methyl]-7H-purin-2-yl}-1,3,4-oxadiazol-2(3H)-one;

6-{[(1R)-1-cyclobutylethyl]amino}-7-[(3-ethylcyclopentyl)methyl]-7H-purine-2-carboxylic acid;

3-[6-(3-chlorophenyl)-7-{[(trans)-3,3-difluoro-4-methylcyclohexyl]methyl}-7H-purin-2-yl]-1,2,4-oxadiazol-5(4H)-one; and 3-(6-{[(1R)-1-cyclobutylethyl]amino}-7-[1-(trans-4-methylcyclohexyl)ethyl]-7H-purin-2-yl)-1,2,4-oxadiazol-5(4H)-one;

or a stereoisomer thereof;

or a pharmaceutically acceptable salt thereof or a pharmaceutically acceptable salt of the stereoisomer thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic, or bicyclic saturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on. "cycloalkyl" also includes cycloalkyl rings as described above wherein $=CH_2$ replaces two available hydrogens on the same ring carbon atom.

The term "cyclenyl" means a monocyclic, or bicyclic unsaturated aliphatic hydrocarbon group having the specified number of carbon atoms. The cyclenyl is optionally bridged (i.e., forming a bicyclic moiety), for example with a methylene, ethylene or propylene bridge. The cyclenyl may be fused with an aryl group such as phenyl, and it is understood that the cyclenyl substituent is attached via the cyclenyl group. For example, "cyclenyl" includes cyclopentenyl, cyclohexenyl and so on. "Cyclenyl" also includes cyclenyl rings as described above wherein $=CH_2$ replaces two available hydrogens on the same ring carbon atom.

In an embodiment, if the number of carbon atoms is not specified, "alkyl" refers to $C_1$-$C_6$ alkyl. In an embodiment, if the number of carbon atoms is not specified, "cycloalkyl" refers to $C_3$-$C_7$ cycloalkyl. In an embodiment, if the number of carbon atoms is not specified, "cyclenyl" refers to $C_5$-$C_7$ cyclenyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

"Alkenylene" means a diradical group of an alkenyl group that is defined above. For example, "alkenylene" includes —CH₂—CH₂—CH═CH—CH₂, —CH═CH—CH₂ and the like.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —CH₂Ph, —CH₂CH₂Ph, CH(CH₃)CH₂CH(CH₃)Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbon atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5 to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, in one embodiment, the attachment is via the heteroatom containing aromatic ring, respectively.

Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazolyl, 4-oxazolyl and 5-oxazolyl; isoxazolyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyl and the like.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein ═O replaces two available hydrogens on the same ring carbon atom. An example of such a moiety is pyrrolidone:

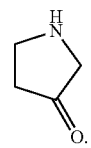

In describing the heteroatoms contained in a specified heterocyclyl group, the expression, "having one to x heteroatoms selected from the group of N, O, P and S" (wherein x is a specified integer), for example, means that each heteroatom in the specified heterocyclyl is independently selected from the specified selection of heteroatoms. Attachment of a heterocyclyl substituent can occur via a carbon atom or via a heteroatom. In cases where the heterocyclyl substituent is bicyclic and one ring is aromatic, unsaturated and/or contains no heteroatoms, in one embodiment, the attachment is via the heteroatom containing non-aromatic saturated ring.

"Heterocyclenyl" means a non-aromatic unsaturated monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The heterocyclenyl is optionally bridged (i.e., forming a bicyclic moiety), for example with a methylene, ethylene or propylene bridge. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

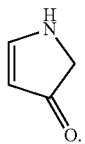

In describing the heteroatoms contained in a specified heterocyclenyl group, the expression, "having one to x heteroatoms selected from the group of N, O, P and S" (wherein x is an a specified integer), for example, means that each heteroatom in the specified heterocyclenyl is independently selected from the specified selection of heteroatoms. In cases where the heterocyclenyl substituent is bicyclic and one ring is aromatic, saturated and/or contains no heteroatoms, in one embodiment, the attachment is via the heteroatom containing non-aromatic unsaturated ring.

It should also be noted that tautomeric forms such as, for example, the moieties:

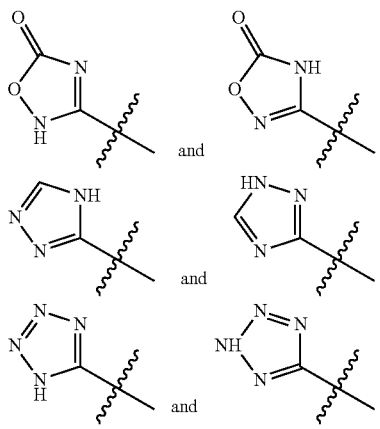

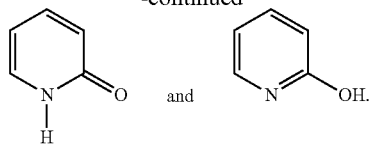

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and suitable alkyl groups are described herein. The bond to the parent moiety is through the cycloalkyl group.

An "arylalkyl group" is an aryl group substituted with an alkyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

An "dialkylamino group" as used herein, is two alkyl groups that are attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

A "haloalkyl group" as used herein, is an alkyl group substituted with a halo group, which is attached to a compound via the alkyl group.

A "hydroxyalkyl group" as used herein, is an alkyl group substituted with a hydroxy group, which is attached to a compound via the alkyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase a group "optionally substituted with" substituent1, etc., or substituent2; substituent selected from the group consisting of substituent1, etc., and substituent2, means the group can be optionally substituted with one or more of the substituents, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

As used herein, the term "composition" is intended to encompass a product comprising the specified ingredients in the specified amounts, as well as any product which results, directly or indirectly, from combination of the specified ingredients in the specified amounts.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Solvates

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

Pharmaceutically Acceptable Salts

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention.

Compounds of Formula I, and salts, solvates thereof, may exist in their tautomeric form (for example, as an amide or imino ether). All such tautomeric forms are contemplated herein as part of the present invention.

Pharmaceutical Compositions

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described potential method of treating a patient by administering a pharmaceutical composition of the present invention is also intended to encompass the administration of the afore-said bulk composition and individual dosage units.

Isolation of the compound at various stages of the reaction may be achieved by standard techniques such as, for example, filtration, evaporation of solvent and the like. Purification of the product and the like, may also be performed by standard techniques such as recrystallization, distillation, sublimation, chromatography, conversion to a suitable derivative. Such techniques are well known to those skilled in the art. The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the compounds of the invention as an active ingredient. The pharmaceutical compositions generally additionally comprise a pharmaceutically acceptable carrier diluent, excipient or carrier (collectively referred to herein as carrier materials).

In yet another embodiment, the present invention discloses methods for preparing pharmaceutical compositions comprising the compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Another aspect of this invention is a kit comprising a therapeutically effective amount of at least one compound of Formula I, or a pharmaceutically acceptable salt of said compound and a pharmaceutically acceptable carrier, vehicle or diluent.

Yet another aspect of this invention is a kit comprising an amount of at least one compound of Formula I, or a pharmaceutically acceptable salt of said compound and an amount of at least one anticancer therapy and/or anti-cancer agent described below, wherein the amounts of the two or more ingredients result in desired therapeutic effect.

"Capsule"—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet"—refers to a compressed or molded solid dosage form containing the active ingredients with suitable diluents. The tablet can be prepared by compression of mixtures or granulations obtained by wet granulation, dry granulation or by compaction.

"Oral gels"—refer to the active ingredients dispersed or solubilized in a hydrophillic semi-solid matrix.

"Powders" for constitution refer to powder blends containing the active ingredients and suitable diluents which can be suspended in water or juices.

"Diluent"—refers to substances that usually make up the major portion of the composition or dosage form. Suitable diluents include but are not limited to sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition.

"Disintegrants"—refers to materials added to the composition to help it break apart (disintegrate) and release the medicaments. Suitable disintegrants include but are not limited to modified starches such as sodium carboxymethyl starch; methylcellulose, microcrystalline celluloses and sodium croscarmellose; and sodium alginate. The amount of disintegrant in the composition can range from about 2 to about 10% by weight of the composition.

"Lubricant"—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as high molecular weight polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition.

"Glidents"—materials that prevent caking and improve the flow characteristics of granulations, so that flow is smooth and uniform. Suitable glidents include silicon dioxide and talc. The amount of glident in the composition can range from about 0.1% to about 5% by weight of the total composition.

"Coloring agents"—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition.

"Conventional" methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Method of Treatment

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formula I can be inhibitors or antagonists of the Human or Mouse Double Minute 2 protein interaction with p53 protein and it can be activators of the p53 protein in cells. Furthermore, the pharmacological properties of the compounds of Formula I may be useful to treat or prevent cancer, treat or prevent other disease states associated with abnormal cell proliferation, and treat or prevent diseases resulting from inadequate levels of p53 protein in cells.

Those skilled in the art will recognize that the term "cancer" is the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of Formula I may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

Due to the key role of p53 in the regulation of cellular apoptosis (cell death), the compounds of Formula I could act as agent to induce cell death which may be useful in the treatment of any disease process which features abnormal cellular proliferation eg, cancers of various origin and tissue types, inflammation, immunological disorders.

Due to the key role of HDM2 and p53 in the regulation of cellular proliferation, the compounds of Formula I could act as reversible cytostatic agents which may be useful in the treatment of any disease process which features abnormal cellular proliferation, inhibitors could act as reversible cytostatic agents which may be useful in the treatment of any disease process which features abnormal cell proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formula I may also be useful in the chemoprevention of cancer. Chemoprevention is defined as inhibiting the development of invasive cancer by either blocking the initiating mutagenic event by blocking the progression of pre-malignant cells that have already suffered an insult or inhibiting tumor relapse.

Compounds of Formula I may also be useful in inhibiting tumor angiogenesis and metastasis.

Another aspect of this invention is a potential method of treating a mammal (e.g., human) having a disease or condition associated with HDM2 by administering a therapeutically effective amount of at least one compound of Formula I, or a pharmaceutically acceptable salt of said compound to the mammal.

The invention also provides a method of inhibiting one or more HDM2 proteins in a patient in need thereof, comprising administering to the patient a therapeutically effective amount of at least one compound of claim 1 or a pharmaceutically acceptable salt thereof.

Another aspect of the present invention is a potential method of treating, or slowing the progression of a disease associated with one or more HDM2 proteins in a patient, comprising administering to a patient in need thereof, a therapeutically effective amount of at least one compound of the present invention or a pharmaceutically acceptable salt thereof.

Another aspect of the present invention is a potential method of treating, or slowing the progression of a disease associated with inadequate p53 levels in a patient, comprising administering to a patient in need thereof, a therapeutically effective amount of at least one compound of the present invention or a pharmaceutically acceptable salt thereof.

Yet another aspect of the present invention is a potential method of treating one or more diseases associated with HDM2, comprising administering to a mammal in need of such treatment an amount of a first compound, which is a compound of the present invention, or a pharmaceutically acceptable salt thereof; and an amount of at least one second compound, the second compound being an anti-cancer agent, wherein the amounts of the first compound and the second compound result in a therapeutic effect.

Another aspect of the present invention is a potential method of treating one or more diseases associated with inadequate p53 levels, comprising administering to a mammal in need of such treatment an amount of a first compound, which is a compound of the present invention, or a pharmaceutically acceptable salt thereof; and an amount of at least one second compound, the second compound being an anti-cancer agent, wherein the amounts of the first compound and the second compound result in a therapeutic effect.

Another aspect of the present invention is a potential method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt thereof.

Another aspect of the present invention is a potential method of treating, or slowing the progression of, a disease associated with inadequate p53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt thereof.

In one embodiment, the dosage is about 0.001 to 500 mg/kg of body weight/day of the compound of Formula I. In another embodiment, the dosage is about 0.01 to 25 mg/kg of body weight/day of a compound of Formula I, or a pharmaceutically acceptable salt of said compound.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Patient" includes both human and animals.

"Mammal" means humans and other mammalian animals.

Combination Therapy

The instant compounds may also be useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, α-secretase inhibitors, agents that interfere with receptor tyrosine kinases (RTKs) and agents that interfere with cell cycle checkpoints. The instant compounds may also be useful when co-administered with radiation therapy. The compounds of the present invention can be present in the same dosage unit as the anticancer agent or in separate dosage units.

Another aspect of the present invention is a potential method of treating one or more diseases associated with HDM2, comprising administering to a mammal in need of such treatment an amount of a first compound, which is a compound of the present invention, or a pharmaceutically acceptable salt thereof; and an amount of at least one second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and micro-RNA) against cancer and neoplastic diseases;

1) Anti-metabolites (such as methoxtrexate, 5-fluorouracil, gemcitabine, fludarabine, capecitabine);
2) Alkylating agents, such as temozolomide, cyclophosphamide,
3) DNA interactive and DNA damaging agents, such as cisplatin, oxaliplatin, doxorubicin, 4) Ionizing irradiation, such as radiation therapy,
5) Topoisomerase II inhibitors, such as etoposide, doxorubicin,
6) Topoisomerase I inhibitors, such as irinotecan, topotecan,
7) Tubulin interacting agents, such as paclitaxel, docetaxel, Abraxane, epothilones, 8) Kinesin spindle protein inhibitors,
9) Spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) Sex hormone modulating agents,
   a. anti-estrogens, such as tamoxifen, fulvestrant,
   b. selective estrogen receptor modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 $C_{17}$ lyase (CYP450c17, also called 17α-hydroxylase/17,20 lyase) inhibitors, such as Abiraterone acetate, VN/124-1, TAK-700
   g. aromatase inhibitors, such as letrozole, anastrozole, exemestane,
20) EGFR kinase inhibitors, such as geftinib, erlotinib, laptinib
21) Dual erbB1 and erbB2 inhibitors, such as Lapatinib
22) Multi-targeted kinases (serine/threonine and/or tyrosine kinase) inhibitors,
   a. ABL kinase inhibitors, imatinib and nilotinib, dasatinib
   b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
   c. Polo-like kinase inhibitors
   d. Aurora kinase inhibitors
   e. JAK inhibitor
   f. c-MET kinase inhibitors
   g. Cyclin-dependent kinase inhibitors, such as CDK1 and CDK2 inhibitor SCH 727965
   h. PI3K and mTOR inhibitors, such as GDC-0941, BEZ-235, BKM-120 and AZD-8055
   i. Rapamycin and its analogs, such as Temsirolimus, everolimus, and deforolimus
23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.
24) Farnesyl protein transferase inhibitors, such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) Anti-CTLA-4 antibodies, such as ipilimumab
34) antibodies against CTAT, CEA, CD5, CD19, CD22, CD30, CD44, CD44V6, CD55, CD56, EpCAM, FAP, MHCII, HGF, IL-6, MUC1, PSMA, TALE, TAG-72, TRAILR, VEGFR, IGF-2, FGF, 35) anti-IGF-1R antibodies, such as dalotuzumab (MK-0646) and robatumumab (SCH 717454).

If formulated as a fixed dose such combination products employ the compounds of this invention within the dosage range described herein and the other pharmaceutically active agent or treatment within its dosage range. Compounds of Formula I may also be administered sequentially with known anticancer or cytotoxic agents when a combination formulation is inappropriate. The invention is not limited in the sequence of administration; compounds of Formula I may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formula I, or a pharmaceutically acceptable salt thereof, and an amount of one or more anti-cancer treatments and anti-cancer agents listed above wherein the amounts of the compounds/treatments result in desired therapeutic effect.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (H)]-tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabin furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®, see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_5O$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598.

Inhibitors of COX-2 may also be useful in the instant method of treatment are: 3-phenyl-4-(4-(methylsulfonyl) phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and may therefore be useful in the present invention include, but are not limited to, the following: parecoxib, BEXTRA® and CELEBREX® or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_3$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_v\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxy]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed compounds with PPAR-γ (i.e., PPAR-gamma) agonists and PPAR-δ (i.e., PPAR-delta) agonists may be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

Another embodiment of the instant invention is the use of the presently disclosed compounds in combination with gene therapy for the potential treatment of cancer. For an overview of genetic strategies to treating cancer see Hall et al (*Am. J. Hum. Genet.* 61:785-789, 1997) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with α-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa)antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, may also be useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors: olaparib, MK-4827 and veliparib.

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard); levamisole (Ergamisol®); lomustine, CCNU (CeeBU); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®);

tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742).

The invention disclosed herein is exemplified by the following preparations and examples which should not be construed to limit the scope of the disclosure.

EXAMPLE 1

Methods of Preparing the Compounds of Formula
(I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:
Me=methyl; Et=ethyl; Pr=propyl; iPr=isopropyl, Bu=butyl; t-Bu=tert-butyl; Ph=phenyl, and Ac=acetyl
μl=microliters
AcOH or HOAc=acetic acid
ACN=acetonitrile
Ad=adamantyl
APCI or APC=atmospheric-pressure chemical ionization
aq=aqueous
Bn=benzyl
Boc or BOC32 tert-butoxycarbonyl
Bz=benzoyl
Cbz=benzyloxycarbonyl
CDI=1,1'-Carbonyldiimidazole
DAST=diethylaminosulfur trifluoride
Dba=dibenzylideneacetone
DBU=1,8-Diaza-7-bicyclo[5.4.0]undecene
DCM=dichloromethane
DMAP=4-Dimethylaminopyridine
DIBAL=diisobutylaluminum hydride
DIEA or Hürig's Base=N,N-diisopropylethylamine
DMA=N,N-dimethylacetamide
DMF=dimethylformamide
DMSO=dimethyl sulfoxide
Dppf=1,1'-Bis(diphenylphosphino)ferrocene
DMT=Dimercaptotriazine
DTT=dithiothreitol
EDC=1-ethyl-3-(3-dimethylaminopropyl)carbodiimide
EDTA32 ethylenediamine tetraacetic acid
ESI or ES=Electrospray ionization
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl) uronium hexafluorophosphate
HPLC=high-performance liquid chromatography
HOBt=1-hydroxybenzotriazole
LAH=lithium aluminium hydride
LDA=lithium diisopropylamide
LC=liquid chromatography
LCMS=liquid chromatography mass spectrometry
min=minute
mg=milligrams
mL=milliliters
mmol=millimoles
mCPBA=meta-Chloroperoxybenzoic acid
Me=methyl
MeOH=methanol
MS=mass spectrometry
NBS=N-bromosuccinimide
NMP=N-methylpyrrolidone
NMR=nuclear magnetic resonance spectroscopy
PTLC=preparative thin layer chromatography
rac=racemic mixture
$R_f$=retardation factor
RT or rt=room temperature (ambient, about 25° C.)
sat=saturated
SFC=supercritical fluid chromatography
TBSC$_1$=t-butyldimethylsilyl chloride
TBS=t-butyldimethylsilyl
TEA=triethylamine (Et$_3$N)
TFA=trifluoroacetic acid
TFAA=trifluoroacetic anhydride THF=tetrahydrofuran
TLC=thin layer chromatography
TMS=trimethylsilyl
Tris=tris(hydroxymethyl)aminomethane
Xantphos=4,5-Bis(diphenylphosphino)-9,9-dimethylxan-thene
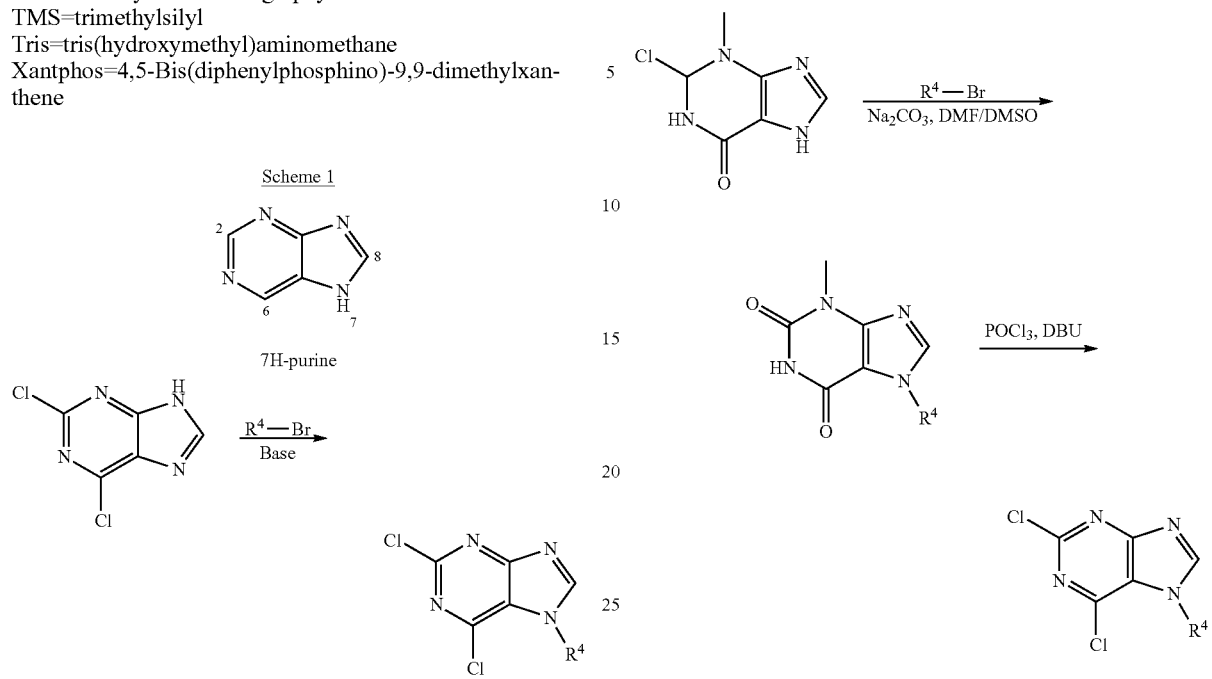
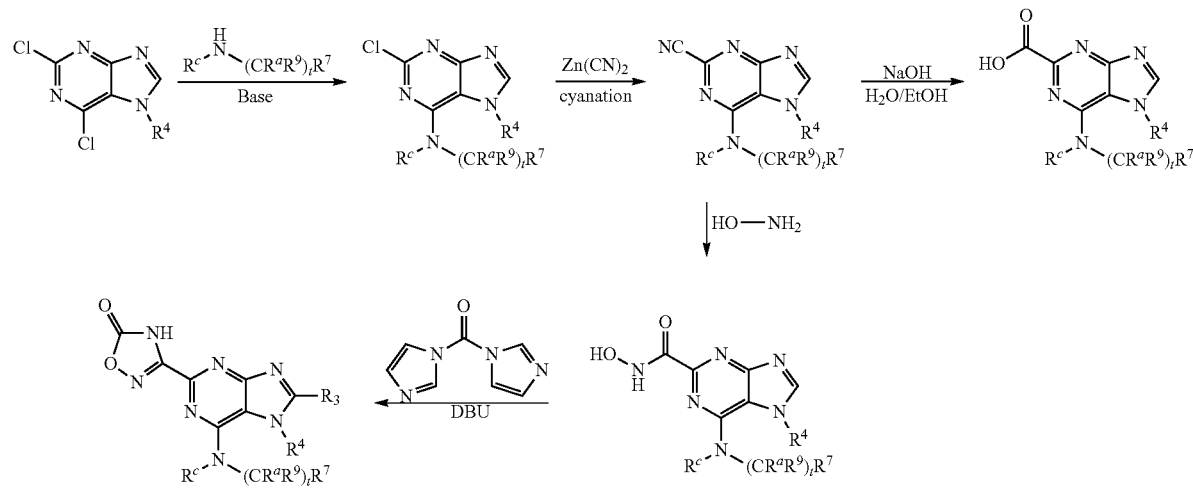
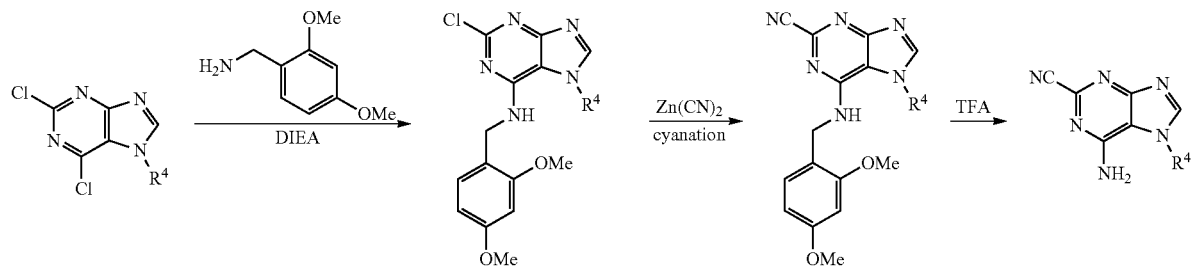

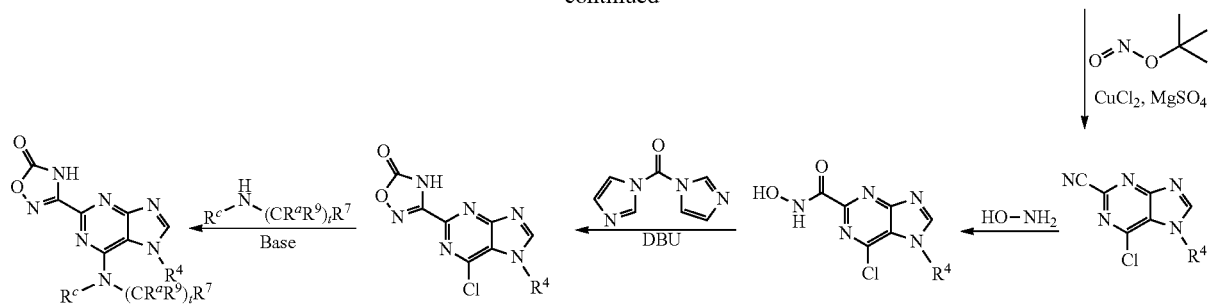

Scheme 4

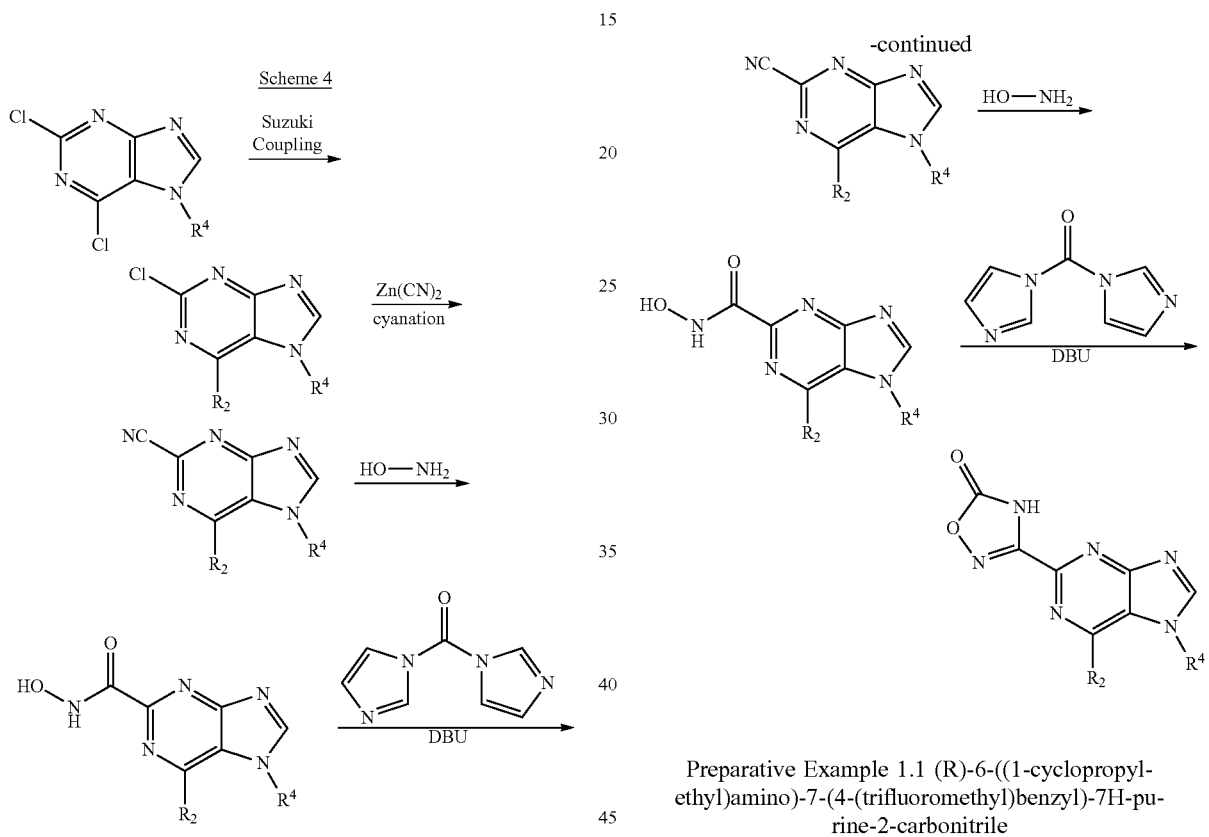

Scheme 5

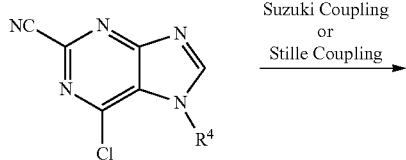

Preparative Example 1.1 (R)-6-((1-cyclopropylethyl)amino)-7-(4-(trifluoromethyl)benzyl)-7H-purine-2-carbonitrile

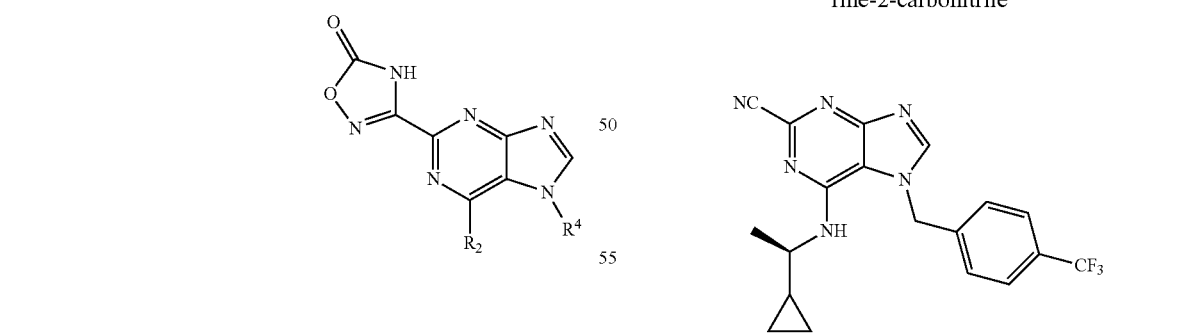

Step 1: Into a 20-L 4-necked round-bottom flask purged and maintained with an inert atmosphere of nitrogen was placed a solution of sodium tert-butoxide (403 g, 4.19 mol) in tetrahydrofuran (6.5 L). This was followed by the addition of 2,6-dichloro-7H-purine (658 g, 3.48 mol) in several batches. To this was added dropwise a solution of 1-(bromomethyl)-4-(trifluoromethyl)benzene (1000 g, 4.18 mol) in tetrahydrofuran (3 L) with stirring over 3 hours while the reaction mixture was heated to reflux. The resulting solution was heated at reflux overnight in an oil bath. The reaction mixture was cooled to room temperature and then concentrated under vacuum. The residue was diluted with 5 L of water and then extracted with ethyl acetate (3×4 L). The organic layers were combined, washed with brine (3×4 L), dried over sodium sulfate and concentrated under vacuum. The residue was applied onto a silica gel column and eluted with ethyl acetate/petroleum ether (1:2) to give 2,6-dichloro-7-(4-(trifluoromethyl)benzyl)-7H-purine as the minor product and 2,6-dichloro-9-(4-(trifluoromethyl)benzyl)-9H-purine as the major product.

Step 2: 2,6-dichloro-7-(4-(trifluoromethyl)benzyl)-7H-purine (1.7 g, 4.9 mmol) was slurried in IPA (8.5 mL) and treated with triethyl amine (0.743 g, 7.35 mmol) and (R)-1-cyclopropylethanamine (0.626 g, 7.35 mmol). The reaction mixture was heated at 80° C. for 2 hours. After the solution was cooled to room temperature, water was added and oil was separated. A mixture of $H_2O$/EtOAc (20 mL/80 mL) was added and the organic layer was separated and concentrated to an oil. EtOAc (2 mL) was added followed by hexanes. After 10 minutes of stirring, solid started to precipitate out. Hexane (20 mL) was added, and the solid was filtered and dried to afford (R)-2-chloro-N-(1-cyclopropylethyl)-7-(4-(trifluoromethyl)benzyl)-7H-purin-6-amine. MS ESI calc'd. for $C_{18}H_{17}C_1F_3N_5$ $[M+H]^+$396, found 396.

Step 3: To allyl palladium chloride (0.055 g, 0.152 mmol) and 2-(dicyclohexylphosphino)-2',4',6'-triisopropylbiphenyl (0.253 g, 0.531 mmol) was added DMA (12.0 ml) and the solution was degassed. The solution was heated at 50° C. for 30 min and then (R)-2-chloro-N-(1-cyclopropylethyl)-7-(4-(trifluoromethyl)benzyl)-7H-purin-6-amine (1.5 g, 7.9 mmol) and zinc cyanide (0.579 g, 4.93 mmol) were added. The mixture was purged with $N_2$ (3×) and heated at 120° C. for 2 h. The reaction mixture was cooled to room temperature and purified by silica gel chromatography to afford an off white solid. The material was slurried in EtOAc/hexanes (1:4, 30 mL) and filtered to afford (R)-6-((1-cyclopropylethyl)amino)-7-(4-(trifluoromethyl)benzyl)-7H-purine-2-carbonitrile. MS ESI calc'd. for $C_{19}H_{17}F_3N_6$ [M+H]+ 387, found 387.

Example 1.1: 6-{[(1R)-1-cyclopropylethyl]amino}-7-[4-(trifluoromethyl)benzyl]-7H-purine-2-carboxylic acid

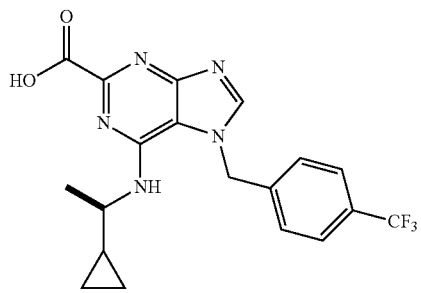 [SMILES: C[C@@H](Nc1nc(C(=O)O)nc2ncn(Cc3ccc(C(F)(F)F)cc3)c12)C1CC1]

To a solution of (R)-6-((1-cyclopropylethyl)amino)-7-(4-(trifluoromethyl)benzyl)-7H-purine-2-carbonitrile (63 mg, 0.13 mmol, Preparative Example 1.1) in ethanol (1 ml) was added sodium hydroxide solution (5.0 M in water, 0.5 mL, 2.5 mmol). The reaction mixture was heated to 70° C. and stirred for 2 h. After the solution was cooled to room temperature, it was concentrated, diluted with EtOAc and washed with 1N HCl, then dried over sodium sulfate, filtered and concentrated. The residue was dissolved in DMSO and purified by mass triggered, reverse phase (C-18) preparative HPLC (acetonitrile/water: 0.1% v/v trifluoroacetic acid modifier) to afford 6-{[(1R)-1-cyclopropylethyl]amino}-7-[4-(trifluoromethyl)benzyl]-7H-purine-2-carboxylic acid. MS ESI calc'd. for $C_{19}H_{18}F_3N_5O_2[M+H]^+$ 406, found 406. $^1$H NMR (500 MHz, DMSO-$d_6$): δ 8.62 (s, 1H); 7.71 (d, J=8.0 Hz, 2H); 7.29 (d, J=8.0 Hz, 2H); 6.46 (d, J=7.9 Hz, 1H); 5.92-5.94 (m, 2H); 3.58-3.61 (m, 1H); 1.12 (d, J=6.5 Hz, 3H); 0.84-0.92 (m, 1H); 0.33-0.36 (m, 1H); 0.10-0.13 (m, 3H).

Preparative Example 1.2: 6-[[(1R)-1-cyclobutylethyl]amino]-7-[(trans-4-methylcyclohexyl)methyl]-7H-purine-2-carbonitrile

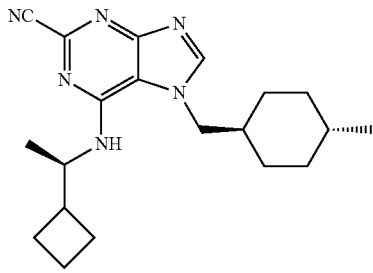 [SMILES: C[C@@H](Nc1nc(C#N)nc2ncn(C[C@H]3CC[C@H](C)CC3)c12)C1CCC1]

Step 1: To a solution of trans-4-methylcyclohexanecarboxylic acid (113.6 g, 0.8 mmol) in dry tetrahydrofuran (800 mL) was added borane in tetrahydrofuran (1M, 800 mL, 0.8 mol) dropwise at 0° C. under a nitrogen atmosphere over 1 h. Then the reaction mixture was warmed to room temperature and stirred for 8 h. The reaction was quenched with $NH_4Cl$ solution at 0° C., diluted with water (2 L) and then extracted with ethyl acetate (1 L×3). The organic layer was washed with water (2×1 L) and brine (1 L), dried over anhydrous $Na_2SO_4$, filtered and concentrated to give (trans-4-methylcyclohexyl)methanol, which was used for next step without further purification.

Step 2: To a solution of (trans-4-methylcyclohexyl)methanol (150 g, 1.17 mol) and $CBr_4$ (450 g, 1.35 mol) in dichloromethane (1.0 L) was added $PPh_3$ (300 g, 1.17 mol) dissolved in dichloromethane (0.5 L) dropwise at 0° C. over 1 h. The reaction was warmed to room temperature and stirred for 12 h. The reaction mixture was filtered and the filtrate was concentrated. The residue was diluted with hexane:EtOAc (9:1) (3 L) and stirred for 1 h. The solid was filtered off and the filtrate was concentrated to give trans-1-(bromomethyl)-4-methylcyclohexane, which was used for next step without further purification.

Step 3: A suspension of 3-methyl-1H-purine-2,6(3H,7H)-dione (100 g, 0.60 mol), trans-1-(bromomethyl)-4-methylcyclohexane (160 g, 0.84 mol) and sodium carbonate (192 g, 1.81 mol) dissolved in anhydrous DMF (900 mL) and DMSO (900 mL) was stirred at 100° C. for 24 h. The reaction mixture was cooled and poured into ice water. The mixture was filtered and the solids were washed with cold water and dried to give 3-methyl-7-((trans-4-methylcyclohexyl)methyl)-1H-purine-2,6(3H,7H)-dione. $^1$H NMR (400 MHz, DMSO-$d_6$) δ: 11.04 (s, 1H), 7.96 (s, 1H), 4.02-4.00 (d, J=7.2 Hz, 2H), 3.32 (s, 3H), 1.69-0.79 (m, 13H).

Step 4: To a suspension of 3-methyl-7-((trans-4-methylcyclohexyl)methyl)-1H-purine-2,6(3H,7H)-dione (150 g, 0.54 mol) in POCl$_3$ (900 mL) was added DBU (300 mL) at 60° C. The reaction mixture was heated at 120° C. for 5 h. The reaction mixture was cooled to ambient temperature and excess POCl$_3$ was removed by evaporation under reduced pressure. The residue was poured into water slowly and the pH of the solution was adjusted to neutral using NaOH. The aqueous solution was then extracted with dichloromethane, the combined organic layers were dried over Na$_2$SO$_4$, filtered and concentrated. Purification of the residue by silica gel column chromatography afforded 2,6-dichloro-7-((trans-4-methylcyclohexyl)methyl)-7H-purine. $^1$H NMR (400 MHz, CDCl$_3$) δ: 8.19 (s, 1H), 4.27-4.25 (d, J=7.6 Hz, 2H), 1.78-0.83 (m, 13H).

Step 5: Into a 3000-mL 3-necked round-bottom flask was placed a solution of 2,6-dichloro-7-[(trans-4-methylcyclohexyl)methyl]-7H-purine (129 g, 418.22 mmol, 97%) in IPA (1000 mL). This was followed by the addition of triethylamine (52.4 g, 517.84 mmol) at 25° C. Next was added (1R)-1-cyclobutylethan-1-amine hydrochloride (62 g, 457.11 mmol) at 25° C. The resulting solution was stirred overnight at 90° C. in an oil bath. The reaction was then cooled to room temperature and concentrated under vacuum. The residue was diluted with 1000 mL of water. The resulting mixture was extracted with ethyl acetate (3×1000 mL). The organic layers were combined, washed with brine (1×1000 mL), dried over anhydrous sodium sulfate and concentrated under vacuum. The residue was purified via silica gel column chromatography eluting with dichloromethane:methanol (40:1) to afford 2-chloro-N-[(1R)-1-cyclobutylethyl]-7-[(trans-4-methylcyclohexyl)methyl]-5,7-dihydro-4H-purin-6-amine.

Step 6: Into each of twenty 20-mL vials purged and maintained with an inert atmosphere of nitrogen was added a solution of 2-chloro-N-[(1R)-1-cyclobutylethyl]-7-[(trans-4-methylcyclohexyl)methyl]-7H-purin-6-amine (3 g, 8.04 mmol, 97%) in DMA (18 mL). Followed by the addition of Zn(CN)$_2$ (1.26 g, 10.77 mmol) at 25° C. To the suspension was added X-phos (1.025 g, 2.15 mmol) at 25° C. and allylpalladium (II) chloride dimer (303 mg, 0.83 mmol) at 25° C. The reaction mixtures were irradiated in a microwave for 1 hr at 150° C. The 20 batches were combined and diluted with 200 mL of EA and 100 mL of aq. sodium bicarbonate. Solids were removed by filtration. The filtrate was extracted with 3×500 mL of ethyl acetate. The organic layers were combined, washed with brine (1×1000 mL), dried over anhydrous sodium sulfate and concentrated under vacuum. The residue was purified via column chromatography on silica gel eluting with ethyl acetate: petroleum ether (1:2) to afford 6-[[(1R)-1-cyclobutylethyl]amino]-7-[(trans-4-methylcyclohexyl)methyl]-7H-purine-2-carbonitrile. MS ESI calc'd. for C$_{20}$H$_{28}$N$_6$ [M+H]$^+$ 353, found 353. $^1$H NMR (400 MHz, DMSO-d6): δ 8.45 (1H, s), 6.68-6.71 (1H, d, J=11.6 Hz), 4.58-4.65 (1H, m), 4.31-4.33 (1H, m), 4.13-4.20 (1H, m), 2.54-2.59 (1H, m), 1.49-2.03 (10H, m), 1.12-1.25 (5H, m), 0.91-1.02 (2H, m), 0.64-0.81 (5H, m).

Example 1.2: 6-{[(1R)-1-cyclobutylethyl]amino}-7-[(trans-4-methylcyclohexyl)methyl]-7H-purine-2-carboxylic acid

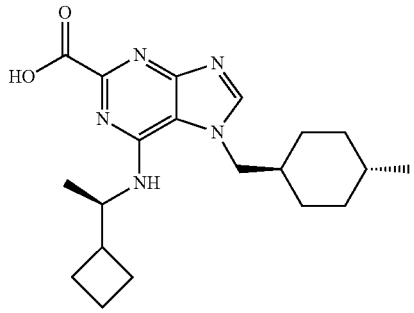 [SMILES: C[C@@H](Nc1nc(C(=O)O)nc2ncn(C[C@H]3CC[C@H](C)CC3)c12)C1CCC1]

To a suspension of 6-{[(1R)-1-cyclobutylethyl]amino}-7-[(trans-4-methylcyclohexyl)methyl]-7H-purine-2-carbonitrile (37 mg, 0.105 mmol, Preparative Example 1.2) in EtOH (2 mL) was added 5N NaOH (1 mL, 5 mmol). The reaction was stirred vigorously at 70° C. for 2.5 hours and then quenched with 1N HCl. The mixture was diluted with EtOAc and washed with water and brine. The organic layer was dried over Na$_2$SO$_4$, filtered, and concentrated. Purification of the residue by mass triggered reverse phase HPLC (C-18), eluting with acetonitrile/water containing 0.1% TFA afforded 6-{[(1R)-1-cyclobutylethyl]amino}-7-[(trans-4-methylcyclohexyl)methyl]-7H-purine-2-carboxylic acid. MS ESI calc'd. for C$_{20}$H$_{29}$N$_5$O$_2$ [M+H]$^+$ 372, found 372. $^1$H NMR (600 MHz, CD$_3$OD) δ 8.34 (s, 1H), 4.80-4.71 (m, 1H), 4.54 (dd, J=14.7, 6.1, 1H), 4.29-4.17 (m, 1H), 2.63-2.52 (m, 1H), 2.16-2.05 (m, 1H), 2.05-1.95 (m, 1H), 1.98-1.79 (m, 4H), 1.77-1.69 (m, 1H), 1.69-1.51 (m, 3H), 1.39-1.25 (m, 2H), 1.21 (d, J=6.3, 3H), 1.14-0.99 (m, 2H), 0.93-0.68 (m, 5H).

Example 1.3: 5-(6-{[(1R)-1-cyclobutylethyl]amino}-7-[(trans-4-methylcyclohexyl)methyl]-7H-purin-2-yl)-2-methyl-1,2-dihydro-3H-1,2,4-triazol-3-one

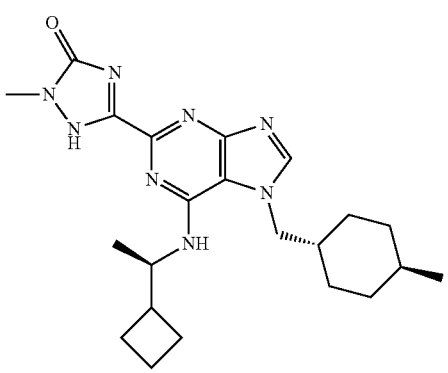

Step 1: Sodium methoxide (2.4 mg, 0.04 mmol) was added to a solution of 6-(((R)-1-cyclobutylethyl)amino)-7-((trans-4-methylcyclohexyl)methyl)-7H-purine-2-carbonitrile (155 mg, 0.44 mmol, Preparative Example 1.2) in methanol (440 μL) and the reaction mixture was allowed to stir at ambient temperature overnight. The reaction was concentrated to afford crude methyl 6-(((R)-1-cyclobutylethyl)amino)-7-((trans-4-methylcyclohexyl)methyl)-7H-purine-2-carbimidate. LCMS=385 (M+1)⁺. This material was taken on to Step 2 without further purification.

Step 2: Methylhydrazine (116 µL, 2.2 mmol) was added to a solution of crude methyl 6-(((R)-1-cyclobutylethyl)amino)-7-((trans-4-methylcyclohexyl)methyl)-7H-purine-2-carbimidate (170 mg, 0.44 mmol) in methanol (4.4 mL) and the reaction vial was sealed and stirred at 50° C. for 45 minutes. The reaction mixture was diluted with EtOAc and washed with water and brine. The organic layer was dried over Na$_2$SO$_4$, filtered, and concentrated to afford crude 6-(((R)-1-cyclobutylethyl)amino)-N'-methyl-7-((trans-4-methylcyclohexyl)methyl)-7H-purine-2-carboximidhydrazide. LCMS=399 (M+1)⁺. This material was taken on to Step 3 without further purification.

Step 3: CDI (107 mg, 0.439 mmol) and DBU (397 µL, 2.63 mmol) were added to a solution of crude 6-(((R)-1-cyclobutylethyl)amino)-N'-methyl-7-((trans-4-methylcyclohexyl)methyl)-7H-purine-2-carboximidhydrazide (175 mg, 0.439 mmol) in ACN (4.8 mL) and the reaction mixture was stirred at ambient temperature overnight. The reaction was then diluted with DCM and the organics were washed with 2N HCl. The aqueous layer was extracted with DCM (3×) and the combined organics were washed with brine. The organic layer was dried over Na$_2$SO$_4$, filtered, and concentrated. Purification of the residue by mass triggered reverse phase HPLC (C-18), eluting with acetonitrile/water containing 0.1% TFA afforded 5-(6-{[(1R)-1-cyclobutylethyl]amino}-7-[(trans-4-methylcyclohexyl)methyl]-7H-purin-2-yl)-2-methyl-1,2-dihydro-3H-1,2,4-triazol-3-one. MS ESI calc'd. for C$_{22}$H$_{32}$N$_8$O [M+H]+ 425, found 425. $^1$H NMR (600 MHz, CD$_3$OD) δ 8.18 (s, 1H), 4.79-4.69 (m, 1H), 4.49 (dd, J=14.7, 5.6, 1H), 4.12 (dd, J=14.7, 8.8, 1H), 3.51 (s, 3H), 2.59-2.45 (m, 1H), 2.10-1.95 (m, 2H), 1.92-1.79 (m, 3H), 1.80-1.68 (m, 2H), 1.69-1.57 (m, 3H), 1.30-1.24 (m, 2H), 1.15 (d, J=6.5, 3H), 1.14-0.96 (m, 2H), 0.91-0.84 (m, 1H), 0.83 (d, J=6.6, 3H), 0.74 (ddd, J=25.2, 13.0, 3.5, 1H).

Example 1.4: 6-{[(1R)-1-cyclobutylethyl]amino}-N-(dimethylsulfamoyl)-7-[(trans-4-methylcyclohexyl)methyl]-7H-purine-2-carboxamide

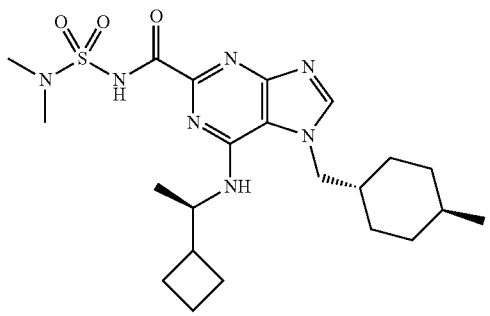

Step 1: To a suspension of 6-{[(1R)-1-cyclobutylethyl]amino}-7-[(trans-4-methylcyclohexyl)methyl]-7H-purine-2-carbonitrile (100 mg, 0.284 mmol, Preparative Example 1.2) in EtOH (1.4 mL) was added 5N NaOH (1.1 mL, 5.67 mmol). The reaction was stirred vigorously at 70° C. for 2 hours and then cooled to room temperature and quenched with 1N HCl. The mixture was diluted with EtOAc and washed with saturated aqueous sodium bicarbonate, water, and brine. The organic layer was dried over Na$_2$SO$_4$, filtered, and concentrated to afford crude 6-{[(1R)-1-cyclobutylethyl]amino}-7-[(trans-4-methylcyclohexyl)methyl]-7H-purine-2-carboxylic acid. MS ESI calc'd. for C$_{20}$H$_{29}$N$_5$O$_2$ [M+H]⁺ 372, found 372. This material was taken on to Step 2 without further purification.

Step 2: DMAP (13.42 mg, 0.110 mmol), EDC (21.05 mg, 0.110 mmol) and N,N-dimethylsulfamide (17.05 mg, 0.137 mmol) were added to a stirring solution of 6-{[(1R)-1-cyclobutylethyl]amino}-7-[(trans-4-methylcyclohexyl)methyl]-7H-purine-2-carboxylic acid (34.0 mg, 0.092 mmol) in DCM (458 µL) and the reaction was stirred at ambient temperature overnight. The reaction was diluted with DCM and the organics were washed with water, 2N aq. HCl, and brine. The organic layer was dried over Na$_2$SO$_4$, filtered, and concentrated. Purification of the residue by mass triggered reverse phase HPLC (C-18), eluting with acetonitrile/water containing 0.1% TFA afforded 6-{[(1R)-1-cyclobutylethyl]amino}-N-(dimethylsulfamoyl)-7-[(trans-4-methylcyclohexyl)methyl]-7H-purine-2-carboxamide (TFA salt). MS ESI calc'd. for C$_{22}$H$_{35}$N$_7$O$_3$S [M+H]⁺ 478, found 478. $^1$H NMR (600 MHz, CD$_3$OD) δ 8.43 (s, 1H), 4.77-4.64 (m, 1H), 4.54 (dd, J=14.7, 5.8, 1H), 4.23 (dd, J=14.7, 8.5, 1H), 3.00 (s, 6H), 2.63-2.51 (m, 1H), 2.16-2.06 (m, 1H), 2.06-1.97 (m, 1H), 1.96-1.81 (m, 4H), 1.75-1.68 (m, 1H), 1.68-1.59 (m, 3H), 1.34-1.28 (m, 2H), 1.20 (d, J=6.5, 3H), 1.16-0.97 (m, 2H), 0.92-0.84 (m, 1H), 0.83 (d, J=6.6, 3H), 0.76 (ddd, J=25.3, 13.1, 3.6, 1H).

Preparative Example 1.3: 6-chloro-7-((trans-4-methylcyclohexyl)methyl)-7H-purine-2-carbonitrile

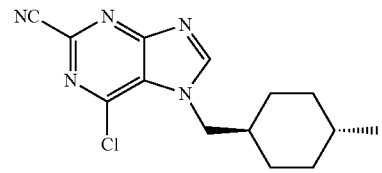 [SMILES: C[C@H]1CC[C@H](Cn2cnc3nc(C#N)nc(Cl)c32)CC1]

Step 1: The mixture of 2,6-dichloro-7-((trans-4-methylcyclohexyl)methyl)-7H-purine (5 g, 16.71 mmol, product of step 4, Preparative Example 1.2), (2,4-dimethoxyphenyl)methanamine (2643 µl, 17.55 mmol), and DIEA (17.5 mL, 100 mmol) in 2-propanol (28 mL) in a flask equipped with a reflux condenser was heated at 85° C. for 2 h. The reaction mixture was then cooled to ambient temperature and the solvent volume was reduced to 15 mL under reduced pressure. Next, water was added while stirring, and the precipitate that formed was collected by filtration to give 2-chloro-N-(2,4-dimethoxybenzyl)-7-((trans-4-methylcyclohexyl)methyl)-7H-purin-6-amine as an off-white solid. MS ESI calc'd. for C$_{22}$H$_{29}$C$_1$N$_5$O$_2$ [M+H]⁺ 430.2, found 430.2.

Step 2: Allyl palladium chloride dimer (0.340 g, 0.930 mmol) and 2-(dicyclohexylphosphino)-2',4',6'-triisopropylbiphenyl (1.552 g, 3.26 mmol) were combined in a flask and purged with N$_2$ (3×). To this was added degassed DMA (56.0 ml) and the suspension was heated at 50° C. for 30 minutes. 2-Chloro-N-(2,4-dimethoxybenzyl)-7-((trans-4-methylcyclohexyl)methyl)-7H-purin-6-amine (8 g, 18.61 mmol) and zinc cyanide (2.84 g, 24.19 mmol) were added and the suspension was purged with N$_2$ (3×). The reaction mixture was heated at 120° C. for 2 h, cooled to room temperature and purified by silica gel chromatography to afford an off white solid. The material was slurried in EtOAc/hexanes (1:4, 30 mL) and the solids were collected by filtration to afford 6-(2,4-dimethoxybenzyl)amino)-7-((trans-4-methylcyclohexyl)methyl)-7H-purine-2-carbonitrile.

Step 3: Trifluoroacetic acid (7.33 ml, 95 mmol) was added to neat 6-((2,4-dimethoxybenzyl)amino)-7-((trans-4-methylcyclohexyl)methyl)-7H-purine-2-carbonitrile (4.0 g, 9.51 mmol) and the reaction was stirred at room temperature for 6 hours. The reaction was then diluted with EtOAc (100 mL) and NaHCO$_3$ (sat'd aqueous, 40 mL) was slowly added. The mixture was stirred for 1 hour and then more NaHCO$_3$ was added until the aqueous layer had a basic pH. The mixture was extracted with EtOAc (2×60 mL). The organic layer was treated with hexanes (50 mL). The mixture was filtered and filter cake was washed with hexanes to afford crude 6-amino-7-((trans-4-methylcyclohexyl)methyl)-7H-purine-2-carbonitrile.

Step 4: To a solution of crude 6-amino-7-((trans-4-methylcyclohexyl)methyl)-7H-purine-2-carbonitrile (2.6 g, 9.62 mmol) in dry acetonitrile (26.0 ml) was added magnesium sulfate (0.116 g, 0.962 mmol) and cupric chloride (1.940 g, 14.43 mmol). tert-Butyl nitrite (2.024 ml, 17.31 mmol) was added dropwise at room temperature and the reaction was heated to 70° C. for 1 h. The reaction mixture was cooled to room temperature and filtered through Celite, washing the celite pad with EtOAc. The organic layer was washed with saturated sodium thiosulfate solution (20 mL). The aqueous layer was then extracted with EtOAc (3×50 mL) and dichloromethane (2×40 mL). The combined organic layers was dried over Na$_2$SO$_4$ and concentrated. The residue was purified by silica gel chromatography to afford 6-chloro-7-((trans-4-methylcyclohexyl)methyl)-7H-purine-2-carbonitrile. MS ESI calc'd. for C$_{14}$H$_{16}$C$_1$N$_5$ [M+H]+ 290, found 290.

Preparative Example 1.4: 3-(6-chloro-7-((trans-4-methylcyclohexyl)methyl)-7H-purin-2-yl)-1,2,4-oxadiazol-5(4H)-one

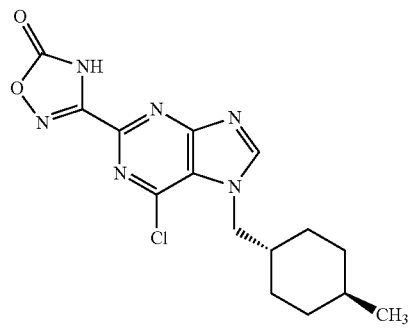 [SMILES: C[C@H]1CC[C@H](Cn2cnc3nc(-c4noc(=O)[nH]4)nc(Cl)c32)CC1]

Step 1: To a reaction vessel was added hydroxylamine HCl (71.9 mg, 1.035 mmol), and sodium bicarbonate (130 mg, 1.553 mmol) dissolved in water (1.55 mL). The vented reaction was allowed to stir for 15 minutes. Next was added 6-chloro-7-((trans-4-methylcyclohexyl)methyl)-7H-purine-2-carbonitrile (150 mg, 0.518 mmol, Preparative Example 1.3) suspended in ethanol (3.6 mL). The reaction mixture was stirred at room temperature for 1 hour. The reaction mixture was diluted with water and was extracted with DCM. The organics were collected, dried over magnesium sulfate and concentrated under reduced pressure to afford 6-chloro-N'-hydroxy-7-((trans-4-methylcyclohexyl)methyl)-7H-purine-2-carboximidamide as a crude residue. MS ESI calc'd. for C$_{14}$H$_{19}$C$_1$N$_6$O [M+H]$^+$ 323, found 323.

Step 2: To a reaction vessel was added 6-chloro-N'-hydroxy-7-((trans-4-methylcyclohexyl)methyl)-7H-purine-2-carboximidamide (1.67 g, 5.17 mmol) as a crude residue, 1,1'-carbonyldiimidazole (1.007 g, 6.21 mmol) and DBU (0.39 mL, 2.59 mmol) suspended in acetonitrile (16.7 mL). The reaction vessel was sealed and allowed to stir for 2 hours at ambient temperature. The reaction mixture was diluted with DCM and washed with 1M HCl (2×) and brine (1×). The organic layer was dried over Na$_2$SO$_4$ and concentrated. The crude residue was purified by silica gel chromatography (0 to 10% MeOH/DCM) to afford 3-(6-chloro-7-((trans-4-methylcyclohexyl)methyl)-7H-purin-2-yl)-1,2,4-oxadiazol-5(4H)-one. MS ESI calc'd. for C$_{15}$H$_{17}$C$_1$N$_6$O$_2$ [M+H]$^+$ 349, found 349.

Example 1.5: 3-{6-(3-chlorophenoxy)-7-[(trans-4-methylcyclohexyl)methyl]-7H-purin-2-yl}-1,2,4-oxadiazol-5(4H)-one

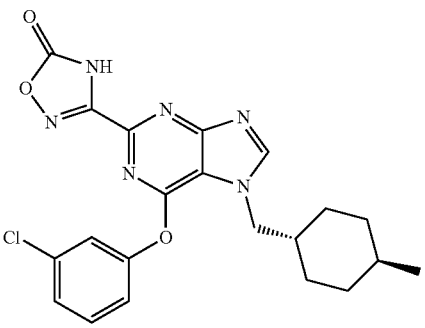 [SMILES: C[C@H]1CC[C@H](Cn2cnc3nc(-c4noc(=O)[nH]4)nc(Oc4cccc(Cl)c4)c32)CC1]

To a sealable reaction vessel was added 3-(6-chloro-7-((trans-4-methylcyclohexyl)methyl)-7H-purin-2-yl)-1,2,4-oxadiazol-5(4H)-one (0.020 g, 0.057 mmol, Preparative Example 1.4), (3-chlorophenyl)boronic acid (0.018 g, 0.12 mmol), PdCl$_2$(dppf)-CH$_2$Cl$_2$ adduct (0.0094 g, 0.011 mmol), tripotassium phosphate (0.048 g, 0.23 mmol), dioxane (1.0 mL) and water (0.25 mL). The reaction vessel was sealed and heated to 100° C. for 4 hours. The completed reaction was diluted with water and extracted with DCM. The organics were collected, dried over magnesium sulfate, filtered and concentrated under reduced pressure. The residue was taken up in DMSO (1.0 mL), passed through a syringe filter and purified by reverse phase preparative HPLC (0:100 to 95:5 acetonitrile:water: 0.1% v/v TFA modifier) to afford 3-{6-(3-chlorophenoxy)-7-[(trans-4-methylcyclohexyl)methyl]-7H-purin-2-yl}-1,2,4-oxadiazol-5(4H)-one (TFA salt). MS ESI calc'd. for C$_{21}$H$_{21}$C$_1$N$_6$O$_3$ [M+H]$^+$ 441, found 441. $^1$H NMR (500 MHz, dmso) δ 13.21 (s, 1H), 8.80 (s, 1H), 7.58 (m, 1H), 7.53 (t, J=8.1, 1H), 7.41 (m, 2H), 4.31 (d, J=7.1, 2H), 1.85 (m, 1H), 1.62 (d, 2H), 1.53 (d, 2H), 1.27 (m, 1H), 1.04 (m, 2H), 0.81 (m, 5H).

Example 1.6: 3-{6-(3,3-difluoropiperidin-1-yl)-7-[(trans-4-methylcyclohexyl)methyl]-7H-purin-2-yl}-1,2,4-oxadiazol-5(4H)-one

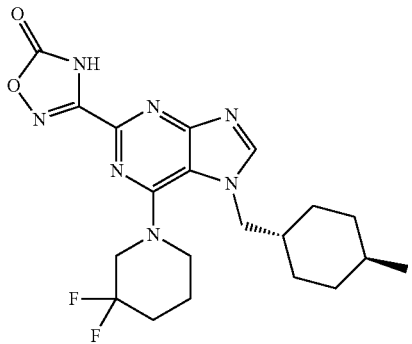 [SMILES: C[C@H]1CC[C@H](Cn2cnc3nc(-c4noc(=O)[nH]4)nc(N4CCCC(F)(F)C4)c32)CC1]

To a sealable tube was added 3-(6-chloro-7-((trans-4-methylcyclohexyl)methyl)-7H-purin-2-yl)-1,2,4-oxadiazol-5(4H)-one (0.020 g, 0.057 mmol, Preparative Example 1.4), 3,3-difluoropiperidine (0.020 g, 0.13 mmol), TEA (0.050 mL, 0.36 mmol), and DMSO (1.0 mL, 0.057 M). The reaction tube was sealed and heated to 100° C. for 12 hours. The reaction was cooled and passed through a syringe filter. The filtrate was purified by reverse phase preparative HPLC (0:100 to 95:5 acetonitrile:water: 0.1% v/v TFA modifier) to afford 3-{6-(3,3-difluoropiperidin-1-yl)-7-[(trans-4-methylcyclohexyl)methyl]-7H-purin-2-yl}-1,2,4-oxadiazol-5(4H)-one. MS ESI calc'd. for $C_{20}H_{25}F_2N_7O_2$ [M+H]$^+$ 434, found 434. 1H NMR (500 MHz, DMSO-$d_6$) δ 13.05 (s, 1H), 8.70 (s, 1H), 4.16 (d, J=7.6, 2H), 3.72 (t, J=11.4, 2H), 3.39 (m, 2H), 2.15 (m, 2H), 1.91 (m, 2H), 1.71 (m, 1H), 1.56 (d, J=10.8, 2H), 1.17 (d, J=11.3, 3H), 0.89 (m, 2H), 0.77 (d, J=6.5, 3H), 0.70 (m, 2H).

Example 1.7: 3-(6-{[(1R)-1-cyclobutylethyl]amino}-7-[(trans-4-methylcyclohexyl)methyl]-7H-purin-2-yl)-1,2,4-oxadiazol-5(4H)-one

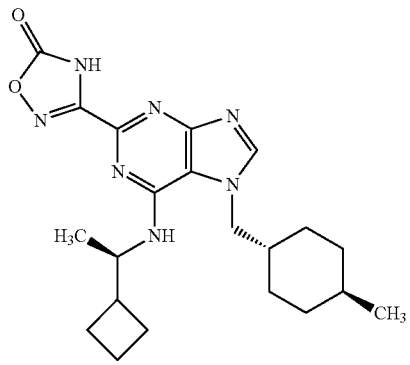 [SMILES: C[C@@H](Nc1nc(-c2noc(=O)[nH]2)nc2ncn(C[C@H]3CC[C@H](C)CC3)c12)C1CCC1]

Step 1: Using a procedure similar to that described in Preparative Example 1.4 (Step 1, the difference being that the reaction mixture was heated at 100° C. for 1 h, instead of at room temperature), and starting with Preparative Example 1.2, 6-[[(1R)-1-cyclobutylethyl]amino]-7-[(trans-4-methylcyclohexyl)methyl]-7H-purine-2-carbonitrile, 6-(((R)-1-cyclobutylethyl)amino)-N'-hydroxy-7-((trans-4-methylcyclohexyl)methyl)-7H-purine-2-carboximidamide was prepared.

Step 2: Using a procedure analogous to that described in Preparative Example 1.4 (Step 2), and starting with 6-(((R)-1-cyclobutylethyl)amino)-N'-hydroxy-7-((trans-4-methylcyclohexyl)methyl)-7H-purine-2-carboximidamide, 3-(6-{[(1R)-1-cyclobutylethyl]amino}-7-[(trans-4-methylcyclohexyl)methyl]-7H-purin-2-yl)-1,2,4-oxadiazol-5(4H)-one was prepared. $^1$H NMR (400 MHz, CD$_3$OD) δ 8.24 (s, 1H), 4.69 (m, 1H), 4.51 (dd, J=6.0, 5.6 Hz, 1H), 4.18 (dd, J=14.8, 8.4 Hz, 1H), 2.56 (m, 1H), 2.02-2.12 (m, 2H), 1.85-1.96 (m, 3H), 1.66-1.73 (m, 3H), 1.28-1.33 (m, 3H), 1.02-1.21 (m, 5H), 0.77-0.90 (m, 6H). MS (ES)=412 (M+1)$^+$.

Preparative Example 1.5: (R)-1-cyclobutylethanamine hydrochloride

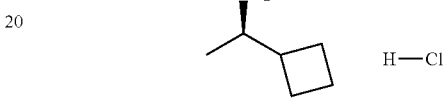

Step 1: Into a 20-L 4-necked round-bottom flask was placed a solution of cyclobutylmethanol (1000 g, 11.61 mol) in dichloromethane (10 L). This was followed by the addition of Dess-Martin periodinane (4683 g, 11.04 mol) in several batches at 10-15° C. over 120 min. The resulting solution was stirred for 2 h at room temperature and then quenched by the addition of 20 L of cold, saturated aqueous sodium bicarbonate solution. Solids were removed by filtration and washed with 5 L of dichloromethane. The filtrate was extracted with dichloromethane. The organic layers were combined, dried over anhydrous sodium sulfate and concentrated under vacuum. The residue was applied onto a silica gel column and eluted with DCM:PE (2:1). This resulted in 100 L of cyclobutanecarbaldehyde in dichloromethane and petroleum ether solution.

Step 2: Into a 50-L barrel was placed cyclobutanecarbaldehyde in dichloromethane and petroleum ether (33 L of the solution described at the end of Step 1), (S)-2-methylpropane-2-sulfinamide (500 g, 4.13 mol) and copper sulfate (2 kg, 13.33 mol). The resulting solution was stirred for 2 days at room temperature. Solids were removed by filtration. The filtrate was concentrated under vacuum. The residue was applied onto a silica gel column and eluted with ethyl acetate/petroleum ether (1:5) to afford (S)—N-[(1E)-cyclobutylmethylidene]-2-methylpropane-2-sulfinamide.

Step 3: Into a 10-L 4-neck round-bottom flask purged and maintained with an inert atmosphere of nitrogen was placed a solution of (S)—N-[(1E)-cyclobutylmethylidene]-2-methylpropane-2-sulfinamide (200 g, 1.07 mol) in tetrahydrofuran (3000 mL). This was followed by the addition of methylmagnesium bromide in ether (1070 mL, 3.00 equiv) dropwise with stirring at −78° C. over 1 hr. The resulting solution was stirred for 1 h at −70° C., 1 h at −60° C., 1 h at −50° C. and 2 h at −40° C. The reaction was then quenched by the addition of 10 L of saturated aqueous NH$_4$Cl solution. The resulting solution was extracted with 2×3 L of ether. The organic layers were combined, washed with 2×3 L of brine, dried over anhydrous sodium sulfate, and concentrated under vacuum. The residue was diluted with 250 mL of n-hexane. The resulting solid was collected and washed with 2×100 mL of cold n-hexane to afford (S)—N-[(1R)-1-cyclobutylethyl]-2-methylpropane-2-sulfinamide.

Step 4: Into a 10-L 4-neck round-bottom flask was placed a solution of (S)—N-[(1R)-1-cyclobutylethyl]-2-methylpropane-2-sulfinamide (400 g, 1.97 mol) in methanol (2800 mL). This was followed by the addition of HCl/p-dioxane (5M, 1.6 L) dropwise with stirring at 0° C. over 60 min. The resulting solution was stirred for 60 min at room temperature. The solution was then concentrated under vacuum. The residue was diluted with 4 L of n-hexane and stirred for 30 min at room temperature. The solid was collected by filtration. The filtrate was diluted with 1200 mL of CH$_3$CN and stirred for 30 min at room temperature. The solid was collected by filtration. The combined solids were dried in an oven under reduced pressure to afford (1R)-1-cyclobutylethan-1-amine as a hydrogen chloride salt. MS ESI calc'd for C$_6$H$_{13}$N [M+H]$^+$ 100, found 100. $^1$H NMR (400 MHz, DMSO-d$_6$): δ 7.95 (s, 3H), 3.11 (s, 1H), 2.32-2.42 (m, 1H), 1.75-2.01 (m, 6H), 1.10 (s, 3H).

Example 1.15: 5-(6-{[(1R)-1-cyclobutylethyl]amino}-7-[(trans-4-methylcyclohexyl)methyl]-7H-purin-2-yl)-1,3,4-oxadiazol-2(3H)-one

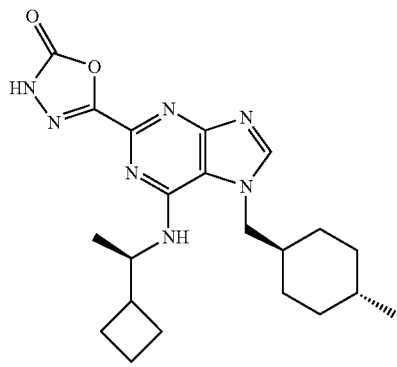 [SMILES: C[C@@H](Nc1nc(-c2n[nH]c(=O)o2)nc2ncn(C[C@H]3CC[C@H](C)CC3)c12)C1CCC1]

Step 1: Oxalyl chloride (0.1 mL, 0.67 mmol) was added dropwise to a 0° C. solution of 6-{[(1R)-1-cyclobutylethyl]amino}-7-[(trans-4-methylcyclohexyl)methyl]-7H-purine-2-carboxylic acid (Example 1.2; 50 mg, 0.13 mmol) in dichloromethane (1 mL). The reaction was warmed to room temperature and stirred for 1 hour under a nitrogen atmosphere. The reaction was then concentrated under a nitrogen atmosphere and dissolved in THF (0.7 mL). This solution was added dropwise to a flask containing a 0° C. solution of hydrazine (1 M in THF; 1.2 mL, 1.2 mmol) and the reaction was then warmed to room temperature and stirred for 1 hour at room temperature under a nitrogen atmosphere. Next, the reaction was concentrated and water (1.5 mL) was added. The mixture was extracted with ethyl acetate (2×2 mL). The combined organic extracts were washed with brine (2 mL), dried over anhydrous Na$_2$SO$_4$, filtered, and concentrated to afford 6-(((R)-1-cyclobutylethyl)amino)-7-(((trans)-4-methylcyclohexyl)methyl)-7H-purine-2-carbohydrazide. MS (ES)=386 (M+1)$^+$.

Step 2: To a solution of 6-(((R)-1-cyclobutylethyl)amino)-7-(((trans)-4-methylcyclohexyl)methyl)-7H-purine-2-carbohydrazide (50 mg, 0.12 mmol) and 1,1'-carbonyldiimidazole (31 mg, 0.19 mmol) in acetonitrile (1 mL) was added DBU (78 mg, 0.51 mmol) dropwise. The reaction mixture was stirred at room temperature for 2 hours. The reaction was then concentrated and the residue was diluted with CH$_2$Cl$_2$ (40 mL) and washed with water (40 mL). The organic layer was dried over anhydrous Na$_2$SO$_4$ and concentrated. The residue was purified on a silica gel column (0 to 100% EtOAc/hexanes) to afford 5-(6-{[(1R)-1-cyclobutylethyl]amino}-7-[(trans-4-methylcyclohexyl)methyl]-7H-purin-2-yl)-1,3,4-oxadiazol-2(3H)-one. $^1$H NMR (400 MHz, CD$_3$OD) δ 8.32 (s, 1H), 4.49-4.64 (m, 2H), 4.20 (m, 1H), 2.60 (m, 1H), 2.00-2.20 (m, 2H), 1.87-2.00 (m, 4H), 1.60-1.89 (m, 5H), 1.28-1.1.40 (m, 3H), 1.34 (d, J=6.8 Hz, 3H), 1.00-1.15 (m, 2H), 0.86 (d, J=6.4 Hz, 3H). MS (ESI)=412 (M+1)$^+$.

Example 1.16: 5-(6-{[(1R)-1-cyclobutylethyl]amino}-7-[(trans-4-methylcyclohexyl)methyl]-7H-purin-2-yl)-4-methyl-2,4-dihydro-3H-1,2,4-triazol-3-one

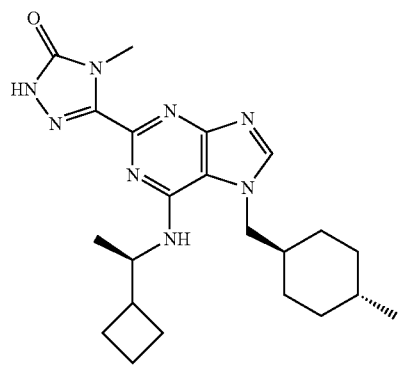 [SMILES: C[C@@H](Nc1nc(-c2n[nH]c(=O)n2C)nc2ncn(C[C@H]3CC[C@H](C)CC3)c12)C1CCC1]

Step 1: To a mixture 6-(((R)-1-cyclobutylethyl)amino)-7-4(trans)-4-methylcyclohexyl)methyl)-7H-purine-2-carbohydrazide (Example 1.15, Step 1; 70 mg, 0.18 mmol) in dichloromethane (2.0 mL) was added 4-nitrophenyl methylcarbamate (*Tet. Lett;* 2006, 47, 3405-3407) (53 mg, 0.27 mmol) and DIPEA (30 mg, 0.23 mmol). The reaction was stirred for 16 hours at room temperature under a nitrogen atmosphere and then concentrated under reduced pressure. Hexane was added to the residue and the resulting solid was collected by filtration to afford crude of 2-(6-(((R)-1-cyclobutylethyl)amino)-7-(((trans)-4-methylcyclohexyl)methyl)-7H-purine-2-carbonyl)-N-methylhydrazinecarboxamide. MS (ES)=443 (M+1)$^+$.

Step 2: Aqueous NaOH (5 N, 0.12 mL, 0.60 mmol) was added to 2-(6-(((R)-1-cyclobutylethyl)amino)-7-(((trans)-4-methylcyclohexyl)methyl)-7H-purine-2-carbonyl)-N-methylhydrazinecarboxamide (55 mg, 0.12 mmol) and the reaction was heated at 100° C. for 2 hours under a nitrogen atmosphere. Then reaction was then cooled to 0° C., neutralized with aqueous 1 N HCl, and extracted with ethyl acetate (2×5 mL). The combined organic extracts were washed with brine (5 mL), dried over anhydrous Na$_2$SO$_4$, filtered, and concentrated. Purification of the residue on a Biotage C$_{18}$ column (0 to 100% water/acetonitrile) afforded 5-(6-{[(1R)-1-cyclobutylethyl]amino}-7-[(trans-4-methylcyclohexyl)methyl]-7H-purin-2-yl)-4-methyl-2,4-dihydro-3H-1,2,4-triazol-3-one. $^1$H NMR (400 MHz, CD$_3$OD) δ 8.21 (s, 1H), 4.50-4.61 (m, 2H), 4.16 (dd, J=14.8, 8.8 Hz, 1H), 3.72 (s, 3H), 2.57 (m, 1H), 2.01-2.20 (m, 2H), 1.85-1.95 (m, 4H), 1.67-1.76 (m, 4H), 1.29-1.42 (m, 2H), 0.99-1.34 (m, 5H), 0.74-0.87 (m, 5H). MS (ES)=425 (M+1)$^+$.

Examples in Table 1 were described above or were prepared using procedures similar to those described above.

TABLE 1

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.1 | 1137 | 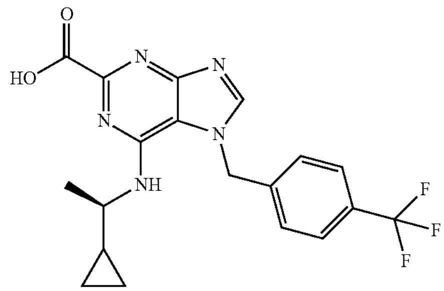 [SMILES: C[C@@H](Nc1nc(C(=O)O)nc2ncn(Cc3ccc(C(F)(F)F)cc3)c12)C1CC1] | 6-{[(1R)-1-cyclopropylethyl]amino}-7-[4-(trifluoromethyl)benzyl]-7H-purine-2-carboxylic acid | TFA | 406 | 406 |
| 1.2 | 68.5 | 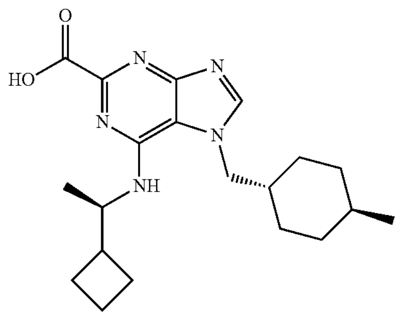 [SMILES: C[C@@H](Nc1nc(C(=O)O)nc2ncn(C[C@H]3CC[C@H](C)CC3)c12)C1CCC1] | 6-{[(1R)-1-cyclobutylethyl]amino}-7-[(trans-4-methylcyclohexyl)methyl]-7H-purine-2-carboxylic acid | TFA | 372 | 372 |
| 1.3 | 71.13 | 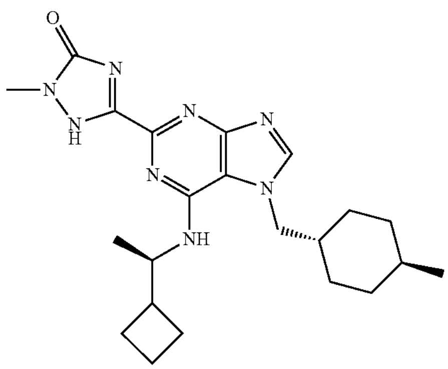 | 5-(6-{[(1R)-1-cyclobutylethyl]amino}-7-[(trans-4-methylcyclohexyl)methyl]-7H-purin-2-yl)-2-methyl-1,2-dihydro-3H-1,2,4-triazol-3-one | | 425 | 425 |
| 1.4 | 733.2 | 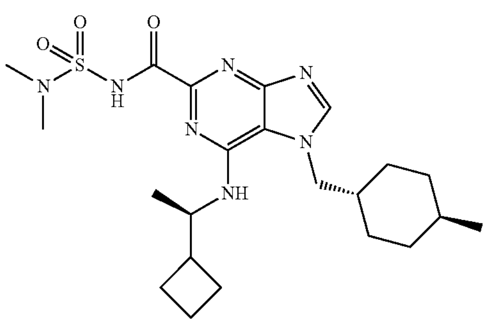 | 6-{[(1R)-1-cyclobutylethyl]amino}-N-(dimethylsulfamoyl)-7-[(trans-4-(methylcyclohexyl)methyl]-7H-purine-2-carboxamide | TFA | 478 | 478 |
| 1.5 | 391.6 | 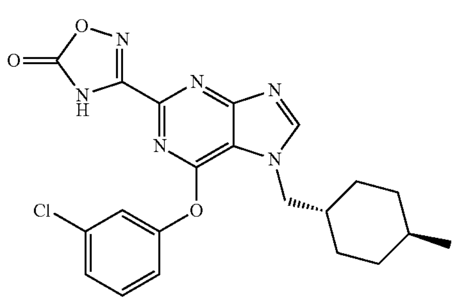 [SMILES: C[C@H]1CC[C@H](Cn2cnc3nc(-c4noc(=O)[nH]4)nc(Oc4cccc(Cl)c4)c32)CC1] | 3-{6-(3-chlorophenoxy)-7-[(trans-4-methylcyclohexyl)methyl]-7H-purin-2-yl}-1,2,4-oxadiazol-5(4H)-one | TFA | 441 | 441 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.6 | 820 | 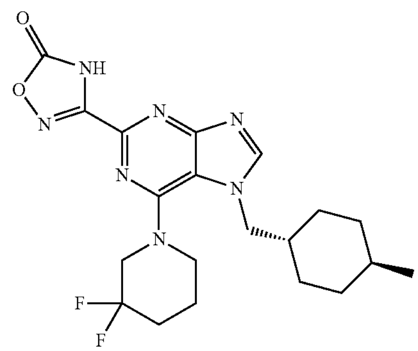 [SMILES: C[C@H]1CC[C@H](Cn2cnc3nc(-c4noc(=O)[nH]4)nc(N4CCCC(F)(F)C4)c32)CC1] | 3-{6-(3,3-difluoropiperidin-1-yl)-7-[(trans-4-methylcyclohexyl)methyl]-7H-purin-2-yl}-1,2,4-oxadiazol-5(4H)-one | TFA | 434 | 434 |
| 1.7 | 51.27 | 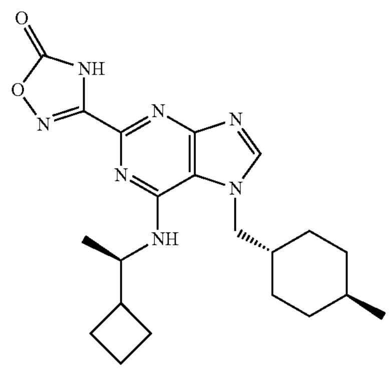 [SMILES: C[C@@H](Nc1nc(-c2noc(=O)[nH]2)nc2ncn(C[C@H]3CC[C@H](C)CC3)c12)C1CCC1] | 3-(6-{[(1R)-1-cyclobutylethyl]amino}-7-[(trans-4-methylcyclohexyl)methyl]-7H-purin-2-yl)-1,2,4-oxadiazol-5(4H)-one | | 412 | 412 |
| 1.8 | 2416 | 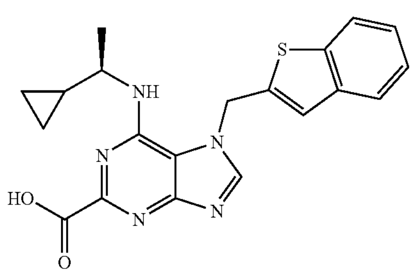 [SMILES: C[C@@H](Nc1nc(C(=O)O)nc2ncn(Cc3cc4ccccc4s3)c12)C1CC1] | 7-(1-benzothiophen-2-ylmethyl)-6-{[(1R)-1-cyclopropylethyl]amino}-7H-purine-2-carboxylic acid | | 394 | 394 |
| 1.9 | 39% inhibition at 1000 nM | 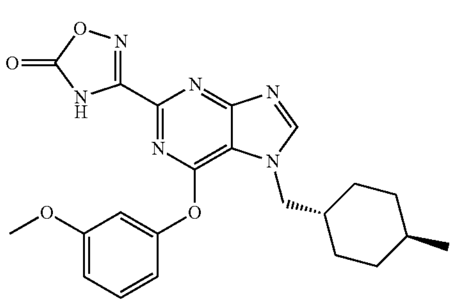 | 3-{6-(3-methoxyphenoxy)-7-[(trans-4-methylcyclohexyl)methyl]-7H-purin-2-yl}-1,2,4-oxadiazol-5(4H)-one | TFA | 437 | 437 |

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.10 | 37% inhibition at 1000 nM | 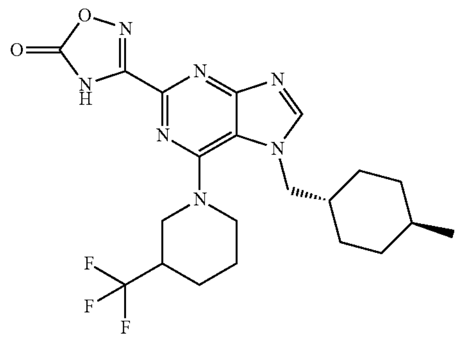 [SMILES: C[C@H]1CC[C@H](Cn2cnc3nc(-c4noc(=O)[nH]4)nc(N4CCCC(C(F)(F)F)C4)c32)CC1] | 3-{7-[(trans-4-methylcyclohexyl)methyl]-6-[3-(trifluoromethyl)piperidin-1-yl]-7H-purin-2-yl}-1,2,4-oxadiazol-5(4H)-one | TFA | 466 | 466 |
| 1.11 | 43% inhibition at 1000 nM | 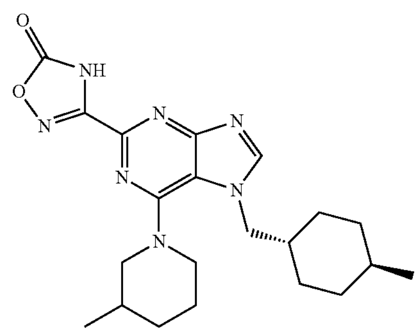 [SMILES: CC1CCCN(c2nc(-c3noc(=O)[nH]3)nc3ncn(C[C@H]4CC[C@H](C)CC4)c23)C1] | 3-{7-[(trans-4-methylcyclohexyl)methyl]-6-(3-methylpiperidin-1-yl)-7H-purin-2-yl}-1,2,4-oxadiazol-5(4H)-one | TFA | 412 | 412 |
| 1.12 | 43% inhibition at 1000 nM | 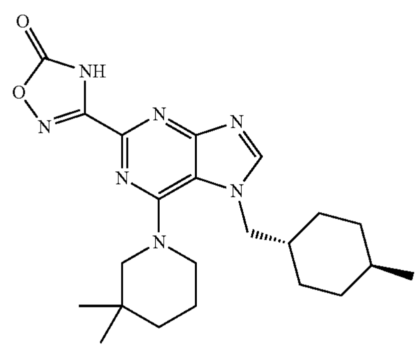 [SMILES: CC1(C)CCCN(c2nc(-c3noc(=O)[nH]3)nc3ncn(C[C@H]4CC[C@H](C)CC4)c23)C1] | 3-{6-(3,3-dimethylpiperidin-1-yl)-7-[(trans-4-methylcyclohexyl)methyl]-7H-purin-2-yl}-1,2,4-oxadiazol-5(4H)-one | TFA | 426 | 426 |
| 1.13 | 81.61 | 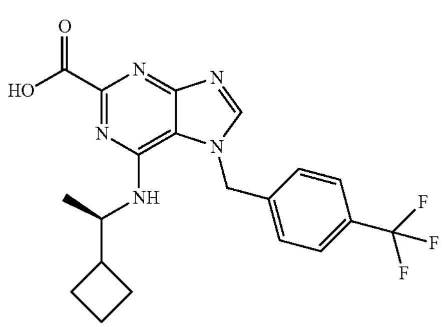 [SMILES: C[C@@H](Nc1nc(C(=O)O)nc2ncn(Cc3ccc(C(F)(F)F)cc3)c12)C1CCC1] | 6-{[(1R)-1-cyclobutylethyl]amino}-7-[4-(trifluoromethyl)benzyl]-7H-purine-2-carboxylic acid | TFA | 420 | 420 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.14 | 21.58 | 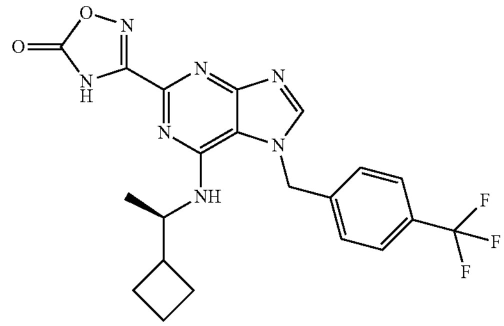 [SMILES: C[C@@H](Nc1nc(-c2noc(=O)[nH]2)nc2ncn(Cc3ccc(C(F)(F)F)cc3)c12)C1CCC1] | 3-(6-{[(1R)-1-cyclobutylethyl]amino}-7-[4-(trifluoromethyl)benzyl]-7H-purin-2-yl)-1,2,4-oxadiazol-5(4H)-one | TFA | 460 | 460 |
| 1.15 | 52.52 | 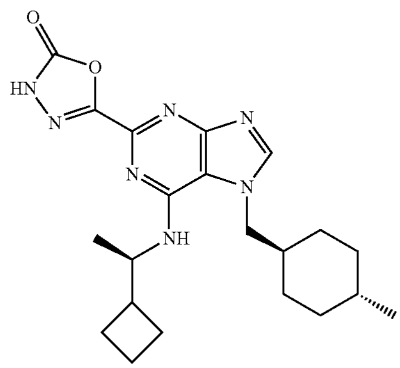 [SMILES: C[C@@H](Nc1nc(-c2n[nH]c(=O)o2)nc2ncn(C[C@H]3CC[C@H](C)CC3)c12)C1CCC1] | 5-(6-{[(1R)-1-cyclobutylethyl]amino}-7-[(trans-4-methylcyclohexyl)methyl]-7H-purin-2-yl)-1,3,4-oxadiazol-2(3H)-one | | 412 | 412 |
| 1.16 | 241.2 | 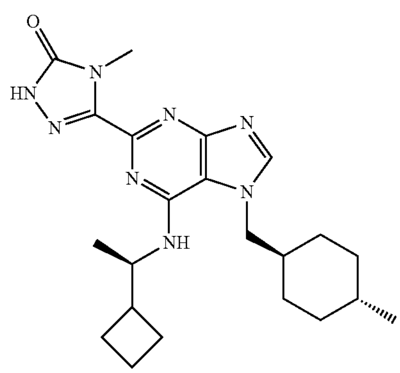 [SMILES: C[C@@H](Nc1nc(-c2n[nH]c(=O)n2C)nc2ncn(C[C@H]3CC[C@H](C)CC3)c12)C1CCC1] | 5-(6-{[(1R)-1-cyclobutylethyl]amino}-7-[(trans-4-methylcyclohexyl)methyl]-7H-purin-2-yl)-4-methyl-2,4-dihydro-3H-1,2,4-triazol-3-one | | 425 | 425 |

Preparative Example 2.1: 6-(3-chlorophenyl)-7-((trans-4-methylcyclohexyl)methyl)-7H-purine-2-carbonitrile

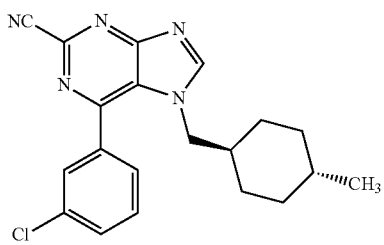 [SMILES: C[C@H]1CC[C@H](Cn2cnc3nc(C#N)nc(-c4cccc(Cl)c4)c32)CC1]

Step 1: 2,6-dichloro-7-(((trans)-4-methylcyclohexyl)methyl)-7H-purine (500 mg, 1.7 mmol, Preparative Example 1.2, product of Step 4), 3-chlorophenyl boronic acid (288 mg, 1.8 mmol0, aqueous Na$_2$CO$_3$ (0.5 mL, 1 M), and toluene (4.5 mL) were placed in a vial (25 mL) and the mixture was degassed using N$_2$ for 15 minutes before Pd(PPh$_3$)$_4$ (207 mg, 0.18 mmol) was added. The reaction vial was sealed and heated at 100° C. for 15 minutes. The reaction was then cooled to room temperature and extracted with EtOAc (2×25 mL). The combined organic layers were washed with water and brine, dried over anhydrous Na$_2$SO$_4$, filtered, and concentrated. The crude product was purified by silica gel chromatography with 0 to 10% EtOAc/hexanes to afford 2-chloro-6-(3-chlorophenyl)-7-(((trans)-4-methylcyclohexyl)methyl)-7H-purine. $^1$H NMR (300 MHz, CDCl$_3$): δ 8.16 (s, 1H), 7.48-7.60 (m, 4H), 3.80 (d, J=6.9 Hz, 2H), 1.08-1.29 (m, 3H), 0.87-1.08 (m, 4H), 0.80 (d, J=6.6 Hz, 3H), 0.56-0.75 (m, 3H). MS (APCI)=375 (M+1)$^+$.

Step 2: 2-chloro-6-(3-chlorophenyl)-7-(((trans)-4-methylcyclohexyl)methyl)-7H-purine (200 mg, 0.53 mmol) and zinc cyanide (31.2 mg, 0.26 mmol) were dissolved in DMA and degassed with argon for 20 minutes. Tetrakis(triphenylphosphine)palladium(0) (123 mg, 0.10 mmol) was then added and the mixture was degassed for another 5 minutes. The vial was sealed and heated at 120° C. for 4 hours. The reaction mixture was then cooled to room temperature, diluted with water (20 mL), and extracted with EtOAc (2×50 mL). The combined organic extracts were dried over anhydrous $Na_2SO_4$, filtered, and concentrated. The residue was purified on a silica gel column (0 to 10% EtOAc/Hexanes) to afford 6-(3-chlorophenyl)-7-(((trans)-4-methylcyclohexyl)methyl)-7H-purine-2-carbonitrile. $^1$H NMR (300 MHz, $CDCl_3$): δ 8.15 (s, 1H), 7.44-7.59 (m, 4H), 3.95 (d, J=6.9 Hz, 2H), 1.50-1.55 (m, 2H), 1.08-1.29 (m, 2H), 0.85-1.01 (m, 4H), 0.78 (d, J=6.6 Hz, 3H), 0.52-0.56 (m, 2H). MS (APCI)=366 (M+1)$^+$.

Example 2.1: 3-{6-(3-chlorophenyl)-7-[(trans-4-methylcyclohexyl)methyl]-7H-purin-2-yl}-1,2,4-oxadiazol-5(4H)-one

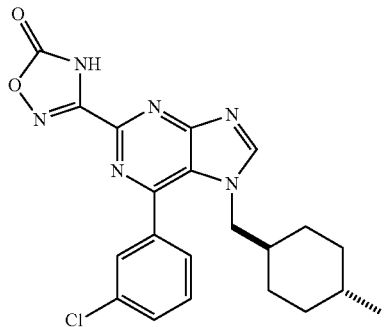

Step 1: Hydroxylamine hydrochloride (19.6 mg, 0.28 mmol), sodium bicarbonate (35.5 mg, 0.42 mmol), and water (0.42 mL) were combined in a vented vial and stirred for 15 minutes. This solution was then added to a vial containing 6-(3-chlorophenyl)-7-[(trans-4-methylcyclohexyl)methyl]-7H-purine-2-carbonitrile (51.6 mg, 0.14 mmol, Preparative Example 2.1) dissolved in ethanol (0.99 mL). The mixture was sealed and heated at 100° C. for 1 hour. The reaction was cooled to room temperature, diluted with water, and extracted with ethyl acetate (2×). The combined organic layers were dried over sodium sulfate, filtered, and concentrated to afford 6-(3-chlorophenyl)-N'-hydroxy-7-[(trans-4-methylcyclohexyl)methyl]-7H-purine-2-carboximidamide. MS ESI calc'd. for $C_{20}H_{23}C_1N_6O$ [M+H]$^+$ 399, found 399.

Step 2: To a solution of 6-(3-chlorophenyl)-N'-hydroxy-7-[(trans-4-methylcyclohexyl)methyl]-7H-purine-2-carboximidamide (55 mg, 0.138 mmol) and 1,1'-carbonyldiimidazole (24.6 mg, 0.15 mmol) dissolved in acetonitrile (1.4 mL) was added 1,8-diazabicyclo[5.4.0]undec-7-ene (0.082 mL, 0.55 mmol). The reaction mixture was stirred at room temperature for 1 hour. The reaction was then diluted with water and extracted with dichloromethane. The organic layer was dried over sodium sulfate, filtered, and concentrated under reduced pressure. The residue was dissolved in DMSO and purified by mass triggered, reverse phase (C-18) preparative HPLC (acetonitrile/water: 0.1% v/v trifluoroacetic acid modifier) to afford 3-{6-(3-chlorophenyl)-7-[(trans-4-methylcyclohexyl)methyl]-7H-purin-2-yl}-1,2,4-oxadiazol-5(4H)-one (as a TFA salt). MS ESI calc'd. for $C_{21}H_{21}C_1N_6O_2$ [M+H]$^+$ 425, found 425. $^1$H NMR (500 MHz, DMSO-$d_6$) δ 13.26 (s, 1H), 8.91 (s, 1H), 7.90 (s, 1H), 7.72 (d, J=8.1, 2H), 7.67-7.62 (m, 1H), 3.92 (d, J=6.4, 2H), 1.45 (d, J=12.3, 2H), 1.09 (broad, 1H), 0.89-0.82 (m, 3H), 0.76-0.71 (m, 5H), 0.53-0.38 (m, 2H).

Example 2.2: 3-{6-(2-chloro-3-fluoropyridin-4-yl)-7-[(trans-4-methylcyclohexyl)methyl]-7H-purin-2-yl}-1,2,4-oxadiazol-5(4H)-one

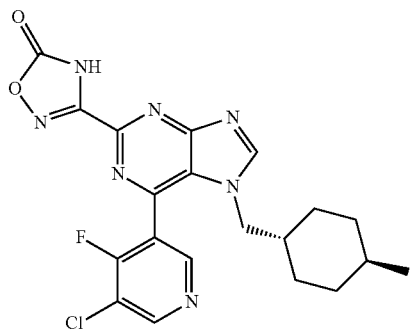 [SMILES: C[C@H]1CC[C@H](Cn2cnc3nc(-c4noc(=O)[nH]4)nc(-c4cncc(Cl)c4F)c32)CC1]

Step 1: To a sealed tube was added 6-chloro-7-((trans-4-methylcyclohexyl)methyl)-7H-purine-2-carbonitrile (0.030 g, 0.10 mmol, Preparative Example 1.3), $PdCl_2$(dppf)-$CH_2Cl_2$ adduct (0.025 g, 0.030 mmol), (2-chloro-3-fluoropyridin-4-yl)boronic acid (0.027 g, 0.016 mmol), $K_2CO_3$ (0.072 g, 0.52 mmol), and dioxane (1.0 mL). The reaction vessel was purged with argon, sealed, and heated at 100° C. for 12 hours. The completed reaction was diluted with DCM:MeOH (9:1, 1.0 mL) and loaded onto a 2 g silica gel SPE cartridge and eluted with DCM:MeOH (9:1, 20 mL). The organics were collected and concentrated under reduced pressure to afford 6-(2-chloro-3-fluoropyridin-4-yl)-7-((trans-4-methylcyclohexyl)methyl)-7H-purine-2-carbonitrile as a crude residue.

Step 2: To the crude residue of 6-(2-chloro-3-fluoropyridin-4-yl)-7-((trans-4-methylcyclohexyl)methyl)-7H-purine-2-carbonitrile (0.038 g, 0.10 mmol) was added EtOH (1.0 mL) and hydroxylamine (0.10 mL, 50% w/w solution in $H_2O$). The reaction was stirred at ambient temperature for 2 hours and then concentrated under reduced pressure to afford 6-(2-chloro-3-fluoropyridin-4-yl)-N-hydroxy-7-((trans-4-methylcyclohexyl)methyl)-7H-purine-2-carboximidamide as a crude residue.

Step 3: To the crude residue of 6-(2-chloro-3-fluoropyridin-4-yl)-N-hydroxy-7-((trans-4-methylcyclohexyl)methyl)-7H-purine-2-carboximidamide (0.042 g, 0.10 mmol), was added 1,1'-carbonyldiimidazole (0.024 g, 0.15 mmol), DBU (0.60 mL, 0.40 mmol), and acetonitrile (1.10 mL). The reaction vessel was sealed and allowed to stir for 5 hours at ambient temperature. The reaction was then diluted with water and was extracted with DCM. The organic layer was collected and concentrated under reduced pressure. The residue was purified by reverse phase preparative HPLC (0:100 to 95:5 acetonitrile:water: 0.1% v/v TFA modifier) to afford 3-{6-(2-chloro-3-fluoropyridin-4-yl)-7-[(trans-4-methylcyclohexyl)methyl]-7H-purin-2-yl}-1,2,4-oxadiazol-5(4H)-one. MS ESI calc'd. for $C_{20}H_{19}ClFN_7O_2$ [M+H]$^+$ 444, found 444. $^1$H NMR (600 MHz, DMSO) δ 8.98 (s, 1H), 8.58 (d, J=4.8, 1H), 7.91 (t, J=4.8, 1H), 3.80 (d, J=6.8, 2H), 1.49 (d, J=12.1, 2H), 1.11 (m, 1H), 0.92 (m, 3H), 0.75 (m, 6H), 0.52 (m, 2H).

Example 2.3: 3-{6-(4-chloropyridin-2-yl)-7-[(trans-4-methylcyclohexyl)methyl]-7H-purin-2-yl}-1,2,4-oxadiazol-5(4H)-one

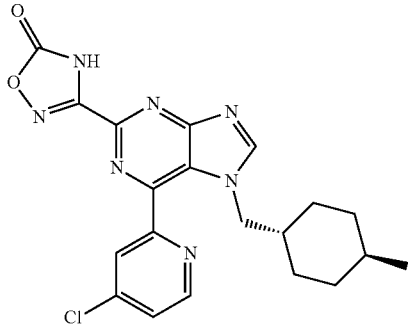 [SMILES: C[C@H]1CC[C@H](Cn2cnc3nc(-c4noc(=O)[nH]4)nc(-c4cc(Cl)ccn4)c32)CC1]

Step 1: To a sealable tube under inert atmosphere was added 6-chloro-7-((trans-4-methylcyclohexyl)methyl)-7H-purine-2-carbonitrile (0.030 g, 0.10 mmol, Preparative Example 1.3), bis(triphenylphosphine)palladium(II) chloride (0.029 g, 0.041 mmol), dioxane (1.0 mL) and 4-chloro-2-(tributylstannyl)pyridine (0.062 g, 0.16 mmol). The reaction vessel was purged with argon, sealed, and heated at 110° C. for 14 hours. The completed reaction was diluted with aqueous KF (1.0 mL, 1 N) and H$_2$O (1.0 mL). The mixture was extracted with DCM:iPrOH (9:1, 4.0 mL). The organics were collected and concentrated under reduced pressure to afford 6-(4-chloropyridin-2-yl)-7-((trans-4-methylcyclohexyl)methyl)-7H-purine-2-carbonitrile as a crude residue. MS ESI calc'd. for C$_{19}$H$_{19}$C$_1$N$_6$ [M+H]$^+$ 367, found 367.

Step 2: To a reaction vessel was added hydroxylamine HCl (0.014 g, 0.20 mmol), and sodium bicarbonate (0.042 g, 0.50 mmol) dissolved in water (0.30 mL). The vented reaction was allowed to stir for 15 minutes. Next was added 6-(4-chloropyridin-2-yl)-7-((trans-4-methylcyclohexyl)methyl)-7H-purine-2-carbonitrile (0.037 g, 0.10 mmol) as a crude residue suspended in ethanol (0.70 mL). The reaction vessel was sealed and allowed to stir at ambient temperature for 3 hours. The reaction mixture was then diluted with water and was extracted with DCM. The organic layer was collected, dried over magnesium sulfate and concentrated under reduced pressure to afford 6-(4-chloropyridin-2-yl)-N-hydroxy-7-(((trans)-4-methylcyclohexyl)methyl)-7H-purine-2-carboximidamide as a crude residue.

Step 3: To a reaction vessel was added 6-(4-chloropyridin-2-yl)-N-hydroxy-7-(((trans)-4-methylcyclohexyl)methyl)-7H-purine-2-carboximidamide (0.037 g, 0.10 mmol) as a crude residue, 1,1'-carbonyldiimidazole (0.024 g, 0.15 mmol), DBU (0.60 mL, 0.40 mmol), and acetonitrile (1.10 mL). The reaction vessel was sealed and allowed to stir for 5 hours at ambient temperature. The reaction was then diluted with water and extracted with DCM. The organics were collected and concentrated under reduced pressure. The residue was purified by reverse phase preparative HPLC (0:100 to 95:5 acetonitrile:water: 0.1% v/v TFA modifier) to afford 3-{6-(4-chloropyridin-2-yl)-7-[(trans-4-methylcyclohexyl)methyl]-7H-purin-2-yl}-1,2,4-oxadiazol-5(4H)-one. MS ESI calc'd. for C$_{20}$H$_{20}$C$_1$N$_7$O$_2$ [M+H]$^+$ 426, found 426. $^1$H NMR (600 MHz, DMSO) δ 8.94 (s, 1H), 8.81 (d, 1H), 8.65 (d, 1H), 7.81 (dd, 1H), 4.55 (d, 2H), 1.45 (d, 2H), 1.08 (m, 3H), 1.00 (m, 1H), 0.81 (m, 3H), 0.69 (d, 3H), 0.48 (m, 2H).

Preparative Example 2.2: 5-chloro-2-methyl-3-(4,4,5,5-tetramethyl-1,3,2-dioxaborolan-2-yl)pyridine

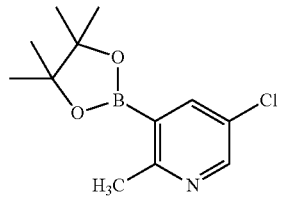

Step 1: MeMgBr (4.40 mL, 8.80 mmol) was added dropwise to a 0° C. solution of 2,3-dibromo-5-chloropyridine (2.00 g, 7.40 mmol) and Ni(dppf)Cl$_2$ (0.40 g, 0.740 mmol) in THF (25 mL). After 2 hours, a second addition of MeMgBr (4.40 mL, 8.80 mmol) was carried out and the reaction was stirred at 0° C. for 2 more hours. The reaction was then quenched with saturated aqueous NH$_4$Cl (50 ml) and extracted with EtOAc (2×50 mL). The combined organic layers were dried over anhydrous Na$_2$SO$_4$, filtered, and concentrated under reduced pressure. The residue was purified on a silica gel column (0 to 50% EtOAc/hexanes) to afford 3-bromo-5-chloro-2-methylpyridine. $^1$H NMR (300 MHz, CDCl$_3$) δ 8.38 (d, J=2.1 Hz, 1H), 7.80 (d, J=2.1 Hz, 1H), 2.63 (s, 3H).

Step 2: To a solution of 3-bromo-5-chloro-2-methylpyridine (0.60 g, 2.91 mmol) in 1,4-dioxane (12 mL) was added bis(pinacolato)diboron (1.47 g, 5.82 mmol), Pd(dppf)Cl$_2$ (0.106 g, 0.145 mmol) and KOAc (0.857, 8.73 mmol). The mixture was sparged with Ar for 5 minutes and then the reaction was sealed and heated at 90° C. for 1 hour. The reaction was then diluted with water (30 ml) and extracted with EtOAc (2×50 mL). The combined organic extracts were dried over anhydrous Na$_2$SO$_4$, filtered, and concentrated under reduced pressure. The residue was purified on a silica gel column (0 to 50% EtOAc/hexanes) to afford 5-chloro-2-methyl-3-(4,4,5,5-tetramethyl-1,3,2-dioxaborolan-2-yl)pyridine. MS (ES)=254 (M+1)$^+$.

Example 2.22: 3-{6-[3-chloro-5-(2-methoxyethoxy)phenyl]-7-[(trans-4-methylcyclohexyl)methyl]-7H-purin-2-yl}-1,2,4-oxadiazol-5(4H)-one

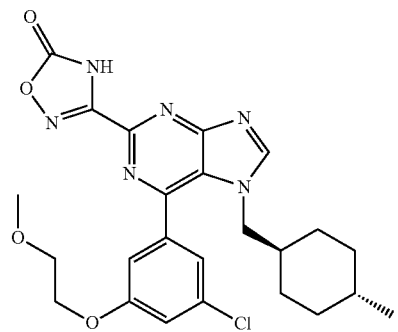 [SMILES: COCCOc1cc(Cl)cc(-c2nc(-c3noc(=O)[nH]3)nc3ncn(C[C@H]4CC[C@H](C)CC4)c23)c1]

Step 1: 2,6-dichloro-7-((trans-4-methylcyclohexyl)methyl)-7H-purine (Preparative Example 1.2, Step 4; 3.44 g, 7.49 mmol), 3-chloro-5-hydroxyphenylboronic acid (1.32 g, 8.39 mmol), potassium phosphate (12.2 g, 37.4 mmol), and 1,1'-Bis(diphenylphosphino) ferrocene-palladium(II)dichloride (1.1 g, 1.49 mmol) were combined in a vial that had been oven-dried and flushed with nitrogen. Dioxane (75 mL) was added and the vial was sealed and heated at 90° C. for 4 hours. The reaction mixture was cooled to room temperature, filtered through celite, and the filtrate was concentrated under reduced pressure. The residue was purified by silica gel chromatography (0-100% ethyl acetate/hexanes, linear gradient) to afford 3-chloro-5-(2-chloro-7-(((trans)-4-methyl cyclohexyl)methyl)-7H-purin-6-yl)phenol. MS (ES)=391 (M+1)+.

Step 2: 3-chloro-5-(2-chloro-7-(((trans)-4-methylcyclohexyl)methyl)-7H-purin-6-yl)phenol (3.44 g, 7.49 mmol), cesium carbonate (12.2 g, 37.4 mmol), and 1-bromo-2-methoxy ethane (1.03 g, 74.8 mmol) were combined in a vial that had been oven-dried and flushed with nitrogen. DMF (75 mL) was added and the vial was sealed and heated to 60° C. for 3 hours. The reaction mixture was cooled to room temperature, filtered through celite, and the filtrate was concentrated under reduced pressure. The residue was purified by silica gel chromatography (0-100% ethyl acetate/hexanes, linear gradient) to afford 2-chloro-6-(3-chloro-5-(2-methoxyethoxy)phenyl)-7-(((trans)-4-methylcyclohexyl)methyl)-7H-purine. MS (ES)=449 (M+1)+.

Step 3: An oven-dried, nitrogen cooled flask was charged with palladium(II) acetate (70 mg, 0.312 mmol) and (R)-(+)-2,2'-bis(diphenylphosphino)-1,1'-binaphthyl (195 mg, 0.313 mmol). N,N-Dimethylacetamide (18.7 mL) was added and the mixture was degassed for three minutes with nitrogen (sparge). Sulfuric acid (0.017 mL, 0.32 mmol) was added and the mixture was degassed for three minutes with nitrogen (sparge). The flask was sealed and heated to 80° C. for 30 minutes. This catalyst solution was then cooled to room temperature and added to a second nitrogen purged flask containing 2-chloro-6-(3-chloro-5-(2-methoxyethoxyl) phenyl)-7-(((trans)-4-methylcyclohexyl)methyl)-7H-purine (1.68 g, 3.14 mmol), zinc cyanide (0.184 g, 1.57 mmol), and zinc (21 mg, 0.32 mmol). The flask was purged with nitrogen for five minutes, sealed, and heated to 100° C. for 3.5 hours. The reaction was then cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 6-(3-chloro-5-(2-methoxyethoxy)phenyl)-7-4(trans)-4-methylcyclohexyl)methyl)-7H-purine-2-carbonitrile. MS (ES)=440 (M+1)+.

Steps 4 and 5: Using procedures similar to those described in Example 2.1 (Steps 1 and 2), 6-(3-chloro-5-(2-methoxyethoxy)phenyl)-7-(((trans)-4-methylcyclohexyl)methyl)-7H-purine-2-carbonitrile was converted to 3-{6-[3-chloro-5-(2-methoxyethoxy)phenyl]-7-[(trans-4-methylcyclohexyl)methyl]-7H-purin-2-yl}-1,2,4-oxadiazol-5(4H)-one. $^1$H NMR (400 MHz, CD$_3$OD) δ 8.79 (s, 1H), 7.39 (s, 1H), 7.27 (brs, 2H), 4.22-4.25 (m, 2H), 4.00 (d, J=6.8 Hz, 2H), 3.76-3.78 (m, 2H), 3.96 (s, 3H), 1.55-1.58 (m, 2H), 1.18-1.20 (m, 1H), 1.06-1.09 (m, 1H), 0.83-0.86 (m, 4H), 0.78 (d, J=8.0 Hz, 2H), 0.59-0.63 (m, 3H). MS (APCI)=499 (M+1)+. The compounds in Table 2 were described above or were prepared using procedures which are analogous to those described above.

TABLE 2

| Ex. | FRET IC$_{50}$ (nM) | Structure | Chemical Name | Salt Form | [M + H]+ Calc'd | [M + H]+ Obsv'd |
|---|---|---|---|---|---|---|
| 2.1 | 53.37 | 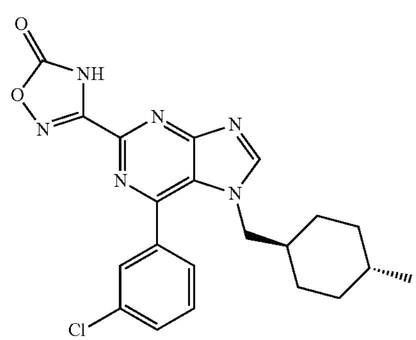 [SMILES: C[C@H]1CC[C@H](Cn2cnc3nc(-c4noc(=O)[nH]4)nc(-c4cccc(Cl)c4)c32)CC1] | 3-{6-(3-chlorophenyl)-7-[(trans-4-methylcyclohexyl)methyl]-7H-purin-2-yl}-1,2,4-oxadiazol-5(4H)-one | TFA | 425 | 425 |
| 2.2 | 133.8 | 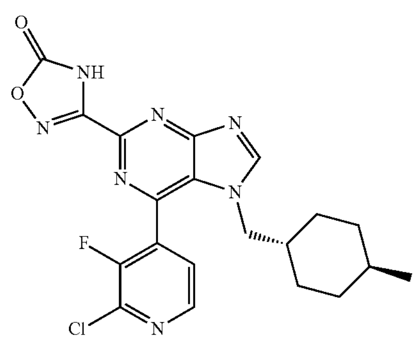 [SMILES: C[C@H]1CC[C@H](Cn2cnc3nc(-c4noc(=O)[nH]4)nc(-c4ccnc(Cl)c4F)c32)CC1] | 3-{6-(2-chloro-3-fluoropyridin-4-yl)-7-[(trans-4-methylcyclohexyl)methyl]-7H-purin-2-yl}-1,2,4-oxadiazol-5(4H)-one | TFA | 444 | 444 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.3 | 251 | 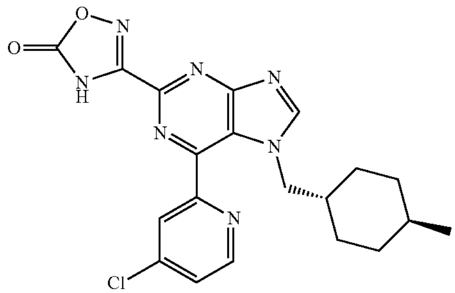 [SMILES: C[C@H]1CC[C@H](Cn2cnc3nc(-c4noc(=O)[nH]4)nc(-c4cc(Cl)ccn4)c32)CC1] | 3-{6-(4-chloropyridin-2-yl)-7-[(trans-4-methylcyclohexyl)methyl]-7H-purin-2-yl}-1,2,4-oxadiazol-5(4H)-one | TFA | 426 | 426 |
| 2.4 | 413.3 | 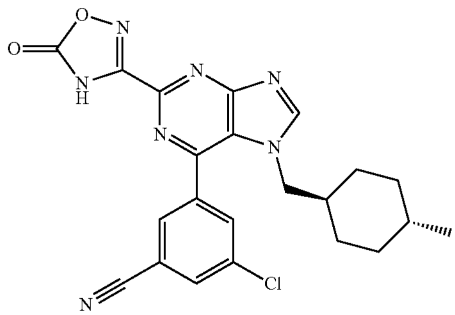 [SMILES: C[C@H]1CC[C@H](Cn2cnc3nc(-c4noc(=O)[nH]4)nc(-c4cc(Cl)cc(C#N)c4)c32)CC1] | 3-chloro-5-{7-[(trans-4-methylcyclohexyl)methyl]-2-(5-oxo-4,5-dihydro-1,2,4-oxadiazol-3-yl)-7H-purin-6-yl}benzonitrile | TFA | 450 | 450 |
| 2.5 | 841.6 | 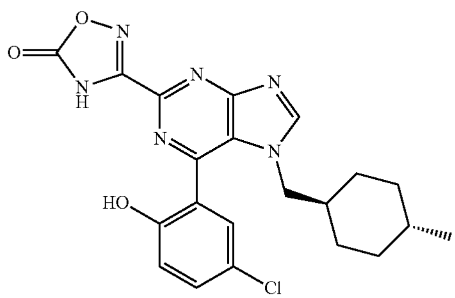 [SMILES: C[C@H]1CC[C@H](Cn2cnc3nc(-c4noc(=O)[nH]4)nc(-c4cc(Cl)ccc4O)c32)CC1] | 3-{6-(5-chloro-2-hydroxyphenyl)-7-[(trans-4-methylcyclohexyl)methyl]-7H-purin-2-yl}-1,2,4-oxadiazol-5(4H)-one | TFA | 441 | 441 |
| 2.6 | 312.3 | 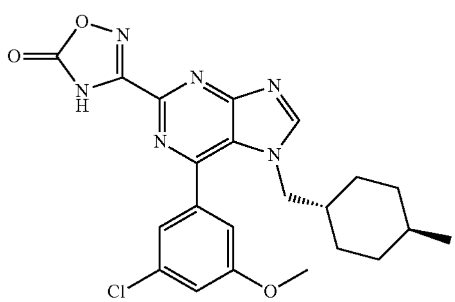 [SMILES: COc1cc(Cl)cc(-c2nc(-c3noc(=O)[nH]3)nc3ncn(C[C@H]4CC[C@H](C)CC4)c23)c1] | 3-{6-(3-chloro-5-methoxyphenyl)-7-[(trans-4-methylcyclohexyl)methyl]-7H-purin-2-yl}-1,2,4-oxadiazol-5(4H)-one | TFA | 455 | 455 |
| 2.7 | 111.1 | 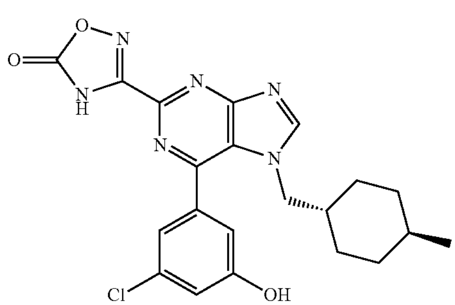 [SMILES: C[C@H]1CC[C@H](Cn2cnc3nc(-c4noc(=O)[nH]4)nc(-c4cc(O)cc(Cl)c4)c32)CC1] | 3-{6-(3-chloro-5-hydroxyphenyl)-7-[(trans-4-methylcyclohexyl)methyl]-7H-purin-2-yl}-1,2,4-oxadiazol-5(4H)-one | TFA | 441 | 441 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.8 | 157.2 | 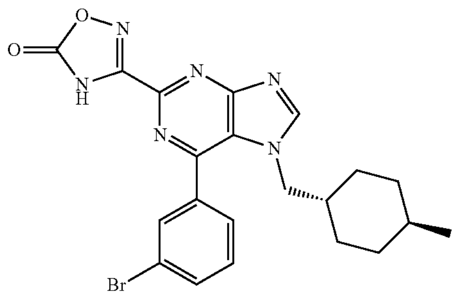 [SMILES: C[C@H]1CC[C@H](Cn2cnc3nc(-c4noc(=O)[nH]4)nc(-c4cccc(Br)c4)c32)CC1] | 3-{6-(3-bromophenyl)-7-[(trans-4-methylcyclohexyl)methyl]-7H-purin-2-yl}-1,2,4-oxadiazol-5(4H)-one | TFA | 469 | 469 |
| 2.9 | 517.7 | 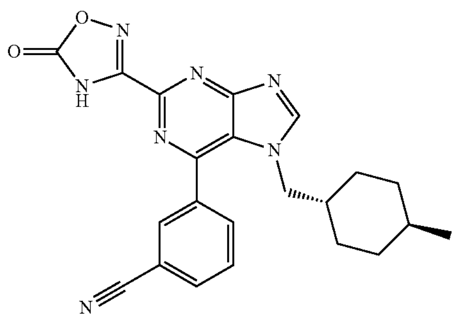 [SMILES: C[C@H]1CC[C@H](Cn2cnc3nc(-c4noc(=O)[nH]4)nc(-c4cccc(C#N)c4)c32)CC1] | 3-{7-[(trans-4-methylcyclohexyl)methyl]-2-(5-oxo-4,5-dihydro-1,2,4-oxadiazol-3-yl)-7H-purin-6-yl}benzonitrile | TFA | 416 | 416 |
| 2.10 | 71.76 | 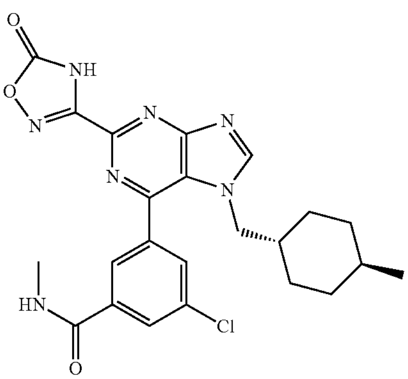 [SMILES: CNC(=O)c1cc(Cl)cc(-c2nc(-c3noc(=O)[nH]3)nc3ncn(C[C@H]4CC[C@H](C)CC4)c23)c1] | 3-chloro-N-methyl-5-(7-[(trans-4-methylcyclohexyl)methyl]-2-(5-oxo-4,5-dihydro-1,2,4-oxadiazol-3-yl)-7H-purin-6-yl}benzamide | TFA | 482 | 482 |
| 2.11 | 172.3 | 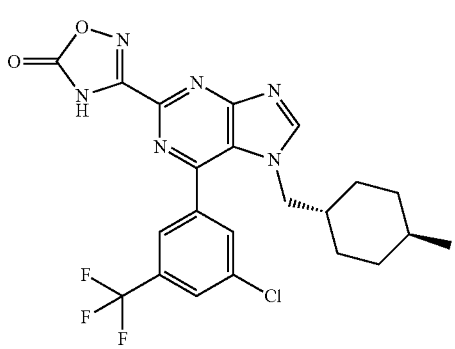 [SMILES: C[C@H]1CC[C@H](Cn2cnc3nc(-c4noc(=O)[nH]4)nc(-c4cc(Cl)cc(C(F)(F)F)c4)c32)CC1] | 3-{6-[3-chloro-5-(trifluoromethyl)phenyl]-7-[(trans-4-methylcyclohexyl)methyl]-7H-purin-2-yl}-1,2,4-oxadiazol-5(4H)-one | TFA | 493 | 493 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.12 | 86 | 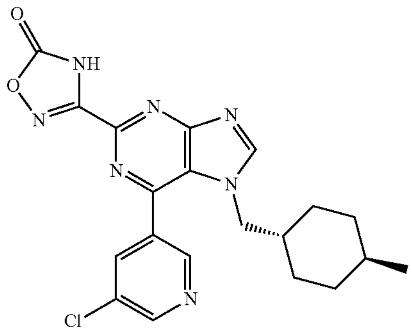 [SMILES: C[C@H]1CC[C@H](Cn2cnc3nc(-c4noc(=O)[nH]4)nc(-c4cncc(Cl)c4)c32)CC1] | 3-{6-(5-chloropyridin-3-yl)-7-[(trans-4-methylcyclohexyl)methyl]-7H-purin-2-yl}-1,2,4-oxadiazol-5(4H)-one | TFA | 426 | 426 |
| 2.13 | 50.83 | 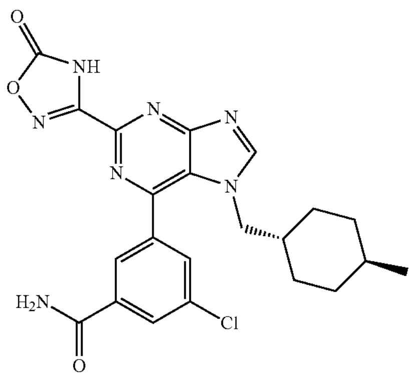 [SMILES: C[C@H]1CC[C@H](Cn2cnc3nc(-c4noc(=O)[nH]4)nc(-c4cc(Cl)cc(C(N)=O)c4)c32)CC1] | 3-chloro-5-{7-[(trans-4-methylcyclohexyl)methyl]-2-(5-oxo-4,5-dihydro-1,2,4-oxadiazol-3-yl)-7H-purin-6-yl}benzamide | TFA | 468 | 468 |
| 2.14 | 41.69 | 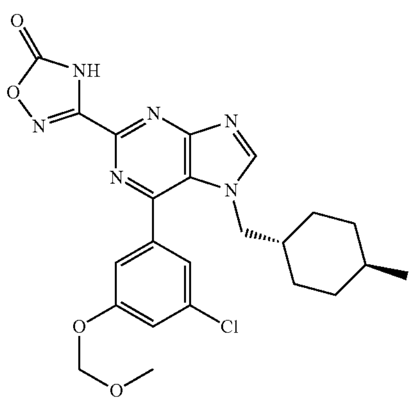 [SMILES: COCOc1cc(Cl)cc(-c2nc(-c3noc(=O)[nH]3)nc3ncn(C[C@H]4CC[C@H](C)CC4)c23)c1] | 3-{6-[3-chloro-5-(methoxymethoxy)phenyl]-7-[(trans-4-methylcyclohexyl)methyl]-7H-purin-2-yl}-1,2,4-oxadiazol-5(4H)-one | TFA | 485 | 485 |
| 2.15 | 187.7 | 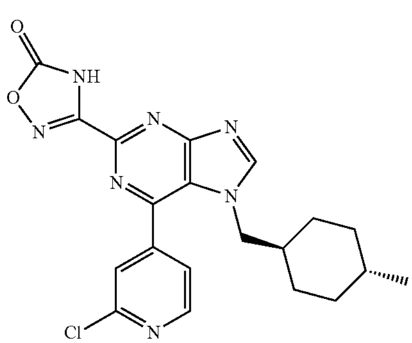 [SMILES: C[C@H]1CC[C@H](Cn2cnc3nc(-c4noc(=O)[nH]4)nc(-c4ccnc(Cl)c4)c32)CC1] | 3-{6-(2-chloropyridin-4-yl)-7-[(trans-4-methylcyclohexyl)methyl]-7H-purin-2-yl}-1,2,4-oxadiazol-5(4H)-one | | 426 | 426 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.16 | 87.63 | 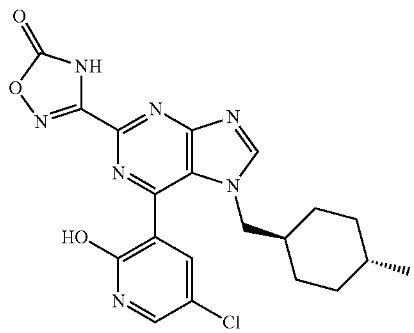 [SMILES: C[C@H]1CC[C@H](Cn2cnc3nc(-c4noc(=O)[nH]4)nc(-c4cc(Cl)cnc4O)c32)CC1] | 3-{6-(5-chloro-2-hydroxypyridin-3-yl)-7-[(trans-4-methylcyclohexyl)methyl]-7H-purin-2-yl}-1,2,4-oxadiazol-5(4H)-one | TFA | 442 | 442 |
| 2.17 | 250.4 | 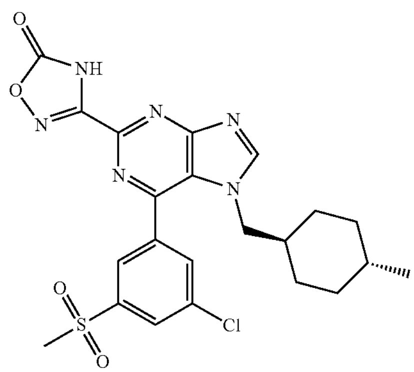 [SMILES: CS(=O)(=O)c1cc(Cl)cc(-c2nc(-c3noc(=O)[nH]3)nc3ncn(C[C@H]4CC[C@H](C)CC4)c23)c1] | 3-{6-[3-chloro-5-(methylsulfonyl)phenyl]-7-[(trans-4-methylcyclohexyl)methyl]-7H-purin-2-yl}-1,2,4-oxadiazol-5(4H)-one | | 503 | 503 |
| 2.18 | 331.2 | 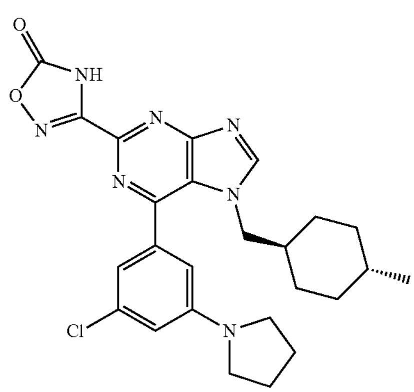 [SMILES: C[C@H]1CC[C@H](Cn2cnc3nc(-c4noc(=O)[nH]4)nc(-c4cc(Cl)cc(N5CCCC5)c4)c32)CC1] | 3-{6-(3-chloro-5-pyrrolidin-1-ylphenyl)-7-[(trans-4-methylcyclohexyl)methyl]-7H-purin-2-yl}-1,2,4-oxadiazol-5(4H)-one | | 494 | 494 |
| 2.19 | 578.7 | 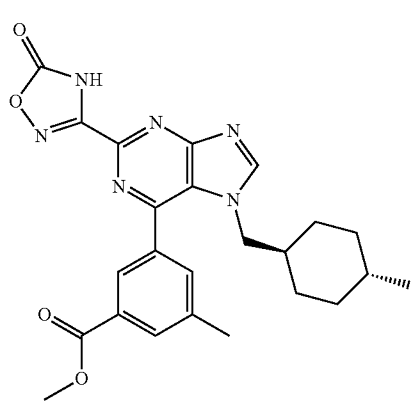 [SMILES: COC(=O)c1cc(C)cc(-c2nc(-c3noc(=O)[nH]3)nc3ncn(C[C@H]4CC[C@H](C)CC4)c23)c1] | methyl 3-methyl-5-{7-[(trans-4-methylcyclohexyl)methyl]-2-(5-oxo-4,5-dihydro-1,2,4-oxadiazol-3-yl)-7H-purin-6-yl}benzoate | | 463 | 463 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.20 | 212.9 | 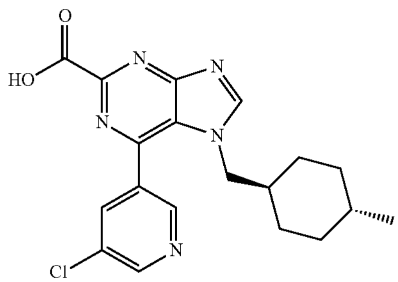 [SMILES: C[C@H]1CC[C@H](Cn2cnc3nc(C(=O)O)nc(-c4cncc(Cl)c4)c32)CC1] | 6-(5-chloropyridin-3-yl)-7-[(trans-4-methylcyclohexyl)methyl]-7H-purine-2-carboxylic acid | TFA | 386 | 386 |
| 2.21 | 87.78 | 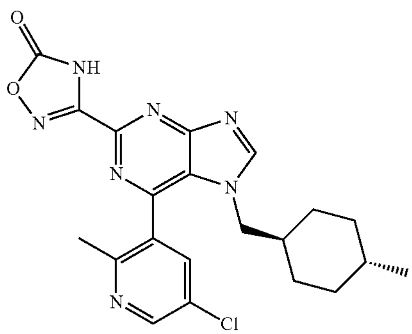 [SMILES: Cc1ncc(Cl)cc1-c1nc(-c2noc(=O)[nH]2)nc2ncn(C[C@H]3CC[C@H](C)CC3)c12] | 3-{6-(5-chloro-2-methylpyridin-3-yl)-7-[(trans-4-methylcyclohexyl)methyl]-7H-purin-2-yl}-1,2,4-oxadiazol-5(4H)-one | | 440 | 440 |
| 2.22 | 68.52 | 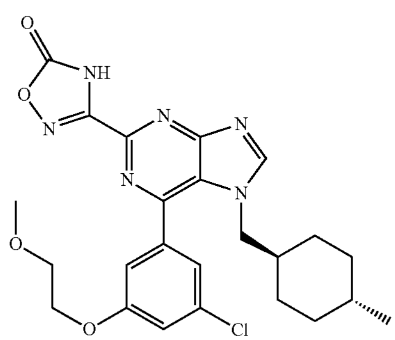 [SMILES: COCCOc1cc(Cl)cc(-c2nc(-c3noc(=O)[nH]3)nc3ncn(C[C@H]4CC[C@H](C)CC4)c23)c1] | 3-{6-[3-chloro-5-(2-methoxyethoxy)phenyl]-7-[(trans-4-methylcyclohexyl)methyl]-7H-purin-2-yl}-1,2,4-oxadiazol-5(4H)-one | | 499 | 499 |
| 2.23 | 131.9 | 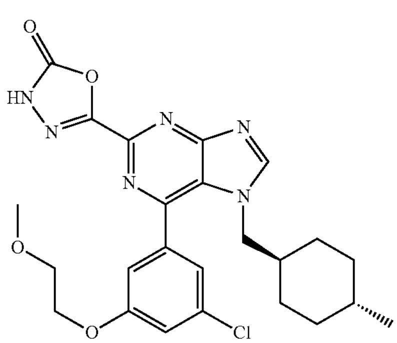 [SMILES: COCCOc1cc(Cl)cc(-c2nc(-c3n[nH]c(=O)o3)nc3ncn(C[C@H]4CC[C@H](C)CC4)c23)c1] | 5-{6-[3-chloro-5-(2-methoxyethoxy)phenyl]-7-[(trans-4-methylcyclohexyl)methyl]-7H-purin-2-yl}-1,3,4-oxadiazol-2(3H)-one | | 499 | 499 |

Preparative Example 3.1: trans-1-(bromomethyl)-4-(trifluoromethyl)cyclohexane

Step 1: BH$_3$ (100 mL, 0.1 mol, 1.0 M solution in THF) was added dropwise to a 0° C. solution of trans-4-(trifluoromethyl)cyclohexanecarboxylic acid (19.6 g, 0.1 mol) in dry THF (100 mL). The reaction was stirred at room temperature for 5 hours and then quenched with water. The mixture was extracted with EtOAc, washed with brine, dried over Na$_2$SO$_4$, filtered and concentrated to give (trans-4-(trifluoromethyl)cyclohexyl)methanol. $^1$H NMR (300 MHz, CDCl$_3$): δ 3.48-3.47 (d, 2H), 2.00-1.89 (m, 5H), 1.51-1.43 (m, 1H), 1.35-1.26 (m, 2H), 1.05-0.96 (m, 2H).

Step 2: PPh$_3$ (30.75 g, 117.4 mmol) was added slowly to a 0° C. solution of (trans-4-(trifluoromethyl)cyclohexyl)methanol (17.8 g, 97.8 mmol) and CBr$_4$ (38.85 g, 117.4 mmol) in dry DCM (200 mL). The reaction was stirred at room temperature overnight and then concentrated. Hexane/EtOAc (9/1, 300 ml) was added and the mixture was stirred for 1 hour and then filtered. The filtrate was concentrated and distilled under vacuum to give trans-1-(bromomethyl)-4-(trifluoromethyl)cyclohexane. $^1$H NMR (300 MHz, CDCl$_3$): δ 3.30-3.28 (d, 2H), 2.02-1.92 (m, 5H), 1.70-1.59 (m, 1H), 1.40-1.27 (m, 2H), 1.13-1.00 (m, 2H).

Preparative Example 3.2: 2,6-dichloro-7-((trans-4-(trifluoromethyl)cyclohexyl)methyl)-7H-purine

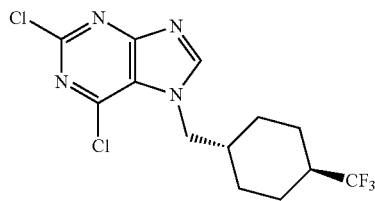 [SMILES: FC(F)(F)[C@H]1CC[C@H](Cn2cnc3nc(Cl)nc(Cl)c32)CC1]

Step 1: Na$_2$CO$_3$ (12.72 g, 12 mmol) was added to a solution of trans-1-(bromomethyl)-4-(trifluoromethyl)cyclohexane (Preparative Example 3.1, 2.94 g, 12 mmol) and 3-methyl-1H-purine-2,6(3H,7H)-dione (1.66 g, 10 mmol) in dry DMF (30 mL). The reaction was stirred at 100° C. overnight and then quenched with 1N HCl (60 ml), filtered and concentrated under vacuum to give 3-methyl-7-((trans-4-(trifluoromethyl)cyclohexyl)methyl)-1H-purine-2,6(3H,7H)-dione.

Step 2: DBU (6.63 g, 43.6 mmol) was added to a mixture of crude 3-methyl-7-((trans-4-(trifluoromethyl)cyclohexyl)methyl)-1H-purine-2,6(3H,7H)-dione (3.1 g, 9.39 mmol) in POCl$_3$ (30 mL) at 60° C. The reaction was stirred at 120° C. for 2 h and then cooled to room temperature and concentrated. The residue was diluted with EtOAc, washed with saturated aq. NaHCO$_3$ solution and brine, dried over Na$_2$SO$_4$, filtered, and concentrated. The residue was purified by flash chromatography on silica gel to give 2,6-dichloro-7-((trans-4-(trifluoromethyl)cyclohexyl)methyl)-7H-purine. MS ESI calc'd. for C$_{13}$H$_{13}$Cl$_2$F$_3$N$_4$ [M+H]$^+$ 353, found 353.

$^1$H NMR (300 MHz, CDCl$_3$): δ 8.18 (s, 1H), 4.32-4.30 (d, 2H), 2.07-1.77 (m, 6H), 1.38-1.06 (m, 4H).

Preparative Example 3.3: 6-4(R)-1-cyclobutylethyl)amino)-7-((trans-4-(trifluoromethyl)cyclohexyl)methyl)-7H-purine-2-carbonitrile

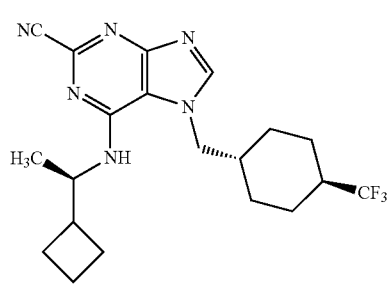 [SMILES: C[C@@H](Nc1nc(C#N)nc2ncn(C[C@H]3CC[C@H](C(F)(F)F)CC3)c12)C1CCC1]

Step 1: A mixture of 2,6-dichloro-7-((trans-4-(trifluoromethyl)cyclohexyl)methyl)-7H-purine (400 mg, 1.13 mmol, Preparative Example 3.2), (R)-1-cyclobutylethylamine (766.5 mg, 5.66 mmol) and diisopropyl ethylamine (731 mg, 5.66 mmol) in ethanol (5.0 mL) was heated to reflux for 12 hours. The reaction mixture was then cooled to room temperature and concentrated. The residue was dissolved in EtOAc (30 mL) and the organic layer was washed with water (15 mL) and brine (15 mL), dried over anhydrous Na$_2$SO$_4$, filtered, and concentrated in vacuo. Purification of the crude material by column chromatography (60% EtOAc/hexanes) afforded 2-chloro-N—((R)-1-cyclobutylethyl)-7-((trans-4-(trifluoromethyl)cyclohexyl)methyl)-7H-purin-6-amine as white solid. $^1$H NMR (400 MHz, CDCl$_3$) δ 7.76 (s, 1H), 4.59 (d, J=8.0 Hz, 2H), 4.45-4.41 (m, 1H), 4.15 (dd, J=16.0, 12.0 Hz, 1H), 4.05 (dd, J=16.0, 16.0 Hz, 1H), 2.37-2.43 (m, 1H), 1.66-2.10 (m, 10H), 1.26-1.30 (m, 2H), 1.25 (d, J=9.6 Hz, 3H), 1.12-1.16 (m, 2H). MS (APCI)=416 (M+1)$^+$.

Step 2: A mixture of 2-chloro-N—((R)-1-cyclobutylethyl)-7-((trans-4-(trifluoromethyl)cyclohexyl)methyl)-7H-purin-6-amine (400 mg, 0.96 mmol) and zinc cyanide (90.3 mg, 0.76 mmol) in DMA (5 ml) in a sealable tube was degassed with Ar for 30 minutes. Pd(PPh$_3$)$_4$ (221 mg, 0.19 mmol) was added and the reaction was evacuated and refilled with Ar three times. The reaction was then sealed and heated at 120° C. for 12 hours. Next, the reaction was cooled to room temperature. Ice-cooled water (40 ml) was added slowly and the reaction mixture was extracted with ethyl acetate (3×50 mL). The combined organic layers were dried over sodium sulfate, filtered, and concentrated under reduced pressure. Purification of the residue on a silica gel column with 0 to 100% EtOAc/hexanes afforded 6-(((R)-1-cyclobutylethyl)amino)-7-((trans-4-(trifluoromethyl)cyclohexyl)methyl)-7H-purine-2-carbonitrile as white solid. $^1$H NMR (400 MHz, CDCl$_3$) δ 7.85 (s, 1H), 4.59 (d, J=8.0 Hz, 2H), 4.38 (m, 1H), 4.11 (dd, J=16.0, 16.0 Hz, 1H), 4.03 (dd, J=16.0, 16.0 Hz, 1H), 2.05-2.39 (m, 1H), 1.66-2.05 (m, 10H), 1.20-1.24 (m, 2H), 1.18 (d, J=6.4 Hz, 3H), 1.12-1.16 (m, 2H). MS(APCI)=407 (M+1)$^+$.

Example 3.1: 3-(6-{[(1R)-1-cyclobutylethyl]amino}-7-{[trans-4-(trifluoromethyl)cyclohexyl]methyl}-7H-purin-2-yl)-1,2,4-oxadiazol-5(4H)-one

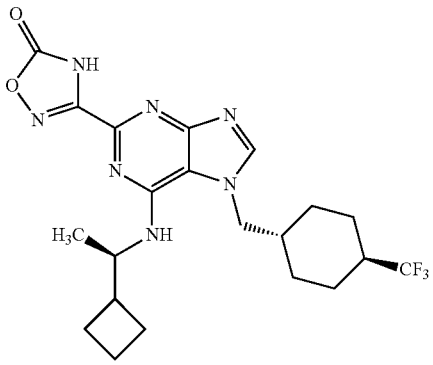 [SMILES: C[C@@H](Nc1nc(-c2noc(=O)[nH]2)nc2ncn(C[C@H]3CC[C@H](C(F)(F)F)CC3)c12)C1CCC1]

Step 1: Using a procedure similar to that described in Example 1.7 (Step 1), and starting with 6-(((R)-1-cyclobutylethyl)amino)-7-((trans-4-(trifluoromethyl)cyclohexyl)methyl)-7H-purine-2-carbonitrile (Preparative Example 3.3), 6-(((R)-1-cyclobutylethyl)amino)-N-hydroxy-7-((trans-4-(trifluoromethyl)cyclohexyl)methyl)-7H-purine-2-carboximidamide was prepared. $^1$H NMR (400 MHz, DMSO-$d_6$) δ 9.91 (s, 1H), 8.22 (s, 1H), 6.22 (d, J=8.4 Hz, 1H), 5.64 (br s, 2H), 4.59 (dd, J=14.8, 5.6 Hz, 1H), 4.39-4.51 (m, 1H), 4.14 (dd, J=14.8, 8.8 Hz, 1H), 2.52-2.63 (m, 1H), 2.13-2.26 (m, 1H), 1.97-2.09 (m, 1H), 1.85-1.96 (m, 2H), 1.68-1.85 (m, 6H), 1.55-1.68 (m, 1H), 1.21-1.34 (m, 1H), 1.13 (d, J=6.4 Hz, 3H), 0.94-1.19 (m, 4H). MS (ES)=440 (M+1)$^+$.

Step 2: Using a procedure similar to that described in Example 1.7 (Step 2), and starting with 6-(((R)-1-cyclobutylethyl)amino)-N-hydroxy-7-((trans-4-(trifluoromethyl)cyclohexyl)methyl)-7H-purine-2-carboximidamide, 3-(6-{[(1R)-1-cyclobutylethyl]amino}-7-{[trans-4-(trifluoromethyl)cyclohexyl]methyl}-7H-purin-2-yl)-1,2,4-oxadiazol-5(4H)-one was prepared. $^1$H NMR (400 MHz, DMSO-$d_6$) δ 12.88 (br s, 1H), 8.36 (s, 1H), 6.52 (d, J=8.8 Hz, 1H), 4.53-4.69 (m, 2H), 4.21 (dd, J=14.4, 8.4 Hz, 1H), 2.52-2.63 (m, 1H), 2.12-2.28 (m, 1H), 1.96-2.10 (m, 1H), 1.69-1.94 (m, 7H), 1.54-1.68 (m, 1H), 1.28-1.38 (m, 1H), 1.21-1.28 (m, 1H), 1.14 (d, J=6.4 Hz, 3H), 0.98-1.20 (m, 4H). MS (ES)=466 (M+1)$^+$.

Example 3.2: 3-[6-(3-chlorophenyl)-7-{[trans-4-(trifluoromethyl)cyclohexyl]methyl}-7H-purin-2-yl]-1,2,4-oxadiazol-5(4H)-one

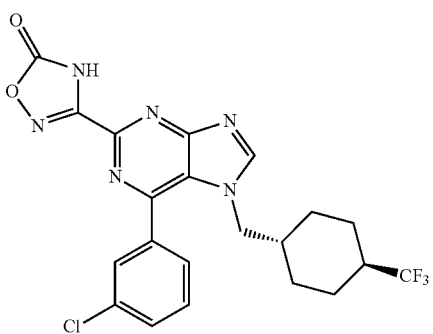 [SMILES: O=c1[nH]c(-c2nc(-c3cccc(Cl)c3)c3c(ncn3C[C@H]3CC[C@H](C(F)(F)F)CC3)n2)no1]

Step 1: Using a procedure analogous to that described in Example 2.2 (Step 1) and starting with 2,6-dichloro-7-((trans-4-(trifluoromethyl)cyclohexyl)methyl)-7H-purine (Preparative Example 3.2), 2-chloro-6-(3-chlorophenyl)-7-((trans-4-(trifluoromethyl)cyclohexyl)methyl)-7H-purine was prepared. $^1$H NMR (400 MHz, CDCl$_3$) δ 8.17 (s, 1H), 7.49-7.64 (m, 4H), 3.87 (d, J=6.8 Hz, 2H), 1.77-1.92 (m, 3H), 1.16-1.27 (m, 2H), 0.92-1.10 (m, 3H), 0.71-0.84 (m, 2H). (ES)=429 (M+1)$^+$.

Step 2: Using a procedure analogous to that described in Preparative Example 3.3 (Step 2), and starting with 2-chloro-6-(3-chlorophenyl)-7-((trans-4-(trifluoromethyl)cyclohexyl)methyl)-7H-purine, 6-(3-chlorophenyl)-7-((trans-4-(trifluoromethyl)cyclohexyl)methyl)-7H-purine-2-carbonitrile was prepared. $^1$H NMR (400 MHz, DMSO-$d_6$) δ 9.02 (s, 1H), 7.87 (t, J=1.6 Hz, 1H), 7.64-7.77 (m, 3H), 3.93 (d, J=6.4 Hz, 2H), 2.02-2.19 (m, 1H), 1.63-1.78 (m, 2H), 0.74-1.08 (m, 7H). (ES)=420 (M+1)$^+$.

Step 3: Using a procedure analogous to that described in Example 2.2 (Step 2) and starting with 6-(3-chlorophenyl)-7-((trans-4-(trifluoromethyl)cyclohexyl)methyl)-7H-purine-2-carbonitrile, 6-(3-chlorophenyl)-N-hydroxy-7-((trans-4-(trifluoromethyl)cyclohexyl)methyl)-7H-purine-2-carboximidamide was prepared. $^1$H NMR (400 MHz, DMSO-$d_6$) δ 9.98 (s, 1H), 8.76 (s, 1H), 7.87 (t, J=2.0 Hz, 1H), 7.60-7.72 (m, 3H), 5.84 (br s, 2H), 3.92 (d, J=6.4 Hz, 2H), 2.01-2.14 (m, 1H), 1.62-1.75 (m, 2H), 0.91-1.03 (m, 3H), 0.75-0.91 (m, 4H). MS (ES)=453 (M+1)$^+$.

Step 4: Using a procedure analogous to that described in Example 2.2 (Step 3) and starting with 6-(3-chlorophenyl)-N-hydroxy-7-((trans-4-(trifluoromethyl)cyclohexyl)methyl)-7H-purine-2-carboximidamide, 3-[6-(3-chlorophenyl)-7-{[trans-4-(trifluoromethyl)cyclohexyl]methyl}-7H-purin-2-yl]-1,2,4-oxadiazol-5(4H)-one was prepared. $^1$H NMR (400 MHz, DMSO-$d_6$) δ 13.25 (br s, 1H), 8.94 (s, 1H), 7.92 (t, J=1.6 Hz, 1H), 7.64-7.77 (m, 3H), 3.95 (d, J=6.4 Hz, 2H), 2.02-2.16 (m, 1H), 1.64-1.76 (m, 2H), 0.92-1.08 (m, 3H), 0.77-0.90 (m, 4H). MS (ES)=479 (M+1)$^+$.

Preparative Example 3.4:
6-(bromomethyl)spiro[2.5]octane

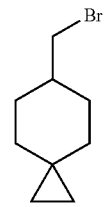

Using a procedure analogous to that described in Preparative Example 3.1 (Step 2), and starting with spiro[2.5]octan-6-ylmethanol, 6-(bromomethyl)spiro[2.5]octane was prepared. $^1$H NMR (300 MHz, CDCl$_3$) δ 3.33 (d, J=6.3 Hz, 2H), 1.76-1.89 (m, 2H), 1.61-1.76 (m, 3H), 1.14-1.28 (m, 2H), 0.86-0.95 (m, 2H), 0.26-0.33 (m, 2H), 0.14-0.22 (m, 2H).

Preparative Example 3.5:(R)-6-((1-cyclobutylethyl)amino)-7-(spiro[2.5]octan-6-ylmethyl)-7H-purine-2-carbonitrile

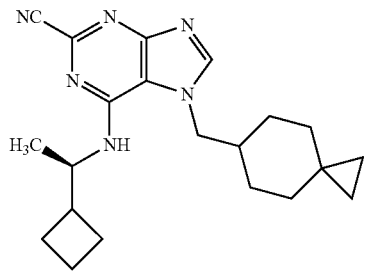 [SMILES: C[C@@H](Nc1nc(C#N)nc2ncn(CC3CCC4(CC3)CC4)c12)C1CCC1]

Step 1: 2,6-dichloro-7H-purine (1.00 g, 5.31 mmol) was dissolved in DMF (15 mL). K$_2$CO$_3$ (1.46 g, 10.6 mmol) was added followed by NaI (0.80 g, 5.31 mmol) and the reaction was stirred for 5 minutes before adding 6-(bromomethyl)spiro[2.5]octane (1.60 g, 7.97 mmol) (Preparative Example 3.4) to the reaction mixture. The reaction mixture was warmed to 60° C. and stirring was continued for 12 hours. The reaction mixture was then diluted with EtOAc (100 mL) and the organic layer was washed with water (2×50 mL), dried over anhydrous Na$_2$SO$_4$, filtered, and concentrated. The residue was purified on a silica gel column (0 to 10% MeOH/CH$_2$Cl$_2$) to afford 2,6-dichloro-7-(spiro[2.5]octan-6-ylmethyl)-7H-purine. $^1$H NMR (400 MHz, CDCl$_3$) δ 8.20 (s, 1H), 4.32 (d, J=7.2 Hz, 2H), 1.82-1.96 (m, 1H), 1.56-1.74 (m, 2H), 1.18-1.32 (m, 4H), 0.83-0.97 (m, 2H), 0.28-0.36 (m, 2H), 0.16-0.25 (m, 2H).

Step 2: Using a procedure analogous to that described in Preparative Example 3.3 (Step 1), and starting with 2,6-dichloro-7-(spiro[2.5]octan-6-ylmethyl)-7H-purine, (R)-2-chloro-N-(1-cyclobutylethyl)-7-(spiro[2.5]octan-6-ylmethyl)-7H-purin-6-amine was prepared. $^1$H NMR (400 MHz, CDCl$_3$) δ 7.78 (s, 1H), 4.56 (d, J=8.0 Hz, 1H), 4.37-4.48 (m, 1H), 4.08 (dd, J=14.8, 6.4 Hz, 1H), 4.01 (dd, J=14.8, 8.0 Hz, 1H), 2.35-2.47 (m, 1H), 1.98-2.14 (m, 2H), 1.80-1.97 (m, 4H), 1.58-1.76 (m, 4H), 1.47-1.56 (m, 1H), 1.21 (d, J=6.4 Hz, 3H), 1.15-1.32 (m, 2H), 0.87-0.99 (m, 2H), 0.30-0.37 (m, 2H), 0.17-0.24 (m, 2H). MS (ES)=374 (M+1)$^+$.

Step 3: Using a procedure analogous to that described in Preparative Example 3.3 (Step 2), and starting with (R)-2-chloro-N-(1-cyclobutylethyl)-7-(spiro[2.5]octan-6-ylmethyl)-7H-purin-6-amine, (R)-6-((1-cyclobutylethyl)amino)-7-(spiro[2.5]octan-6-ylmethyl)-7H-purine-2-carbonitrile was prepared. $^1$H NMR (300 MHz, CDCl$_3$) δ 7.90 (s, 1H), 4.66 (br d, J=7.8 Hz, 1H), 4.37-4.54 (m, 1H), 4.01-4.21 (m, 2H), 2.36-2.51 (m, 1H), 1.97-2.13 (m, 2H), 1.77-1.98 (m, 4H), 1.48-1.75 (m, 4H), 1.16-1.38 (m, 3H), 1.21 (d, J=6.6 Hz, 3H), 0.81-1.01 (m, 2H), 0.29-0.39 (m, 2H), 0.16-0.27 (m, 2H). MS (ES)=365 (M+1)$^+$.

Example 3.3: 3-[6-{[(1R)-1-cyclobutylethyl]amino}-7-(spiro[2.5]oct-6-ylmethyl)-7H-purin-2-yl]-1,2,4-oxadiazol-5(4H)-one

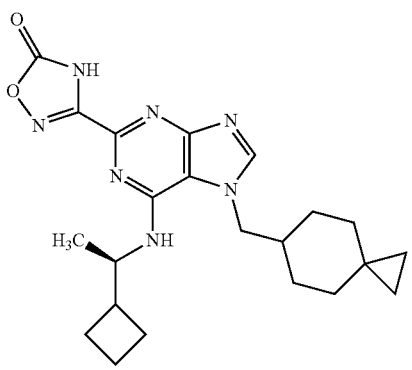 [SMILES: C[C@@H](Nc1nc(-c2noc(=O)[nH]2)nc2ncn(CC3CCC4(CC3)CC4)c12)C1CCC1]

Using a procedure analogous to that described in Example 1.7 (Steps 1 and 2) and starting with (R)-6-((1-cyclobutylethyl)amino)-7-(spiro[2.5]octan-6-ylmethyl)-7H-purine-2-carbonitrile (Preparative Example 3.5), 3-[6-{[(1R)-1-cyclobutylethyl]amino}-7-(spiro[2.5]oct-6-ylmethyl)-7H-purin-2-yl]-1,2,4-oxadiazol-5(4H)-one was prepared. $^1$H NMR (300 MHz, CDCl$_3$) δ 8.53 (br s, 1H), 4.72 (d, J=7.8 Hz, 1H), 4.52-4.68 (m, 1H), 4.05-4.27 (m, 2H), 2.37-2.54 (m, 1H), 1.43-2.15 (m, 9H), 1.15-1.36 (m, 3H), 1.26 (d, J=6.3 Hz, 3H), 0.78-1.03 (m, 3H), 0.14-0.38 (m, 4H). MS (ES)=424 (M+1)$^+$.

Example 3.4: 6-{[(1R)-1-cyclobutylethyl]amino}-7-(spiro[2.5]oct-6-ylmethyl)-7H-purine-2-carboxylic acid

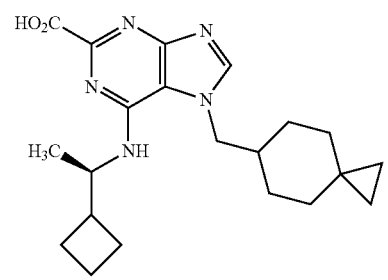 [SMILES: C[C@@H](Nc1nc(C(=O)O)nc2ncn(CC3CCC4(CC3)CC4)c12)C1CCC1]

Using a procedure analogous to that described in Example 1.1 and starting with (R)-6-((1-cyclobutylethyl)amino)-7-(spiro[2.5]octan-6-ylmethyl)-7H-purine-2-carbonitrile (Preparative Example 3.5), 6-{[(1R)-1-cyclobutylethyl]amino}-7-(spiro[2.5]oct-6-ylmethyl)-7H-purine-2-carboxylic acid was prepared. $^1$H NMR (400 MHz, CDCl$_3$) δ 7.93 (br s, 1H), 4.69-4.98 (m, 1H), 4.50-4.67 (m, 1H), 4.01-4.27 (m, 2H), 2.37-2.51 (m, 1H), 2.00-2.19 (m, 2H), 1.46-1.99 (m, 7H), 1.04-1.39 (m, 3H), 1.24 (d, J=6.0 Hz, 3H), 0.68-1.03 (m, 3H), 0.06-0.37 (m, 4H). MS (ES)=384 (M+1)$^+$.

Preparative Example 3.6: trans-5-(bromomethyl)-1,1-difluoro-2-methylcyclohexane

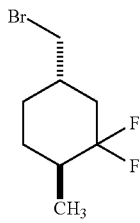

Step 1: A 100 mL round bottom flask was charged with (4-methylcyclohex-3-en-1-yl)methanol (2.50 g, 20 mmol), imidazole (2.72 g, 40 mmol) and DMF (40 mL). Tert-butyl diphenylchlorosilane (6.00 g, 22 mmol) was added dropwise at room temperature and the reaction was stirred for 16 hours. The reaction was then diluted with water and extracted using EtOAc. The organic layer was washed with water and brine, and dried over anhydrous sodium sulfate, filtered, and concentrated. The residue was purified on a silica gel column (0 to 10% EtOAc/hexanes) to afford tert-butyl((4-methylcyclohex-3-en-1-yl)methoxy)diphenylsilane. $^1$H NMR (300 MHz, CD$_3$OD) δ 7.65-7.70 (m, 4H), 7.30-7.55 (m, 6H), 5.35 (br s, 1H), 3.35 (d, J=6.5 Hz, 2H), 1.70-2.30 (m, 5H), 1.62 (s, 3H), 1.22-1.43 (m, 2H), 1.05 (s, 9H).

Step 2: A 250 mL round bottom flask was charged with tert-butyl((4-methylcyclohex-3-en-1-yl)methoxy)diphenylsilane (5.00 g, 13.6 mmol) and THF (60 mL). BH$_3$.THF (20 mL, 20 mmol) was added dropwise at 0° C. and the reaction was stirred for 2 hours. 1 N aqueous NaOH (28 mL) was added to the reaction followed by 30% H$_2$O$_2$ in water (28 mL) at 0° C. The reaction was gradually warmed to room temperature and stirred for 16 hours. The reaction was then diluted with water and extracted using EtOAc. The organic layer was washed with water and brine, dried over anhydrous sodium sulfate, filtered, and concentrated. The residue was purified on a silica gel column (0 to 20% EtOAc/hexanes) to afford 5-(((tert-butyldiphenylsilyl)oxy)methyl)-2-methylcyclohexanol. $^1$H NMR (300 MHz, CD$_3$OD) δ 7.61-7.68 (m, 4H), 7.32-7.46 (m, 6H), 3.173.65 (m, 3H), 2.04 (m, 1H), 1.19-1.80 (m, 6H), 1.05 (d, J=6.4 Hz, 1.5H), 1.22-1.43 (m, 2H), 1.04 (s, 9H), 0.92 (d, J=6.4 Hz, 1.5H), 0.81-1.10 (m, 2H).

Step 3: A 250 mL round bottom flask was charged with 5-(((tert-butyldiphenylsilyl)oxy)methyl)-2-methylcyclohexanol (5.00 g, 13.3 mmol) and CH$_2$Cl$_2$ (170 mL). Dess-Martin periodinane (7.10 g, 17 mmol) was added portionwise at 0° C. The reaction was gradually warmed to room temperature and stirred for 16 hours. The reaction was filtered through celite and the filtrate was washed with saturated aqueous NaHCO$_3$ (50 mL), water and brine. The organic layer was dried over anhydrous sodium sulfate, filtered, and concentrated. The residue was purified on a silica gel column (0 to 20% EtOAc/hexanes) to afford 5-(((tert-butyldiphenylsilyl)oxy)methyl)-2-methylcyclohexanone as a mixture of diastereomers. This material was then dissolved in anhydrous methanol (50 mL) and NaOCH$_3$ (150 mg, 2.7 mmol) was added. The mixture was heated at 50° C. for 16 hours. The solvent was evaporated and the residue was suspended in EtOAc (200 mL), washed with water and brine and dried over anhydrous sodium sulfate. After concentration, the residue was purified on a silica gel column (0 to 20% EtOAc/hexanes) to afford trans-5-(((tert-butyldiphenylsilyl)oxy)methyl)-2-methylcyclohexanone. $^1$H NMR (300 MHz, CD$_3$OD) δ 7.62-7.68 (m, 4H), 7.34-7.43 (m, 6H), 3.53-3.59 (m, 2H), 1.83-2.51 (m, 6H), 1.56 (m, 1H), 1.36 (m, 1H), 1.05 (d, J=6.5 Hz, 3H), 1.04 (s, 9H).

Step 4: A 250 mL round bottom flask was charged with trans-5-4(tert-butyldiphenylsilyl)oxy)methyl)-2-methylcyclohexanone (4.20 g, 10.9 mmol) and toluene (100 mL). DAST (8.80 g, 54.8 mmol) was added and the reaction was heated at 50° C. for 4 hours. The reaction was cooled in an ice bath, saturated aqueous NaHCO$_3$ (50 mL) was added carefully, and the mixture was extracted using EtOAc (200 mL). The organic layer was washed with water and brine, dried over anhydrous sodium sulfate, filtered, and concentrated. The residue was purified on a silica gel column (0 to 20% EtOAc/hexanes) to afford tert-butyl((3,3-difluoro-4-methylcyclohexyl)methoxy)diphenylsilane. This compound was then dissolved in 3M HCl in methanol (20 mL) and heated in sealed tube at 50° C. for 16 hours. The solvent was evaporated and the residue was suspended in EtOAc (200 mL) and washed with saturated aqueous NaHCO$_3$ (50 mL), water and brine. The organic layer was dried over anhydrous sodium sulfate, filtered, and concentrated. The residue was purified on a silica gel column (0 to 20% EtOAc/hexanes) to afford (trans-3,3-difluoro-4-methylcyclohexyl)methanol. $^1$H NMR (300 MHz, CDCl$_3$) δ 3.48-3.59 (m, 2H), 2.19 (m, 1H), 1.89 (m, 1H), 1.70-1.80 (m, 3H), 1.2-1.40 (m, 2H), 1.05 (d, J=6.6 Hz, 3H), 0.90 (m, 1H).

Step 5: Following a procedure analogous to that described for the synthesis of Preparative Example 3.1 (Step 2), and starting with (trans-3,3-difluoro-4-methylcyclohexyl)methanol, trans-5-(bromomethyl)-1,1-difluoro-2-methylcyclohexane was prepared. $^1$H NMR (300 MHz, CDCl$_3$) δ 3.82 (dd, J=10.2, 3.3 Hz, 2H), 3.42-3.60 (m, 1H), 2.18-2.31 (m, 2H), 2.06-2.17 (m, 1H), 1.90-2.04 (m, 1H), 1.65-1.85 (m, 3H) 0.97 (d, J=6.6 Hz, 3H).

Preparative Example 3.7: 2,6-dichloro-7-(((trans)-3,3-difluoro-4-methylcyclohexyl)methyl)-7H-purine

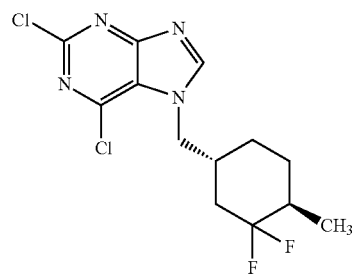 [SMILES: C[C@@H]1CC[C@@H](Cn2cnc3nc(Cl)nc(Cl)c32)CC1(F)F]

Following a procedure analogous to that described for the synthesis of Preparative Example 3.2, and starting with trans-5-(bromomethyl)-1,1-difluoro-2-methylcyclohexane and 3-methyl-1H-purine-2,6(3H,7H)-dione, 2,6-dichloro-7-(((trans)-3,3-difluoro-4-methylcyclohexyl)methyl)-7H-purine was prepared. $^1$H NMR (300 MHz, CDCl$_3$) δ 8.18 (s, 1H), 4.30-3.41 (m, 2H), 2.25 (m, 1H), 1.50-1.88 (m, 3H), 1.10-1.45 (m, 4H), 1.05 (d, J=6.5 Hz, 3H); MS (ES)=335 (M+1)$^+$.

Example 3.5: 3-(6-{[(1R)-1-cyclobutylethyl]amino}-7-{[(trans)-3,3-difluoro-4-methylcyclohexyl]methyl}-7H-purin-2-yl)-1,2,4-oxadiazol-5(4H)-one

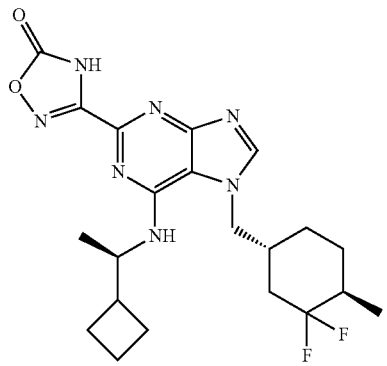 [SMILES: C[C@@H]1CC[C@@H](Cn2cnc3nc(-c4noc(=O)[nH]4)nc(N[C@H](C)C4CCC4)c32)CC1(F)F]

Following a procedure analogous to that described for the synthesis of Preparative Example 3.3 and Example 3.1, and starting with 2,6-dichloro-7-(((trans)-3,3-difluoro-4-methylcyclohexyl)methyl)-7H-purine (Preparative Example 3.7), 3-(6-{[(1R)-1-cyclobutylethyl]amino}-7-{[(trans)-3,3-difluoro-4-methylcyclohexyl]methyl}-7H-purin-2-yl)-1,2,4-oxadiazol-5(4H)-one was prepared. $^1$H NMR (300 MHz, CDCl$_3$) δ 8.17 (br s, 1H), 4.54-4.61 (m, 2H), 4.16-4.35 (m, 2H), 2.54 (m, 1H), 1.45-1.90 (m, 8H), 1.30-1.60 (m, 4H), 1.19 (d, J=5.6 Hz, 3H), 1.10-1.20 (m, 2H), 0.97 (d, J=7.2 Hz, 3H). MS (ES)=448 (M+1)$^+$.

Preparative Example 3.8: 2,6-dichloro-7-((3-fluoro-4-methylcyclohex-3-en-1-yl)methyl)-7H-purine

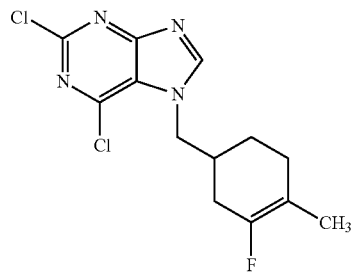 [SMILES: CC1=C(F)CC(Cn2cnc3nc(Cl)nc(Cl)c32)CC1]

Following a procedure analogous to that described for the synthesis of Preparative Example 3.2 (Step 1 and Step 2), and starting with trans-5-(bromomethyl)-1,1-difluoro-2-methylcyclohexane (Preparative Example 3.6) and 3-methyl-1H-purine-2,6(3H,7H)-dione, 2,6-dichloro-7-((3-fluoro-4-methylcyclohex-3-en-1-yl)methyl)-7H-purine was prepared as a byproduct in Step 2. $^1$H NMR (300 MHz, CDCl$_3$) δ 8.21 (s, 1H), 4.30-3.41 (m, 2H), 2.35 (m, 1H), 1.65-2.25 (m, 4H), 1.60 (s, 3H), 1.10-1.40 (m, 2H); MS (ES)=315 (M+1)$^+$.

Example 3.6: 3-(6-{[(1R)-1-cyclobutylethyl]amino}-7-[(3-fluoro-4-methylcyclohex-3-en-1-yl)methyl]-7H-purin-2-yl)-1,2,4-oxadiazol-5(4H)-one

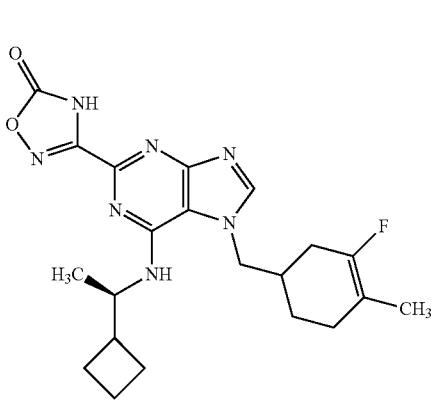 [SMILES: CC1=C(F)CC(Cn2cnc3nc(-c4noc(=O)[nH]4)nc(N[C@H](C)C4CCC4)c32)CC1]

Following a procedure analogous to that described for the synthesis of Preparative Example 3.3 and Example 3.1, and starting with 2,6-dichloro-7-((3-fluoro-4-methylcyclohex-3-en-1-yl)methyl)-7H-purine (Preparative Example 3.8), 3-(6-{[(1R)-1-cyclobutylethyl]amino}-7-[(3-fluoro-4-methylcyclohex-3-en-1-yl)methyl]-7H-purin-2-yl)-1,2,4-oxadiazol-5(4H)-one (mixture of diastereomers) was prepared. $^1$H NMR (400 MHz, CD$_3$OD) δ 8.19 (d, J=1.6 Hz, 1H), 4.73-4.80 (m, 1H), 4.52-4.64 (m, 1H), 4.26-4.38 (m, 1H), 2.45-2.60 (m, 1H), 1.68-2.20 (m, 12H), 1.57 (br s, 3H), 1.27-1.43 (m, 1H), 1.19 (d, J=6.4 Hz, 3H). MS (ES)=428 (M+1)$^+$.

Preparative Example 3.9: trans-methyl 4-(bromomethyl)cyclohexanecarboxylate

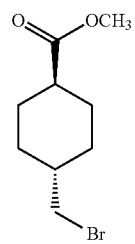 [SMILES: COC(=O)[C@H]1CC[C@H](CBr)CC1]

Following a procedure analogous to that described for the synthesis of Preparative Example 3.1 (Step 2), and starting with trans-methyl 4-(hydroxymethyl)cyclohexanecarboxylate, trans-methyl 4-(bromomethyl)cyclohexanecarboxylate was prepared. $^1$H NMR (300 MHz, CDCl$_3$) δ 3.67 (s, 3H), 3.28 (d, J=6.3 Hz, 2H), 2.17-2.33 (m, 1H), 1.81-2.09 (m, 4H), 1.54-1.73 (m, 1H), 1.35-1.52 (m, 2H), 0.91-1.14 (m, 2H).

Preparative Example 3.10: trans-methyl-4-((2,6-dichloro-7H-purin-7-yl)methyl)cyclohexanecarboxylate

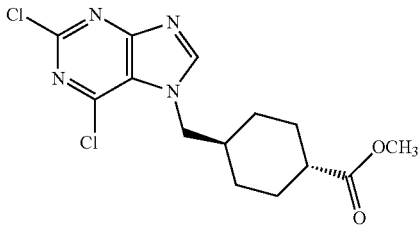 [SMILES: COC(=O)[C@H]1CC[C@H](Cn2cnc3nc(Cl)nc(Cl)c32)CC1]

Following a procedure analogous to that described for the synthesis of Preparative Example 3.2 (Step1 and Step 2), and starting with trans-methyl 4-(bromomethyl)cyclohexanecarboxylate and 3-methyl-1H-purine-2,6(3H,9H)-dione, trans-methyl-4-((2,6-dichloro-7H-purin-7-yl)methyl)cyclohexanecarboxylate was prepared. $^1$H NMR (300 MHz, CDCl$_3$) δ 8.18 (s, 1H), 4.29 (d, J=7.2 Hz, 2H), 3.67 (s, 3H), 2.21-2.36 (m, 1H), 2.05-2.11 (m, 1H), 1.82-1.95 (m, 1H), 1.67-1.81 (m, 2H), 1.32-1.52 (m, 2H), 1.01-1.22 (m, 3H). MS (ES)=343 (M+1)$^+$.

Preparative Example 3.11: (R)-6-((1-cyclobutylethyl)amino)-7-((4-methylenecyclohexyl)methyl)-7H-purine-2-carbonitrile

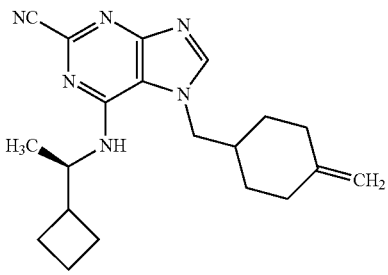 [SMILES: C=C1CCC(Cn2cnc3nc(C#N)nc(N[C@H](C)C4CCC4)c32)CC1]

Step 1: Following a procedure analogous to that described for the synthesis of Preparative Example 3.3 (Step 1) and starting with trans-methyl-4-((2,6-dichloro-7H-purin-7-yl)methyl)cyclohexanecarboxylate (Preparative Example 3.10), trans-methyl-4-((2-chloro-6-4(R)-1-cyclobutylethyl)amino)-7H-purin-7-yl)methyl)cyclohexanecarboxylate was prepared. $^1$H NMR (300 MHz, CDCl$_3$) δ 7.75 (s, 1H), 4.52 (d, J=8.1 Hz, 1H), 4.34-4.50 (m, 1H), 4.07 (dd, J=15.0, 6.0 Hz, 1H), 3.98 (dd, J=15.0, 7.5 Hz, 1H), 3.66 (s, 3H), 2.19-2.48 (m, 2H), 1.95-2.16 (m, 4H), 1.81-1.94 (m, 4H), 1.61-1.79 (m, 3H), 1.25-1.51 (m, 2H), 1.20 (d, J=6.3 Hz, 3H), 0.94-1.08 (m, 2H). MS (ES)=406 (M+1)$^+$.

Step 2: To a solution of trans-methyl-4-((2-chloro-6-(((R)-1-cyclobutylethyl)amino)-7H-purin-7-yl)methyl)cyclohexanecarboxylate (500 mg, 1.29 mmol) in THF (10 mL) at −78° C. was added LiAlH$_4$ (1.0 M solution in THF, 2.6 mL, 2.6 mmol) dropwise. The reaction was stirred at −78° C. for 1 hour under a nitrogen atmosphere. Next, NaOH (10% aqueous solution; 0.5 mL) was added to the reaction mixture followed by water (0.7 mL). The resulting mixture was stirred at room temperature until the sticky white residue settled. The mixture was filtered under vacuum through a pad of celite and the filter cake was washed with. The filtrate was concentrated to afford crude (trans-4-((2-chloro-6-(((R)-1-cyclobutylethyl)amino)-7H-purin-7-yl)methyl)cyclohexyl)methanol. The crude material was used for the next step without purification. $^1$H NMR (400 MHz, CDCl$_3$) δ 7.77 (s, 1H), 4.51 (br d, J=8.0 Hz, 1H), 4.37-4.47 (m, 1H), 4.05 (dd, J=14.8, 6.0 Hz, 1H), 3.97 (dd, J=14.8, 7.6 Hz, 1H), 3.43-3.50 (m, 2H), 2.35-2.47 (m, 1H), 1.98-2.13 (m, 2H), 1.81-1.97 (m, 6H), 1.59-1.78 (m, 3H), 1.25-1.34 (m, 2H), 1.20 (d, J=6.0 Hz, 3H), 0.85-1.16 (m, 4H). MS (ES)=378 (M+1)$^+$.

Step 3: To a solution of (trans-4-((2-chloro-6-(((R)-1-cyclobutylethyl)amino)-7H-purin-7-yl)methyl)cyclohexyl)methanol (285 mg, 0.75 mmol) in dichloromethane (5.0 mL), was added pyridine (179 mg, 2.26 mmol) and 4-toluenesulfonyl chloride (186 mg, 0.98 mmol) at 0° C. under a nitrogen atmosphere. The reaction was slowly warmed to room temperature and stirring was continued for 2 hours. The reaction mixture was cooled on an ice bath and quenched with water (5 mL) and extracted with dichloromethane (3×15 mL). The combined organic layers were washed with brine (10 mL), dried over anhydrous Na$_2$SO$_4$, filtered and concentrated to afford crude (trans-4-((2-chloro-6-(((R)-1-cyclobutylethyl)amino)-7H-purin-7-yl)methyl)cyclohexyl)methyl 4-methylbenzenesulfonate. The crude material was used for the next step without purification. $^1$H NMR (400 MHz, CDCl$_3$) δ 7.76 (d, J=8.4 Hz, 2H), 7.75 (s, 1H), 7.33 (d, J=8.4 Hz, 2H), 4.35-4.49 (m, 2H), 4.03 (dd, J=14.4, 6.4 Hz, 1H), 3.95 (dd, J=14.4, 7.2 Hz, 1H), 3.82 (d, J=6.4 Hz, 2H), 2.44 (s, 3H), 2.32-2.44 (m, 1H), 2.04-2.15 (m, 1H), 1.89-2.03 (m, 2H), 1.75-1.89 (m, 4H), 1.48-1.73 (m, 2H), 1.16-1.23 (m, 1H), 1.19 (d, J=6.4 Hz, 3H), 0.81-1.12 (m, 6H). MS (ES)=532 (M+1)$^+$.

Step 4: To a solution of (trans-4-((2-chloro-6-(((R)-1-cyclobutylethyl)amino)-7H-purin-7-yl)methyl)cyclohexyl)methyl 4-methylbenzenesulfonate (400 mg, 0.75 mmol) in acetone (15 mL), was added sodium iodide (339 mg, 2.26 mmol) at room temperature under a nitrogen atmosphere. The resulting reaction mixture was heated at reflux for 12 hours. The reaction was then cooled to room temperature and concentrated under reduced pressure. The resulting residue was diluted with water (10 mL) and extracted with dichloromethane (2×15 mL). The combined organic layers were washed with brine (10 mL), dried over anhydrous Na$_2$SO$_4$, filtered, and concentrated to afford crude 2-chloro-N—((R)-1-cyclobutylethyl)-7-((trans-4-(iodomethyl)cyclohexyl)methyl)-7H-purin-6-amine. The crude material was used in the next step without purification. MS (ES)=488 (M+1)$^+$.

Step 5: To a solution of 2-chloro-N—((R)-1-cyclobutylethyl)-7-((trans-4-(iodomethyl)cyclohexyl)methyl)-7H-purin-6-amine (341 mg, 0.70 mmol) in dimethoxyethane (5.0 mL), was added potassium tert-butoxide (235 mg, 2.10 mmol) under a nitrogen atmosphere. The resulting reaction mixture was heated at 80° C. with stirring for 10 hours. The reaction mixture was then cooled to room temperature, quenched with water (10 mL), and extracted with methylene chloride (3×15 mL). The combined organic layers were dried over anhydrous Na$_2$SO$_4$, filtered, concentrated. The residue was purified on a silica gel column (0 to 10% MeOH/CH$_2$Cl$_2$) to afford (R)-2-chloro-N-(1-cyclobutylethyl)-7-((4-methylenecyclohexyl)methyl)-7H-purin-6-amine. $^1$H NMR (300 MHz, CDCl$_3$) δ 7.77 (s, 1H), 4.68 (s, 2H), 4.50-4.61 (m, 1H), 4.35-4.49 (m, 1H), 4.08 (dd, J=15.0, 6.0 Hz, 1H), 3.98 (dd, J=15.0, 7.8 Hz, 1H), 2.29-2.48 (m, 3H), 1.56-2.14 (m, 11H), 1.02-1.24 (m, 2H), 1.20 (d, J=6.6 Hz, 3H). MS (ES)=360 (M+1)$^+$.

Step 6: Following a procedure analogous to that described for the synthesis of Preparative Example 3.3 (Step 2) and starting with (R)-2-chloro-N-(1-cyclobutylethyl)-7-((4-methylenecyclohexyl)methyl)-7H-purin-6-amine, (R)-6-((1-cyclobutylethyl)amino)-7-((4-methylenecyclohexyl)methyl)-7H-purine-2-carbonitrile was prepared. $^1$H NMR (400 MHz, CDCl$_3$) δ 7.90 (s, 1H), 4.72 (d, J=8.0 Hz, 1H), 4.69 (s, 2H), 4.40-4.51 (m, 1H), 4.15 (dd, J=14.8, 6.0 Hz, 1H), 4.05 (dd, J=14.8, 8.0 Hz, 1H), 2.31-2.50 (m, 3H), 2.06-2.15 (m, 1H), 1.72-2.04 (m, 9H), 1.60-1.69 (m, 1H), 1.08-1.24 (m, 2H), 1.21 (d, J=6.4 Hz, 3H). MS (ES)=351 (M+1)$^+$.

Example 3.7: 3-(6-{[(1R)-1-cyclobutylethyl]amino}-7-[(4-methylidenecyclohexyl)methyl]-7H-purin-2-yl)-1,2,4-oxadiazol-5(4H)-one

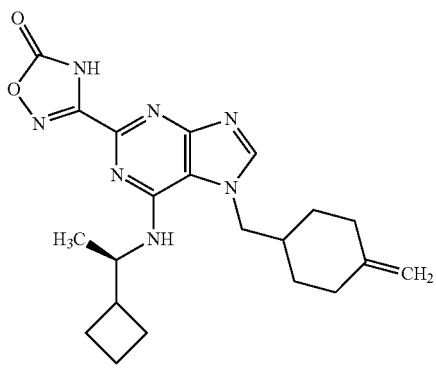 [SMILES: C=C1CCC(Cn2cnc3nc(-c4noc(=O)[nH]4)nc(N[C@H](C)C4CCC4)c32)CC1]

Using a procedure described for the preparation of oxadiazolone (Example 1.7, Step 1 and Step 2) and starting with (R)-6-((1-cyclobutylethyl)amino)-7-((4-methylenecyclohexyl)methyl)-7H-purine-2-carbonitrile (Preparative Example 3.11), 3-(6-{[(1R)-1-cyclobutylethyl]amino}-7-[(4-methylidenecyclohexyl)methyl]-7H-purin-2-yl)-1,2,4-oxadiazol-5(4H)-one was prepared. $^1$H NMR (300 MHz, DMSO-d$_6$) δ 12.88 (br s, 1H), 8.32 (s, 1H), 6.43 (d, J=8.4 Hz, 1H), 4.46-4.69 (m, 2H), 4.60 (s, 2H), 4.22 (dd, J=14.4, 8.7 Hz, 1H), 2.42-2.61 (m, 1H), 2.13-2.34 (m, 2H), 1.61-2.09 (m, 10H), 0.92-1.38 (m, 3H), 1.13 (d, J=6.3 Hz, 3H). MS (ES)=410 (M+1)$^+$.

Example 3.8: 6-{[(1R)-1-cyclobutylethyl]amino}-7-[(4-methylidenecyclohexyl)methyl]-7H-purine-2-carboxylic acid

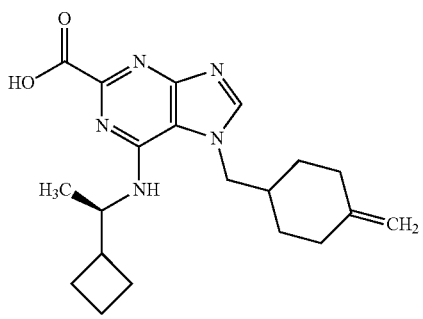 [SMILES: C=C1CCC(Cn2cnc3nc(C(=O)O)nc(N[C@H](C)C4CCC4)c32)CC1]

Using a procedure analogous to that described in Example 1.1 and starting with (R)-6-((1-cyclobutylethyl)amino)-7-((4-methylenecyclohexyl)methyl)-7H-purine-2-carbonitrile (Preparative Example 3.11), 6-{[(1R)-1-cyclobutylethyl]amino}-7-[(4-methylidenecyclohexyl)methyl]-7H-purine-2-carboxylic acid. $^1$H NMR (300 MHz, DMSO-d$_6$) δ 12.71 (br s, 1H), 8.31 (s, 1H), 6.36 (d, J=8.1 Hz, 1H), 4.53-4.69 (m, 1H), 4.63 (s, 2H), 4.38-4.52 (m, 1H), 4.21 (dd, J=14.4, 8.4 Hz, 1H), 2.43-2.68 (m, 1H), 2.14-2.33 (m, 2H), 1.60-2.11 (m, 10H), 1.22-1.37 (m, 1H), 0.89-1.18 (m, 2H), 1.13 (d, J=6.3 Hz, 3H). MS (ES)=370 (M+1)$^+$.

Example 3.9: 3-(6-{[(1R)-1-cyclobutylethyl]amino}-7-[(3-methylcyclopentyl)methyl]-7H-purin-2-yl)-1,2,4-oxadiazol-5(4H)-one

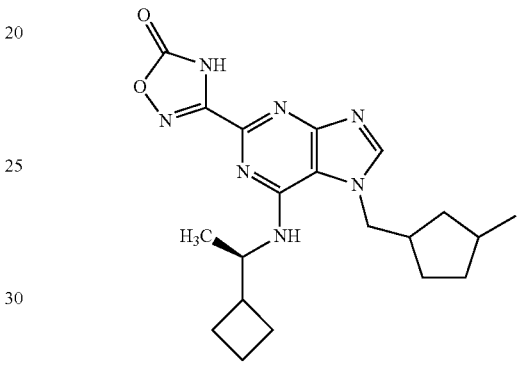

Following a procedure analogous to that described for the synthesis of Preparative Example 3.2 (Steps 1 and 2), Preparative Example 3.3 (Steps 1 and 2), and Example 3.1 (Steps 1 and 2), and starting with 1-(bromomethyl)-3-methylcyclopentane, 3-(6-{[(1R)-1-cyclobutylethyl]amino}-7-[(3-methylcyclopentyl)methyl]-7H-purin-2-yl)-1,2,4-oxadiazol-5(4H)-one (mixture of diastereomers) was prepared. $^1$H NMR (400 MHz, CD$_3$OD) δ 8.31 (s, 1H), 4.51-4.74 (m, 2H), 4.18-4.40 (m, 1H), 2.57 (m, 1H), 2.41 (m, 1H), 1.98-2.21 (m, 3H), 1.81-1.98 (m, 6H), 1.73 (m, 1H), 1.52 (m, 2H), 1.20 (d, J=6.4 Hz, 3H), 1.12 (m, 1H), 0.92-1.04 (m, 3H). MS (ES)=398 (M+1)$^+$.

Preparative Example 3.12: 1-(bromomethyl)-3-ethylcyclopentane

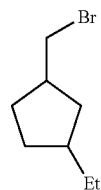

Step 1: To a stirred solution of 3-ethylcyclopentanone (4.00 g, 35.7 mmol) in THF (70 mL) was added LDA (2 M in THF, 22.8 mL, 46.4 mmol) at −78° C. and the reaction was stirred at that temperature for 30 minutes. Next, N-phenyl-bis(trifluoromethanesulfonimide) (14.0 g, 39.2 mmol) in THF (70 mL) was added at −78° C. The mixture was allowed to warm to room temperature and stirred for 17 hours under a nitrogen atmosphere. The reaction mixture was then cooled to 0° C. and slowly quenched with aqueous ammonium chloride and extracted with methyl tertiary-butyl ether (3×30 mL). The combined organic layers were washed with brine (2×30 mL), dried over anhydrous $Na_2SO_4$, and concentrated. Purification of the residue on a silica gel column (10 to 100% EtOAc/hexanes) afforded 3-ethylcyclopent-1-en-1-yl trifluoromethanesulfonate. $^1$H NMR (400 MHz, $CDCl_3$) δ 5.57 (m, 1H), 2.67 (m, 1H), 2.50-2.58 (m, 2H), 2.17-2.35 (m, 2H), 1.37-1.50 (m, 2H), 0.91 (t, J=7.6 Hz, 3H). MS (ES)=245 (M+1)$^+$.

Step 2: To a stirred solution of 3-ethylcyclopent-1-en-1-yl trifluoromethanesulfonate (1.0 g, 4.08 mmol) in methanol (15 mL) and DMF (10 mL) was added $Pd(OAc)_2$ (45 mg, 0.20 mmol), 1,1'-bis(diphenylphosphino)ferrocene (226 mg, 0.40 mmol) and $Et_3N$ (2.3 mL, 16.3 mmol). The mixture was degassed with CO for 15 minutes and then stirred at room temperature under CO atmosphere (balloon) for 16 hours. Next, water was added to the reaction mixture and it was extracted with methyl tertiary-butyl ether (3×30 mL). The combined organic layers were washed with brine, dried over $Na_2SO_4$, and concentrated. Purification of the residue on a silica gel column (0 to 100% EtOAc/hexanes) afforded methyl 3-ethylcyclopent-1-enecarboxylate.

Step 3: To a stirred solution of methyl 3-ethylcyclopent-1-enecarboxylate (1.60 g, 10.3 mmol) in methanol (15 mL) was added 10% Pd on carbon (100 mg) and the mixture was purged with hydrogen for 10 minutes. Then reaction mixture was then stirred at room temperature for 16 hours under a hydrogen atmosphere (balloon). The reaction mixture was then filtered through a pad of celite, washing the pad with methanol, and the filtrate was to afford crude methyl 3-ethylcyclopentanecarboxylate. $^1$H NMR (400 MHz, $CDCl_3$) δ 3.66 (s, 3H), 2.59-2.85 (m, 1H), 2.65 (q, J=7.6 Hz, 2H), 1.70-1.91 (m, 2H), 1.32-1.48 (m, 1H), 1.20-1.30 (m, 4H), 1.24 (t, J=6.4 Hz, 3H).

Step 4: To a stirred solution of methyl 3-ethylcyclopentanecarboxylate (1.50 g, 9.61 mmol) in THF (10 mL) was added LAH (1 M in THF; 9.6 mL, 9.6 mmol) at 0° C., and the reaction mixture was stirred at 0° C. for 1 hour. The reaction mixture was quenched with saturated $Na_2SO_4$ and filtered through a pad of celite, washing the pad with ethyl acetate. The filtrate was concentrated to dryness to afford crude (3-ethylcyclopentyl)methanol. $^1$H NMR (300 MHz, $CDCl_3$) δ 3.51 (d, J=6.9 Hz, 1H), 3.49 (d, J=7.2 Hz, 1H), 2.11 (m, 1H), 1.65-1.85 (m, 2H), 1.54 (m, 1H), 1.14-1.34 (m, 6H), 0.85-0.91 (m, 3H).

Step 5: To a stirred solution of (3-ethylcyclopentyl)methanol (1.80 g, 14.1 mmol) in dichloromethane (18 mL) was added triphenylphosphine (4.42 g, 16.9 mmol). The reaction mixture was cooled to 0° C. and $CBr_4$ (5.59 g, 16.9 mmol) was added. After the addition was complete, the reaction mixture was warmed to room temperature and stirred for 12 hours. The reaction mixture was then concentrated and the residue was purified on a silica gel column (10 to 100% EtOAc/hexanes) to afford 1-(bromomethyl)-3-ethylcyclopentane. $^1$H NMR (400 MHz, $CDCl_3$) δ 3.38 (d, J=6.8 Hz, 1H), 3.36 (d, J=6.8 Hz, 1H), 2.31 (m, 1H), 2.05 (m, 1H), 1.77-1.91 (m, 2H), 1.15-1.47 (m, 6H), 0.85-0.90 (m, 3H).

Example 3.10: 3-(6-(((R)-1-cyclobutylethyl)amino)-7-((3-ethylcyclopentyl)methyl)-7H-purin-2-yl)-1,2,4-oxadiazol-5(4H)-one

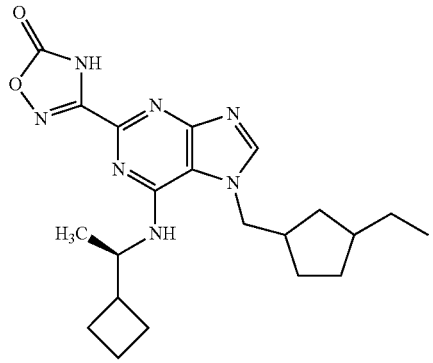 [SMILES: CCC1CCC(Cn2cnc3nc(-c4noc(=O)[nH]4)nc(N[C@H](C)C4CCC4)c32)C1]

Following a procedure analogous to that described for the synthesis of Preparative Example 3.2, Preparative Example 3.3 and Example 3.1, and starting with 1-(bromomethyl)-3-ethylcyclopentane (Preparative Example 3.12), 3-(6-(((R)-1-cyclobutylethyl)amino)-7-((3-ethylcyclopentyl)methyl)-7H-purin-2-yl)-1,2,4-oxadiazol-5(4H)-one was prepared as a mixture of diastereomers. $^1$H NMR (400 MHz, $CD_3OD$) δ 8.30 (br s, 1H), 4.65-4.72 (m, 2H), 4.32 (m, 1H), 2.62 (m, 1H), 2.30-2.45 (m, 1H), 1.60-2.15 (m, 8H), 1.66-1.22 (m, 7H), 1.21 (d, J=8.0 Hz, 3H), 0.85-0.95 (m, 3H). MS (ES) =412 (M+1)$^+$.

Preparative Example 3.13: 1-((trans)-4-methylcyclohexyl) ethanone

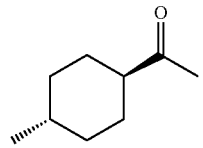

Step 1: Dess-Martin periodinane (49.7 g, 117 mmol) was added in several portions to a 0° C. solution of (trans-4-methylcyclohexyl)methanol (Preparative Example 1.2, Step 1; 10.0 g, 78.1 mmol) in $CH_2Cl_2$ (200 mL). The reaction was then warmed to room temperature and stirred at room temperature for 5 hours. Saturated aqueous $NaHCO_3$ solution and aqueous $Na_2S_2O_3$ solution were added to quench the reaction. The two layers were separated, and the organic layer was washed with brine, dried over $Na_2SO_4$, filtered, and concentrated in vacuo to afford (trans)-4-methylcyclohexanecarbaldehyde. Step 2: $CH_3MgBr$ (3 M in THF, 47.6 mL, 143 mmol) was added dropwise to a 0° C. solution of (trans)-4-methylcyclohexanecarbaldehyde (6.00 g, 47.6 mmol) in THF (150 mL). After the addition was complete, the reaction was warmed to room temperature and stirred for 2 hours. Saturated aqueous $NH_4Cl$ solution was added to quench the reaction. The two layers were separated and the aqueous layer was extracted with EtOAc (3×50 mL). The combined organic layers were washed with brine, dried over $Na_2SO_4$, filtered, and concentrated in vacuo. Purification of the residue on a silica gel column with 0 to 10% EtOAc/hexanes afforded 1-((trans)-4-methylcyclohexyl)ethanol.

Step 3: Using a procedure analogous to that described in Step 1, and starting with 1-((trans)-4-methylcyclohexyl)ethanol, 1-((trans)-4-methylcyclohexyl) ethanone was prepared. $^1$H NMR (300 MHz, CDCl$_3$) δ 2.26 (m, 1H), 2.14 (s, 3H), 1.87-1.92 (m, 2H), 1.76-1.80 (m, 2H), 1.27-1.39 (m, 3H), 0.83-1.01 (m, 2H), 0.89 (d, J=6.6 Hz, 3H).

Preparative Example 3.14: 2,6-dichloro-7-(1-((trans)-4-methylcyclohexyl)ethyl)-7H-purine

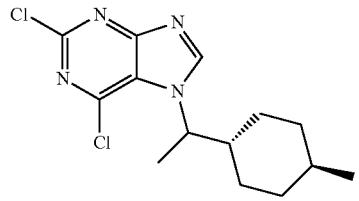 [SMILES: CC([C@H]1CC[C@H](C)CC1)n1cnc2nc(Cl)nc(Cl)c21]

Step 1: Acetic acid (5 mL) was added to a suspension of 6-amino-1-methylpyrimidine-2,4(1H,3H)-dione (5.00 g, 35 mmol) in water (80 mL). The reaction mixture was cooled to −5° C. and NaNO$_2$ (2.70 g, 39 mmol) was added in several portions. After the addition was complete, the reaction was warmed to room temperature and stirred at room temperature overnight. The purple solid was collected by filtration, washed with water, and dried in vacuo, to afford 6-amino-1-methyl-5-nitrosopyrimidine-2,4(1H,3H)-dione. MS (APCI)=171 (M+1)$^+$.

Step 2: Na$_2$S$_2$O$_4$ (13.0 g, 74.1 mmol) was added in several portions to a suspension of 6-amino-1-methyl-5-nitrosopyrimidine-2,4(1H,3H)-dione (4.20 g, 24.7 mmol) in saturated ammonium hydroxide solution (42 mL) at 30° C. After the addition was complete, the reaction was warmed to 50° C. and stirred for 2 hours. The reaction was then cooled to room temperature. The solid was collected by filtration, washed with water, and dried in vacuo to afford 5,6-diamino-1-methylpyrimidine-2,4(1H,3H)-dione. MS (APCI)=157 (M+1)$^+$.

Step 3: To a mixture of 1-((trans)-4-methylcyclohexyl)ethanone (Preparative Example 3.13; 1.20 g, 7.69 mmol) and 5,6-diamino-1-methylpyrimidine-2,4(1H,3H)-dione (1.18 g, 8.46 mmol) in MeOH (30 mL) was added acetic acid (73 µL, 1.28 mmol), followed by NaCNBH$_3$ (1.35 g, 21.5 mmol). The reaction was heated at 50° C. overnight. The reaction was then concentrated in vacuo and water was added. The crude solid was collected by filtration, washed with saturated aqueous NaHCO$_3$ solution and water, and dried in vacuo to afford crude 6-amino-1-methyl-5-((1-((trans)-4-methylcyclohexyl)ethyl)amino)pyrimidine-2,4(1H,3H)-dione, which was used in next step without purification. MS (APCI)=281 (M+1)$^+$.

Step 4: Crude 6-amino-1-methyl-5-((1-((trans)-4-methylcyclohexyl)ethyl)amino)pyrimidine-2,4(1H,3H)-dione (900 mg, 3.21 mmol) in triethyl orthoformate (30 mL) was heated at 150° C. for 4 hours. The reaction was then cooled to room temperature and concentrated in vacuo to afford 3-methyl-7-(1-((trans)-4-methylcyclohexyl)ethyl)-1H-purine-2,6(3H,7H)-dione, which was used in next step without further purification. MS (APCI)=291 (M+1)$^+$.

Step 5: DBU (2.3 mL, 15.4 mmol) was added dropwise to a suspension of crude 3-methyl-7-(1-((trans)-4-methylcyclohexyl)ethyl)-1H-purine-2,6(3H,7H)-dione (900 mg, 3.09 mmol) in POCl$_3$ (5 mL) at room temperature. After the addition was complete, the reaction was heated at 120° C. for 2 hours and then cooled to room temperature. Ice water was added and the mixture was extracted with EtOAc (3×15 mL). The combined organic layers were washed with brine, dried over Na$_2$SO$_4$, and concentrated in vacuo. Purification of the residue on a silica gel column with 0 to 40% EtOAc/hexanes afforded 2,6-dichloro-7-(1-((trans)-4-methylcyclohexyl)ethyl)-7H-purine. $^1$H NMR (400 MHz, CDCl$_3$) δ 8.33 (s, 1H), 4.94 (dq, J=6.8, 6.8 Hz, 1H), 1.67-1.79 (m, 4H), 1.64 (d, J=6.8 Hz, 3H), 1.26-1.42 (m, 4H), 0.81-0.96 (m, 2H), 0.87 (d, J=6.6 Hz, 3H). MS (APCI)=313 (M+1)$^+$.

Example 3.17: 3-(6-{[(1R)-1-cyclobutylethyl]amino}-7-[1-(trans-4-methylcyclohexyl)ethyl]-7H-purin-2-yl)-1,2,4-oxadiazol-5(4H)-one (diastereomer 1)

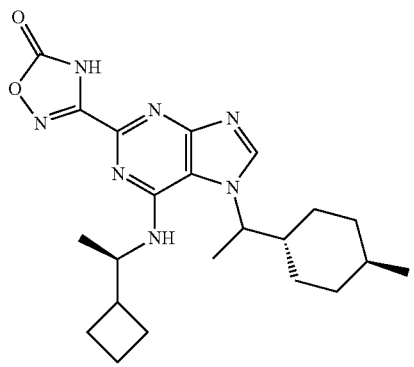 [SMILES: CC([C@H]1CC[C@H](C)CC1)n1cnc2nc(-c3noc(=O)[nH]3)nc(N[C@H](C)C3CCC3)c21]

Step 1: To a solution of 2,6-dichloro-7-(1-((trans)-4-methylcyclohexyl)ethyl)-7H-purine (Preparative Example 3.14; 260 mg, 0.83 mmol) in IPA (10 mL) was added (R)-1-cyclobutylethanamine hydrochloride (253 mg, 2.08 mmol), followed by the addition of DIEA (0.58 mL, 3.53 mmol) at room temperature. The reaction was heated at 85° C. for 15 hours and then cooled to room temperature and concentrated in vacuo. Purification of the residue on a silica gel column with 0 to 80% EtOAc/hexanes afforded separation of the two diastereomers of 2-chloro-N—((R)-1-cyclobutylethyl)-7-(1-((trans)-4-methylcyclohexyl)ethyl)-7H-purin-6-amine MS (APCI)=376 (M+1)$^+$.

Steps 2-4: Using procedures similar to those described in Preparative Example 3.3 (Step 1) and Example 2.1 (Steps 1 and 2), the faster eluting diastereomer of 2-chloro-N4R)-1-cyclobutylethyl)-7-(1-((trans)-4-methylcyclohexyl)ethyl)-7H-purin-6-amine was converted to 3-(6-{[(1R)-1-cyclobutylethyl]amino}-7-[1-(trans-4-methylcyclohexyl)ethyl]-7H-purin-2-yl)-1,2,4-oxadiazol-5(4H)-one (diastereomer 1). $^1$H NMR (400 MHz, CDCl$_3$) δ 8.64 (s, 1H), 4.76 (d, J=8.0 Hz, 1H), 4.62 (dq, J=13.6, 6.8 Hz, 1H), 4.25 (dq, J=6.8, 6.8 Hz, 1H), 2.45 (m, 1H), 1.98-2.13 (m, 2H), 1.83-1.96 (m, 4H), 1.72 (d, J=6.8 Hz, 3H), 1.66-1.79 (m, 3H), 1.28-1.37 (m, 2H), 1.26 (d, J=6.8 Hz, 3H), 1.06-1.17 (m, 2H), 0.87 (d, J=6.8 Hz, 3H), 0.80-0.91 (m, 3H). MS (ES)=426 (M+1)$^+$.

The compounds in Table 3 have been described above or were prepared using procedures similar to those described above.

TABLE 3

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.1 | 116.1 | 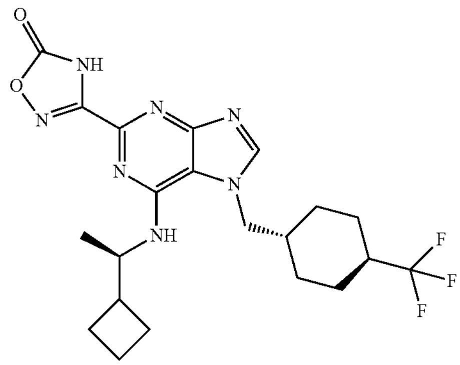 [SMILES: C[C@@H](Nc1nc(-c2noc(=O)[nH]2)nc2ncn(C[C@H]3CC[C@H](C(F)(F)F)CC3)c12)C1CCC1] | 3-(6-{[(1R)-1-cyclobutylethyl]amino}-7-{[trans-4-(trifluoromethyl)cyclohexyl]methyl}-7H-purin-2-yl)-1,2,4-oxadiazol-5(4H)-one | | 466 | 466 |
| 3.2 | 437.3 | 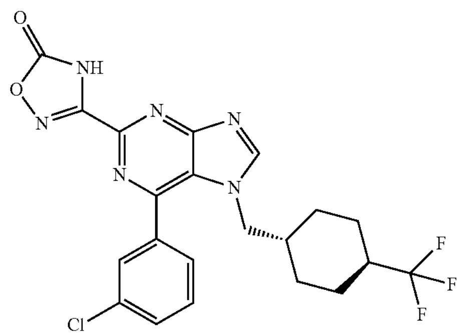 [SMILES: O=c1[nH]c(-c2nc(-c3cccc(Cl)c3)c3c(ncn3C[C@H]3CC[C@H](C(F)(F)F)CC3)n2)no1] | 3-[6-(3-chlorophenyl)-7-{[trans-4-(trifluoromethyl)cyclohexyl]methyl}-7H-purin-2-yl]-1,2,4-oxadiazol-5(4H)-one | | 479 | 479 |
| 3.3 | 1429 | 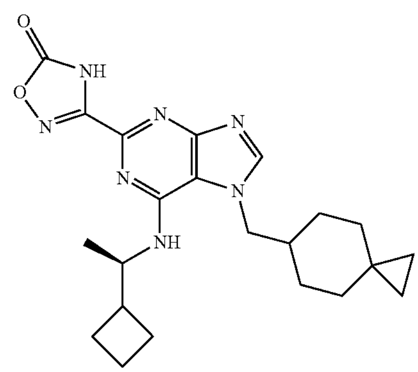 [SMILES: C[C@@H](Nc1nc(-c2noc(=O)[nH]2)nc2ncn(CC3CCC4(CC3)CC4)c12)C1CCC1] | 3-[6-{[(1R)-1-cyclobutylethyl]amino}-7-(spiro[2.5]oct-6-ylmethyl)-7H-purin-2-yl]-1,2,4-oxadiazol-5(4H)-one | | 424 | 424 |
| 3.4 | 2702 | 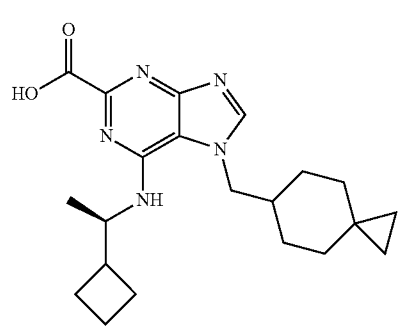 [SMILES: C[C@@H](Nc1nc(C(=O)O)nc2ncn(CC3CCC4(CC3)CC4)c12)C1CCC1] | 6-{[(1R)-1-cyclobutylethyl]amino}-7-(spiro[2.5]oct-6-ylmethyl)-7H-purine-2-carboxylic acid | | 384 | 384 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.5 | 198.4 | 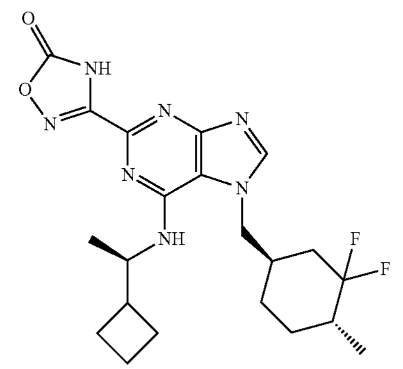 [SMILES: C[C@@H]1CC[C@@H](Cn2cnc3nc(-c4noc(=O)[nH]4)nc(N[C@H](C)C4CCC4)c32)CC1(F)F] | 3-(6-{[(1R)-1-cyclobutylethyl]amino}-7-{[(trans)-3,3-difluoro-4-methylcyclohexyl]methyl}-7H-purin-2-yl)-1,2,4-oxadiazol-5(4H)-one | | 448 | 448 |
| 3.6 | 149.3 | 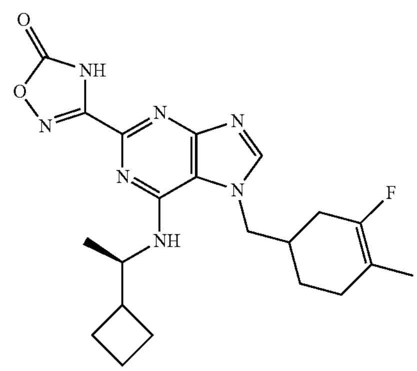 [SMILES: CC1=C(F)CC(Cn2cnc3nc(-c4noc(=O)[nH]4)nc(N[C@H](C)C4CCC4)c32)CC1] | 3-(6-{[(1R)-1-cyclobutylethyl]amino}-7-[(3-fluoro-4-methylcyclohex-3-en-1-yl)methyl]-7H-purin-2-yl)-1,2,4-oxadiazol-5(4H)-one | | 428 | 428 |
| 3.7 | 543 | 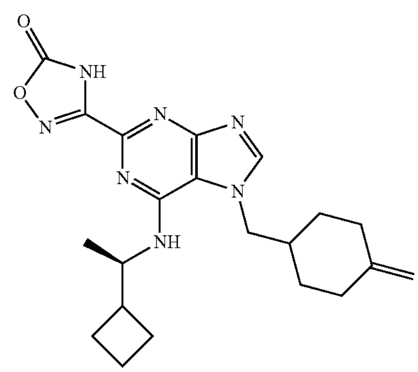 [SMILES: C=C1CCC(Cn2cnc3nc(-c4noc(=O)[nH]4)nc(N[C@H](C)C4CCC4)c32)CC1] | 3-(6-{[(1R)-1-cyclobutylethyl]amino}-7-[(4-methylidenecyclohexyl)methyl]-7H-purin-2-yl)-1,2,4-oxadiazol-5(4H)-one | | 410 | 410 |
| 3.8 | 677.3 | 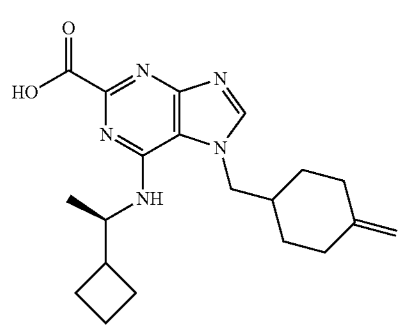 [SMILES: C=C1CCC(Cn2cnc3nc(C(=O)O)nc(N[C@H](C)C4CCC4)c32)CC1] | 6-{[(1R)-1-cyclobutylethyl]amino}-7-[(4-methylidenecyclohexyl)methyl]-7H-purine-2-carboxylic acid | | 370 | 370 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.9 | 1637 | 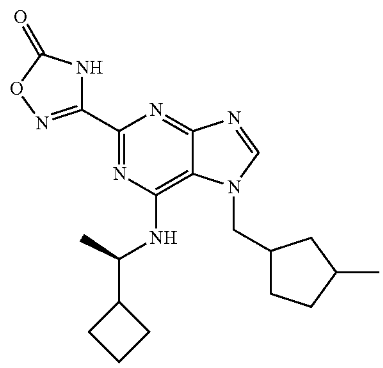 [SMILES: CC1CCC(Cn2cnc3nc(-c4noc(=O)[nH]4)nc(N[C@H](C)C4CCC4)c32)C1] | 3-(6-{[(1R)-1-cyclobutylethyl]amino}-7-[(3-methylcyclopentyl)methyl]-7H-purin-2-yl)-1,2,4-oxadiazol-5(4H)-one (mixture of diastereomers) | | 398 | 398 |
| 3.10 | 313.5 | 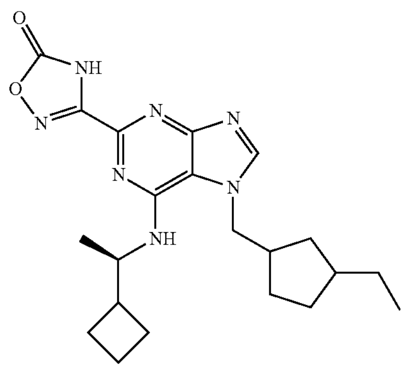 [SMILES: CCC1CCC(Cn2cnc3nc(-c4noc(=O)[nH]4)nc(N[C@H](C)C4CCC4)c32)C1] | 3-(6-(((R)-1-cyclobutylethyl)amino)-7-((3-ethylcyclopentyl)methyl)-7H-purin-2-yl)-1,2,4-oxadiazol-5(4H)-one (mixture of 4 diastereomers) | | 412 | 412 |
| 3.11 | 676.6 | 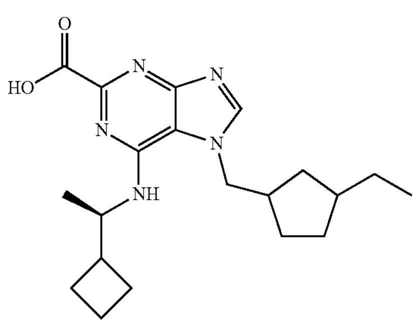 [SMILES: CCC1CCC(Cn2cnc3nc(C(=O)O)nc(N[C@H](C)C4CCC4)c32)C1] | 6-{[(1R)-1-cyclobutylethyl]amino}-7-[(3-ethylcyclopentyl)methyl]-7H-purine-2-carboxylic acid (mixture of diastereomers 1 and 2) | TFA | 372 | 372 |
| 3.12 | 145.6 | 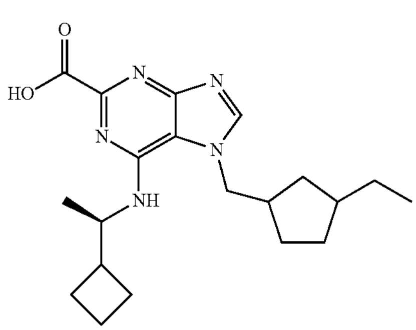 [SMILES: CCC1CCC(Cn2cnc3nc(C(=O)O)nc(N[C@H](C)C4CCC4)c32)C1] | 6-{[(1R)-1-cyclobutylethyl]amino}-7-[(3-ethylcyclopentyl)methyl]-7H-purine-2-carboxylic acid (diastereomer 3) | TFA | 372 | 372 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.13 | 509.8 | 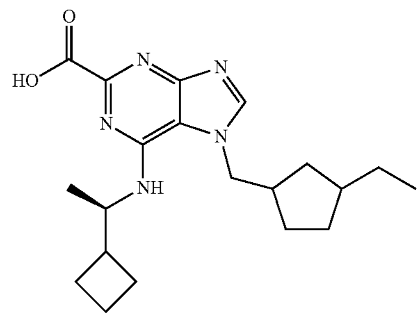 [SMILES: CCC1CCC(Cn2cnc3nc(C(=O)O)nc(N[C@H](C)C4CCC4)c32)C1] | 6-{[(1R)-1-cyclobutylethyl]amino}-7-[(3-ethylcyclopentyl)methyl]-7H-purine-2-carboxylic acid (diastereomer 4) | TFA | 372 | 372 |
| 3.14 | 189.2 | 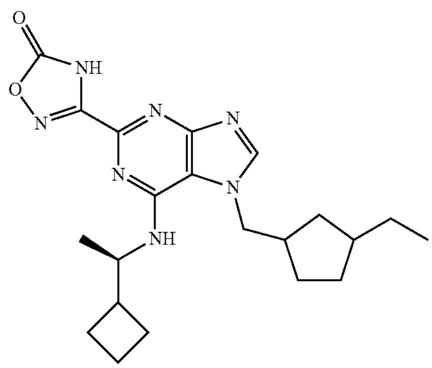 [SMILES: CCC1CCC(Cn2cnc3nc(-c4noc(=O)[nH]4)nc(N[C@H](C)C4CCC4)c32)C1] | 3-(6-{[(1R)-1-cyclobutylethyl]amino}-7-[(3-ethylcyclopentyl)methyl]-7H-purin-2-yl)-1,2,4-oxadiazol-5(4H)-one (diastereomer 3) | TFA | 412 | 412 |
| 3.15 | 430.2 | 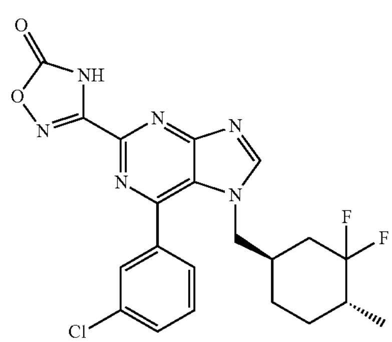 [SMILES: C[C@@H]1CC[C@@H](Cn2cnc3nc(-c4noc(=O)[nH]4)nc(-c4cccc(Cl)c4)c32)CC1(F)F] | 3-[6-(3-chlorophenyl)-7-{[(trans)-3,3-difluoro-4-methylcyclohexyl]methyl}-7H-purin-2-yl]-1,2,4-oxadiazol-5(4H)-one (enantiomer 1) | | 461 | 461 |
| 3.16 | 847.6 | 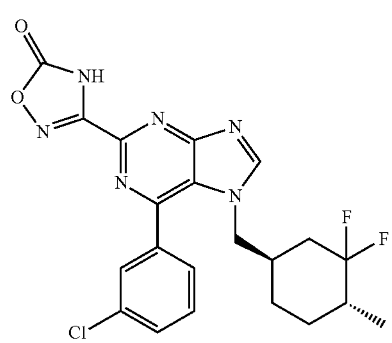 [SMILES: C[C@@H]1CC[C@@H](Cn2cnc3nc(-c4noc(=O)[nH]4)nc(-c4cccc(Cl)c4)c32)CC1(F)F] | 3-[6-(3-chlorophenyl)-7-{[(trans)-3,3-difluoro-4-methylcyclohexyl]methyl}-7H-purin-2-yl]-1,2,4-oxadiazol-5(4H)-one (enantiomer 2) | | 461 | 461 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.17 | 420.7 | 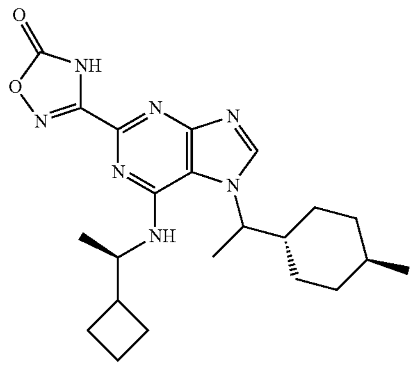 [SMILES: CC([C@H]1CC[C@H](C)CC1)n1cnc2nc(-c3noc(=O)[nH]3)nc(N[C@H](C)C3CCC3)c21] | 3-(6-{[(1R)-1-cyclobutylethyl]amino}-7-[1-(trans-4-methylcyclohexyl)ethyl]-7H-purin-2-yl)-1,2,4-oxadiazol-5(4H)-one (diastereomer 1) | | 426 | 426 |
| 3.18 | 17.00 | 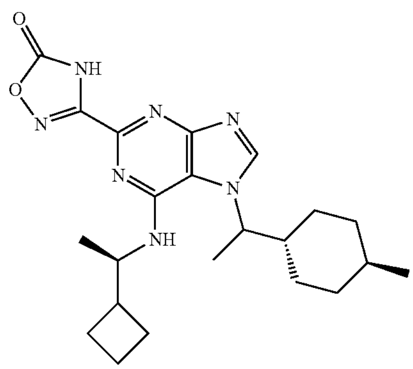 [SMILES: CC([C@H]1CC[C@H](C)CC1)n1cnc2nc(-c3noc(=O)[nH]3)nc(N[C@H](C)C3CCC3)c21] | 3-(6-{[(1R)-1-cyclobutylethyl]amino}-7-[1-(trans-4-methylcyclohexyl)ethyl]-7H-purin-2-yl)-1,2,4-oxadiazol-5(4H)-one (diasteereomer 2) | | 426 | 426 |

EXAMPLE 2

FRET Assay

Methods: An HDM2 FRET assay was developed to assess the compounds' inhibitory activity towards binding of p53 protein. A truncated version of HDM2 with residues 17 to 125 (containing p53 binding surface, Science (1994) 265, 346-355), with N-terminal His and Thioredoxin tag was generated in pET32a expression vector and expressed in *E. coli* strain BL21(DE3)Rosetta. Protein was purified using Ni-affinity chromatography, followed by size exclusion chromatography using Superdex 75 26/60 column. To assess inhibition of p53 binding to HDM2, a FITC labeled 8-mer peptide (sequence: Ac-Phe-Arg-Dpr-Ac6c-(6-Br)Trp-Glu-Glu-Leu-NH$_2$; *Anal Biochem.* 2004 Aug. 1; 331(1):138-46) with strong affinity towards p53 binding pocket of HDM2 was used. The HDM2 assay buffer contained 1× Phosphate Buffered Saline (Invitrogen, Cat#14190), 0.01% BSA (Jackson ImmunoResearch, Cat#001-000-162), 0.01% Tween-20. In the 1× assay buffer recombinant HDM2 protein, peptide and Lumi4-Tb Cryptate-conjugate mouse anti-6×HIS antibody (cisbio, Cat#Tb61HISTLB) were added and transferred to ProxiPlate PLUS (PerkinElmer, Cat#6008269), containing compounds so that final DMSO concentration is 0.1%. Final concentrations of reagents in the assay wells are 0.5 nM HDM2, 0.25 nM anti HIS (Tb label) antibody and 3 nM peptide. After two hour incubation at room temperature in a humidified chamber plates were read on EnVision plate reader with the following settings: excitation: UV, 340 nM, two emission filters: 520 nm and 495 nm respectively. Ratio of em520/em495 was used to calculate % inhibition and to obtain IC$_{50}$ with 4-parameter logistic equation.

IC$_{50}$ DETERMINATIONS: Dose-response curves were plotted from the inhibition data, from 10 point serial dilutions of inhibitory compounds. Concentration of compound was plotted against em520/Cem495 ratio signal. To generate IC$_{50}$ values, the dose-response curves were fitted to a standard sigmoidal curve and IC$_{50}$ values were derived by nonlinear regression analysis. IC$_{50}$ values in the above table are rounded to the nearest integer.

EXAMPLE 3

Cell Viability Assay

Additionally, compounds can be tested for activity at the HDM2 protein using the Cell Viability Assay, which measures the number of viable cells in culture after treatment with the inventive compound for a certain period of time e.g. 72 hours based on quantitation of the ATP present (Cell Viability. IC$_{50}$). [CellTiter-Glo® Luminescent Cell Viability Assay from Promega].

What is claimed is:

1. A compound represented by Formula I:

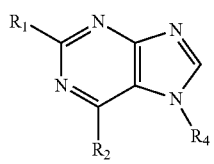

Wherein $R^1$ is selected from the group consisting of $-(CR^a{}_2)_n COOR^{11}$, $-(CR^a{}_2)_n C(O)NR^c SO_2 N(R^c)_2$, and a nitrogen containing 5-membered heteroaryl and heterocyclenyl ring selected from the group consisting of tetrazolyl, oxadiazolyl, oxadiazolone, dihydro-oxadiazolyl, triazolyl, dihydro-triazolyl, and dihydro-triazolone, wherein the 5-membered ring is optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, $-SO_2NR^cR^c$, $-NR^cSO_2R^c$, $C_1$-$C_6$alkylsulfonyl, $C_1$-$C_6$alkylamino or di($C_1$-$C_6$)alkylamino;

$R^2$ is selected from the group consisting of phenyl, pyridyl, or $-W-(CR^aR^9)_tR^7$, wherein W is $NR^c$ or O, wherein the phenyl or pyridyl is optionally substituted with $R^{12}$ selected from the group consisting of halo, CN, $-(CR^a{}_2)_z COOR^{10}$, halo$C_1$-$C_6$alkyl, $C_1$-$C_6$alkyl, $-OR^c$, $-(CR^a{}_2)_z$aryl, $-(CR^a{}_2)_z$heterocyclic, $-(CR^a{}_2)_z$cyclenyl, and $-(CR^a{}_2)_z$heterocyclenyl, wherein each of the alkyl, aryl, heterocyclic, cyclenyl and heterocyclenyl of $R^{12}$ is optionally substituted with OH, $NH_2$, nitro, CN, $CON(R^c)_2$, $-(CR^a{}_2)_z COOR^{10}$, $C_1$-$C_6$alkoxy, $C_1$-$C_6$alkyl, $C_1$-$C_6$haloalkyk, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, $-NR^cSO_2R^c$, $C_1$-$C_6$alkylamino or di($C_1$-$C_6$)alkylamino;

$R^4$ is selected from the group consisting of $-(CR^a{}_2)_m$aryl, $-(CR^a{}_2)_m$heteroaryl, $-(CR^a{}_2)_m$heterocyclic, $-(CR^a{}_2)_m C_5$-$C_6$cycloalkyl, $-(CR^a{}_2)_m$cyclohexenyl and $-(CR^a{}_2)_m$heterocyclenyl, wherein the aryl, heteroaryl, heterocyclic, cycloalkyl, cyclohexenyl, and heterocyclenyl is optionally substituted with $NH_2$, nitro, CN, $CON(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, $-SO_2NR^cR^c$, $-NR^cSO_2R^c$, $C_1$-$C_6$alkylsulfonyl, $C_1$-$C_6$alkylamino or di($C_1$-$C_6$) alkylamino;

$R^5$ is independently selected from the group consisting of H, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, and $-C_0$-$C_6$alkylheterocyclic, wherein each of the alkyl, cycloalkyl, heteroaryl, aryl, and heterocyclic is optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, and $-C_0$-$C_6$alkylheterocyclic, wherein each of the alkyl, cycloalkyl, heteroaryl, aryl, and heterocyclic is optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein each of the alkyl, alkenyl, cycloalkyl, aryl, heteroaryl or heterocyclic is optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, $-C_0$-$C_6$alkyl-$C_3$-$C_8$cycloalkyl, $-C_0$-$C_6$alkyl-heteroaryl, $-C_0$-$C_6$alkyl-aryl, $-C_0$-

C₆alkylheterocyclic, —C₀-C₆alkylheterocyclenyl, —C₀-C₆alkylcyclenyl, —(CRᵃ₂)ᵤNR⁵R⁶, —(CRᵃ₂)ᵤNR⁵SO₂R⁶, —(CRᵃ₂)ᵤSO₂NR⁵R⁶, —(CRᵃ₂)ᵤC(O)R⁵, —(CRᵃ₂)ᵤC(O)OR¹⁰, —(CRᵃ₂)ᵤCONR⁵R⁶, —(CRᵃ₂)ᵤCONR⁵OR⁶, —(CRᵃ₂)ᵤNR⁵C(O)R⁶, —(CRᵃ₂)ᵤOR⁵, —(CRᵃ₂)ₛS(O)Rᶜ, and —(CRᵃ₂)ₛS(O)₂Rᶜ;

R⁹ is independently selected from the group consisting of H, C₁-C₆alkyl, C₁-C₆haloalkyl, C₃-C₈cycloalkyl, aryl, heteroaryl, and heterocyclic, wherein each of the alkyl, cycloalkyl, aryl, heteroaryl, and heterocyclic is optionally substituted with —C₀-C₆alkylORᶜ, C₀-C₆alkylN(Rᶜ)₂, COOR¹⁰, nitro, CN, C₁-C₆alkyl, C₁-C₆haloalkyl, C₁-C₆haloalkyloxy, C₁-C₆hydroxyalkyl, C₂-C₆alkenyl, C₁-C₆alkyl-C(=O)O—, C₁-C₆alkyl-C(=O)—, C₂-C₆alkynyl, halo group, hydroxyalkoxy, —SO₂NRᶜRᶜ, —NRᶜSO₂Rᶜ, C₁-C₆alkylsulfonyl, heterocyclic, or C(O)NHRᶜ;

R¹⁰ is independently selected from the group consisting of C₁-C₆alkyl, —(CRᶜ₂)ᵤC₃-C₈cycloalkyl, —(CRᶜ₂)ᵤ-heteroaryl, —(CRᶜ₂)ᵤ-aryl, and —(CRᶜ₂)ᵤ-heterocyclic, wherein each of the heteroaryl, aryl, heterocyclic, cycloalkyl and alkyl is optionally substituted with C₁-C₆alkyl, OH, halo, or haloC₁-C₆alkyl;

R¹¹ is independently selected from the group consisting of H, C₁-C₆alkyl, —(CRᶜ₂)ᵤC₃-C₈cycloalkyl, —(CRᶜ₂)ᵤheteroaryl, —(CRᶜ₂)ᵤaryl, and —(CRᶜ₂)ᵤheterocyclic wherein each of the heteroaryl, aryl, heterocyclic, cycloalkyl and alkyl is optionally substituted with C₁-C₆alkyl, OH, halo, or haloC₁-C₆alkyl;

Rᵃ is independently H, ORᶜ, NH₂, halo, C₁-C₃alkyl, or C₂-C₃alkenyl, said alkyl or alkenyl is optionally substituted with OH, C₁-C₄alkoxy, NH₂, halo, haloC₁-C₄alkyl, C₃-C₆cycloalkyl, or C₂-C₄alkenyl;

Rᶜ is independently H or C₁-C₃alkyl optionally substituted with C₂-C₃alkenyl, C₃-C₆cycloalkyl, C₁-C₃alkoxy, OH, halo, NH₂, C₁-C₃alkylamino, or C₁-C₃dialkylamino;

n is independently 0, 1, 2 or 3;
m is independently 0, 1 or 2;
t is independently 0, 1, or 2;
z is independently 0, 1, 2 or 3;
or a pharmaceutically acceptable salt thereof.

2. The compound of claim 1, wherein
R¹ is selected from the group consisting of COOR¹¹ and a nitrogen containing 5-membered heterocyclenyl ring selected from the group consisting of oxadiazolone and dihydro-triazolone, wherein the 5-membered ring is optionally substituted with C₁-C₆alkyl, C₁-C₆haloalkyl, C₁-C₆haloalkyloxy, or halo group;

R² is selected from the group consisting of phenyl, pyridyl, or W—(CRᵃR⁹)R⁷, wherein W is NRᶜ or O, wherein the phenyl and pyridyl is optionally substituted with R¹² selected from the group consisting of halo, CN, haloC₁-C₆alkyl, C₁-C₆alkyl, and —ORᶜ, wherein the alkyl of R¹² is optionally substituted with OH, CN, halo, haloC₁-C₆alkyl, or CON(Rᶜ)₂;

R⁴ is selected from the group consisting of —(CRᵃ₂)aryl, —(CRᵃ₂)C₅-C₆cycloalkyl, and —(CRᵃ₂)cyclohexenyl, wherein each of the aryl, cycloalkyl, and cyclohexenyl is optionally substituted with CN, C₁-C₃alkoxy, C₁-C₃alkyl, haloC₂-C₃alkenyl, C₂-C₃alkenyl, C₂-C₃alkenoxy, C₁-C₃haloalkyl, C₁-C₃haloalkyloxy, C₁-C₃hydroxyalkyl, C₂-C₃alkynyl, or halo group;

R⁷ is C₃-C₅cycloalkyl optionally substituted with halo, nitro, CN, C₁-C₆haloalkyl, C₁-C₆haloalkyloxy, C₁-C₆alkyl, or —(CRᵃ₂)ᵤORᶜ;

R⁹ is H, C₁-C₃alkyl, or C₁-C₃haloalkyl, wherein the alkyl is optionally substituted with ORᶜ, N(Rᶜ)₂, heterocyclic, C(O)NHCH₂CH₂OH, C(O)NH₂, or C(O)NHC₁-C₃ alkyl;

R¹⁰ is C₁-C₃alkyl optionally substituted with OH or halo;

R¹¹ is independently selected from the group consisting of H and C₁-C₃alkyl, wherein the alkyl is optionally substituted with OH or halo;

Rᵃ is independently H, ORᶜ, NH₂, halo, C₁-C₃alkyl, or C₂-C₃alkenyl, said alkyl or alkenyl is optionally substituted with OH, C₁-C₄alkoxy, NH₂, F, CF₃, C₃-C₆cycloalkyl, or C₂-C₄alkenyl;

Rᶜ is independently H or C₁-C₃alkyl optionally substituted with C₂-C₃alkenyl, C₃-C₆cycloalkyl, C₁-C₃alkoxy, OH, halo, NH₂, C₁-C₃alkylamino, or C₁-C₃dialkylamino; and z is independently 0, 1 or 2.

3. The compound of claim 1, wherein
Rⁱ is COOH,

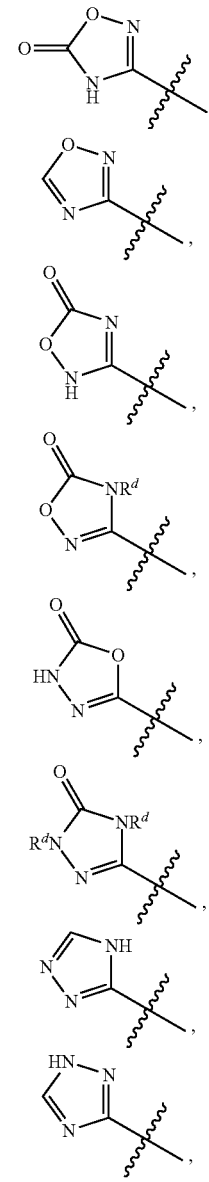

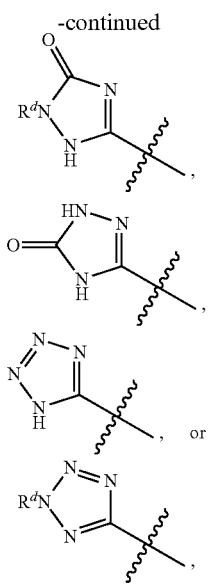

wherein $R^d$ is $CH_3$ or H.

4. The compound of claim 1, wherein $R^1$ is COOH,

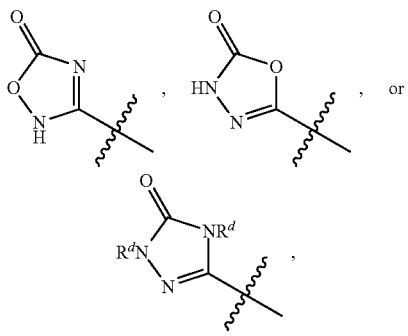

wherein $R^d$ is $CH_3$ or H.

5. The compound of claim 1, wherein $R^2$ is

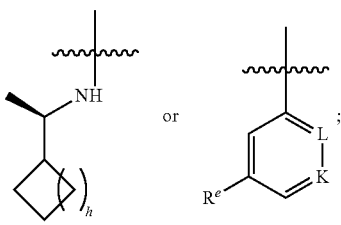

$R^e$ is H, $-(CR^a{}_2)_zC(O)OR^{10}$, CN, $OR^c$, halo, $haloC_1$-$C_3$alkyl or $C_1$-$C_3$alkyl;

K and L are independently $CR^{14}$ or N, but not both N;

$R^{14}$ is independently H, halo, CN, $haloC_1$-$C_6$alkyl, $C_1$-$C_6$alkyl, $-OR^c$, or $-(CR^a{}_2)_z$heterocyclic, wherein the heterocyclic is optionally substituted with OH, CN, halo, $haloC_1$-$C_3$alkyl, or $CON(R^c)_2$; and h is 0 or 1.

6. The compound of claim 1, wherein $R^4$ is $-CH_2$-E or $CH(CH_3)$-E, wherein E is phenyl, cyclohexyl, cyclohexenyl or cyclopentyl; wherein each of the phenyl, cyclohexyl, cyclohexenyl and cyclopentyl is optionally substituted with $haloC_1$-$C_3$alkyl, $haloC_2$-$C_3$alkenyl, halo, $C_3$-$C_4$cycloalkyl, $haloC_1$-$C_3$alkoxy, $C_1$-$C_3$alkoxy, $C_2$-$C_3$alkenoxy, $C_1$-$C_3$alkyl, $C_2$-$C_3$alkenyl, amino, or CN.

7. The compound of claim 1, wherein $R^4$ is

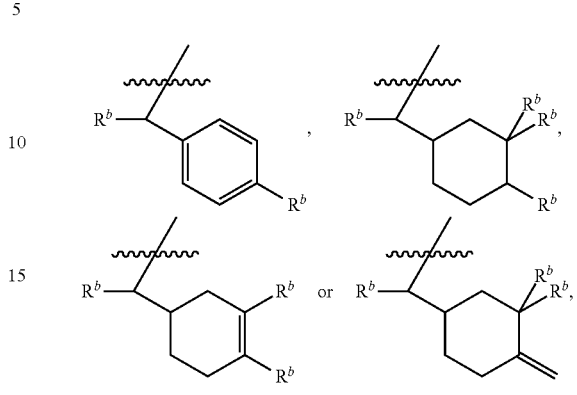

and $R^b$ is independently H, $haloC_1$-$C_3$alkyl, $haloC_2$-$C_3$alkenyl, halo, $haloC_1$-$C_3$alkoxy, $C_1$-$C_3$alkoxy, $C_1$-$C_3$alkyl, $C_2$-$C_3$alkenyl, or CN.

8. A compound selected from the group consisting of:
6-{[(1R)-1-cyclopropylethyl]amino}-7-[4-(trifluoromethyl)benzyl]-7H-purine-2-carboxylic acid;
6-{[(1R)-1-cyclobutylethyl]amino}-7-[(trans-4-methylcyclohexyl)methyl]-7H-purine-2-carboxylic acid;
5-(6-{[(1R)-1-cyclobutylethyl]amino}-7-[(trans-4-methylcyclohexyl)methyl]-7H-purin-2-yl)-2-methyl-1,2-dihydro-3H-1,2,4-triazol-3-one;
6-{[(1R)-1-cyclobutylethyl]amino}-N-(dimethylsulfamoyl)-7-[(trans-4-methylcyclohexyl)methyl]-7H-purine-2-carboxamide;
3-{6-(3-chlorophenoxy)-7-[(trans-4-methylcyclohexyl)methyl]-7H-purin-2-yl}-1,2,4-oxadiazol-5(4H)-one;
3-{6-(3,3-difluoropiperidin-1-yl)-7-[(trans-4-methylcyclohexyl)methyl]-7H-purin-2-yl}-1,2,4-oxadiazol-5(4H)-one;
3-(6-{[(1R)-1-cyclobutylethyl]amino}-7-[(trans-4-methylcyclohexyl)methyl]-7H-purin-2-yl)-1,2,4-oxadiazol-5(4H)-one;
7-(1-benzothiophen-2-ylmethyl)-6-{[(1R)-1-cyclopropylethyl]amino}-7H-purine-2-carboxylic acid;
3-{6-(3-methoxyphenoxy)-7-[(trans-4-methylcyclohexyl)methyl]-7H-purin-2-yl}-1,2,4-oxadiazol-5(4H)-one;
3-{7-[(trans-4-methylcyclohexyl)methyl]-6-[3-(trifluoromethyl)piperidin-1-yl]-7H-purin-2-yl}-1,2,4-oxadiazol-5(4H)-one;
3-{7-[(trans-4-methylcyclohexyl)methyl]-6-(3-methylpiperidin-1-yl)-7H-purin-2-yl}-1,2,4-oxadiazol-5(4H)-one;
3-{6-(3,3-dimethylpiperidin-1-yl)-7-[(trans-4-methylcyclohexyl)methyl]-7H-purin-2-yl}-1,2,4-oxadiazol-5(4H)-one;
3-{6-(3-chlorophenyl)-7-[(trans-4-methylcyclohexyl)methyl]-7H-purin-2-yl}-1,2,4-oxadiazol-5(4H)-one;
3-{6-(2-chloro-3-fluoropyridin-4-yl)-7-[(trans-4-methylcyclohexyl)methyl]-7H-purin-2-yl}-1,2,4-oxadiazol-5(4H)-one;
3-{6-(4-chloropyridin-2-yl)-7-[(trans-4-methylcyclohexyl)methyl]-7H-purin-2-yl}-1,2,4-oxadiazol-5 (4H)-one;
3-chloro-5-{7-[(trans-4-methylcyclohexyl)methyl]-2-(5-oxo-4,5-dihydro-1,2,4-oxadiazol-3-yl)-7H-purin-6-yl}benzonitrile;

3-{6-(5-chloro-2-hydroxyphenyl)-7-[(trans-4-methylcyclohexyl)methyl]-7H-purin-2-yl}-1,2,4-oxadiazol-5(4H)-one;

3-{6-(3-chloro-5-methoxyphenyl)-7-[(trans-4-methylcyclohexyl)methyl]-7H-purin-2-yl}-1,2,4-oxadiazol-5(4H)-one;

3-{6-(3-chloro-5-hydroxyphenyl)-7-[(trans-4-methylcyclohexyl)methyl]-7H-purin-2-yl}-1,2,4-oxadiazol-5(4H)-one;

3-{6-(3-bromophenyl)-7-[(trans-4-methylcyclohexyl)methyl]-7H-purin-2-yl}-1,2,4-oxadiazol-5(4H)-one;

3-{7-[(trans-4-methylcyclohexyl)methyl]-2-(5-oxo-4,5-dihydro-1,2,4-oxadiazol-3-yl)-7H-purin-6-yl}benzonitrile;

3-chloro-N-methyl-5-{7-[(trans-4-methylcyclohexyl)methyl]-2-(5-oxo-4,5-dihydro-1,2,4-oxadiazol-3-yl)-7H-purin-6-yl}benzamide;

3-{6-[3-chloro-5-(trifluoromethyl)phenyl]-7-[(trans-4-methylcyclohexyl)methyl]-7H-purin-2-yl}-1,2,4-oxadiazol-5 (4H)-one;

3-{6-(5-chloropyridin-3-yl)-7-[(trans-4-methylcyclohexyl)methyl]-7H-purin-2-yl}-1,2,4-oxadiazol-5 (4H)-one;

3-chloro-5-{7-[(trans-4-methylcyclohexyl)methyl]-2-(5-oxo-4,5-dihydro-1,2,4-oxadiazol-3-yl)-7H-purin-6-yl}benzamide;

3-{6-[3-chloro-5-(methoxymethoxy)phenyl]-7-[(trans-4-methylcyclohexyl)methyl]-7H-purin-2-yl}-1,2,4-oxadiazol-5 (4H)-one;

3-{6-(2-chloropyridin-4-yl)-7-[(trans-4-methylcyclohexyl)methyl]-7H-purin-2-yl}-1,2,4-oxadiazol-5 (4H)-one;

3-{6-(5-chloro-2-hydroxypyridin-3-yl)-7-[(trans-4-methylcyclohexyl)methyl]-7H-purin-2-yl}-1,2,4-oxadiazol-5(4H)-one;

3-{6-[3-chloro-5-(methyl sulfonyl)phenyl]-7-[(trans-4-methylcyclohexyl)methyl]-7H-purin-2-yl}-1,2,4-oxadiazol-5 (4H)-one;

3-{6-(3-chloro-5-pyrrolidin-1-ylphenyl)-7-[(trans-4-methylcyclohexyl)methyl]-7H-purin-2-yl}-1,2,4-oxadiazol-5(4H)-one;

methyl 3-methyl-5-{7-[(trans-4-methylcyclohexyl)methyl]-2-(5-oxo-4,5-dihydro-1,2,4-oxadiazol-3-yl)-7H-purin-6-yl}benzoate;

3-(6-{[(1R)-1-cyclobutylethyl]amino}-7-{[trans-4-(trifluoromethyl)cyclohexyl]methyl}-7H-purin-2-yl)-1,2,4-oxadiazol-5 (4H)-one;

3-[6-(3-chlorophenyl)-7-{[trans-4-(trifluoromethyl)cyclohexyl]methyl}-7H-purin-2-yl]-1,2,4-oxadiazol-5(4H)-one;

3-[6-{[(1R)-1-cyclobutylethyl]amino}-7-(spiro[2.5]oct-6-ylmethyl)-7H-purin-2-yl]-1,2,4-oxadiazol-5(4H)-one;

6-{[(1R)-1-cyclobutylethyl]amino}-7-(spiro[2.5]oct-6-ylmethyl)-7H-purine-2-carboxylic acid;

3-(6-{[(1R)-1-cyclobutylethyl]amino}-7-{[(1R,4R)-3,3-difluoro-4-methylcyclohexyl]methyl}-7H-purin-2-yl)-1,2,4-oxadiazol-5 (4H)-one;

3-(6-{[(1R)-1-cyclobutylethyl]amino}-7-[(3-fluoro-4-methylcyclohex-3-en-1-yl)methyl]-7H-purin-2-yl)-1,2,4-oxadiazol-5 (4H)-one;

3-(6-{[(1R)-1-cyclobutylethyl]amino}-7-[(4-methylidenecyclohexyl)methyl]-7H-purin-2-yl)-1,2,4-oxadiazol-5(4H)-one;

6-{[(1R)-1-cyclobutylethyl]amino}-7-[(4-methylidenecyclohexyl)methyl]-7H-purine-2-carboxylic acid;

3-(6-{[(1R)-1-cyclobutylethyl]amino}-7-[(3-methylcyclopentyl)methyl]-7H-purin-2-yl)-1,2,4-oxadiazol-5 (4H)-one; and 3-(6-(((R)-1-cyclobutylethyl)amino)-7-((3-ethylcyclopentyl)methyl)-7H-purin-2-yl)-1,2,4-oxadiazol-5 (4H)-one;

or a pharmaceutically acceptable salt thereof.

9. The compound of claim 1 selected from the group consisting of:

6-{[(1R)-1-cyclobutylethyl]amino}-7-[4-(trifluoromethyl)benzyl]-7H-purine-2-carboxylic acid;

3-(6-{[(1R)-1-cyclobutylethyl]amino}-7-[4-(trifluoromethyl)benzyl]-7H-purin-2-yl)-1,2,4-oxadiazol-5(4H)-one;

5-(6-{[(1R)-1-cyclobutylethyl]amino}-7-[(trans-4-methylcyclohexyl)methyl]-7H-purin-2-yl)-1,3,4-oxadiazol-2(3H)-one;

5-(6-{[(1R)-1-cyclobutylethyl]amino}-7-[(trans-4-methylcyclohexyl)methyl]-7H-purin-2-yl)-4-methyl-2,4-dihydro-3H-1,2,4-triazol-3-one;

6-(5-chloropyridin-3-yl)-7-[(trans-4-methylcyclohexyl)methyl]-7H-purine-2-carboxylic acid;

3-{6-(5-chloro-2-methylpyridin-3-yl)-7-[(trans-4-methylcyclohexyl)methyl]-7H-purin-2-yl}-1,2,4-oxadiazol-5(4H)-one;

3-{6-[3-chloro-5-(2-methoxyethoxy)phenyl]-7-[(trans-4-methylcyclohexyl)methyl]-7H-purin-2-yl}-1,2,4-oxadiazol-5(4H)-one;

5-{6-[3-chloro-5-(2-methoxyethoxy)phenyl]-7-[(trans-4-methylcyclohexyl)methyl]-7H-purin-2-yl}-1,3,4-oxadiazol-2(3H)-one;

6-{[(1R)-1-cyclobutylethyl]amino}-7-[(3-ethylcyclopentyl)methyl]-7H-purine-2-carboxylic acid;

3-[6-(3-chlorophenyl)-7-{[(trans)-3,3-difluoro-4-methylcyclohexyl]methyl}-7H-purin-2-yl]-1,2,4-oxadiazol-5 (4H)-one; and 3-(6-{[(1R)-1-cyclobutylethyl]amino}-7-[1-(trans-4-methylcyclohexyl)ethyl]-7H-purin-2-yl)-1,2,4-oxadiazol-5(4H)-one;

or a pharmaceutically acceptable salt thereof.

10. A pharmaceutical composition comprising at least one compound of claim 1 or a pharmaceutically acceptable salt thereof, in combination with at least one pharmaceutically acceptable carrier.

* * * * *